(12) United States Patent
Amiri

(10) Patent No.: US 11,925,502 B2
(45) Date of Patent: Mar. 12, 2024

(54) SYSTEMS AND METHODS FOR PRODUCING REAL-TIME CALIBRATED STEREO LONG RADIOGRAPHIC VIEWS OF A PATIENT ON A SURGICAL TABLE

(71) Applicant: TORUS BIOMEDICAL SOLUTIONS INC., Vancouver (CA)

(72) Inventor: Shahram Amiri, Vancouver (CA)

(73) Assignee: Alphatec Spine, Inc., Carlsbad, CA (US)

( * ) Notice: Subject to any disclaimer, the term of this patent is extended or adjusted under 35 U.S.C. 154(b) by 1215 days.

(21) Appl. No.: 16/393,163

(22) Filed: Apr. 24, 2019

(65) Prior Publication Data

US 2019/0320995 A1 Oct. 24, 2019

Related U.S. Application Data

(63) Continuation of application No. PCT/CA2017/051270, filed on Oct. 24, 2017.
(Continued)

(51) Int. Cl.
*A61B 6/00* (2006.01)
*A61B 34/20* (2016.01)

(52) U.S. Cl.
CPC ............ *A61B 6/584* (2013.01); *A61B 6/4405* (2013.01); *A61B 6/487* (2013.01); *A61B 6/547* (2013.01);
(Continued)

(58) Field of Classification Search
CPC ....... A61B 6/584; A61B 34/20; A61B 6/4405; A61B 6/487; A61B 6/547;
(Continued)

(56) References Cited

U.S. PATENT DOCUMENTS 7,127,090 B2   10/2006  Kreang-Arekul et al.
8,908,952 B2   12/2014  Isaacs et al.
(Continued)

FOREIGN PATENT DOCUMENTS

CA    2334495 A1    8/2002
WO    2015051468 A1    4/2015

OTHER PUBLICATIONS

Nakahara, I., et al. "Gender differences in 3D morphology and Bony impingement of human hips", Journal of Orthopaedic Research. 2011. p. 333-339 (Year: 2011).*
(Continued)

*Primary Examiner* — Keith M Raymond
*Assistant Examiner* — Sean A Frith
(74) *Attorney, Agent, or Firm* — Robert Winn

(57) ABSTRACT

Tracked mobile x-ray imaging equipment is used to produce single or stereo long calibrated views of the anatomy of a patient on the operating table. The system estimates the position and orientation of the anatomical planes, virtually places measurement grids over these reference planes, and transforms any radiographic views taking by the x-ray imaging system onto these calibrated planes. The system may apply information about the depth of the anatomy to remove parallax artifacts. This system enables displaying and evaluation of the entire radiographic length of the anatomical planes using a mobile x-ray equipment. It also provides a platform for overlaying the real time x-ray images taken during operation with radiographic images of the patient or schematic of the surgical plan developed before the surgery for quick evaluation of a surgical plan.

53 Claims, 36 Drawing Sheets

Related U.S. Application Data

(60) Provisional application No. 62/523,103, filed on Jun. 21, 2017, provisional application No. 62/412,111, filed on Oct. 24, 2016.

(52) U.S. Cl.
CPC ............ *A61B 34/20* (2016.02); *A61B 6/4441* (2013.01); *A61B 2034/2048* (2016.02); *A61B 2034/2059* (2016.02)

(58) Field of Classification Search
CPC .... A61B 2034/2048; A61B 2034/2059; A61B 6/4441
See application file for complete search history.

(56) References Cited

U.S. PATENT DOCUMENTS

| | | | |
|---|---|---|---|
| 9,109,998 B2 | 8/2015 | Nathaniel et al. | |
| 2004/0202285 A1* | 10/2004 | Masini .................... | A61B 6/032 378/197 |
| 2005/0165299 A1* | 7/2005 | Kressy .................... | A61B 90/11 606/130 |
| 2006/0176242 A1* | 8/2006 | Jaramaz ............... | G02B 27/017 345/7 |
| 2008/0161680 A1* | 7/2008 | von Jako ............... | G16H 50/50 600/407 |
| 2008/0221435 A1* | 9/2008 | Rasche .................... | A61B 5/06 600/424 |
| 2010/0172559 A1* | 7/2010 | Kumar .................... | A61B 34/20 382/154 |
| 2010/0312095 A1* | 12/2010 | Jenkins .................. | A61B 5/415 600/411 |
| 2011/0152676 A1* | 6/2011 | Groszmann .............. | A61B 6/12 600/426 |
| 2013/0172731 A1* | 7/2013 | Gole ....................... | A61B 6/506 600/424 |
| 2013/0235969 A1* | 9/2013 | Winter .................. | A61N 5/1079 378/4 |
| 2013/0297265 A1* | 11/2013 | Baloch .................... | A61B 34/10 703/1 |
| 2014/0016743 A1* | 1/2014 | Egli ....................... | G01B 15/00 378/41 |
| 2014/0323845 A1* | 10/2014 | Forsberg .................... | G06T 7/60 600/407 |
| 2015/0117608 A1* | 4/2015 | Lytle ....................... | G06T 7/0014 378/62 |
| 2015/0138186 A1* | 5/2015 | Carrell .................... | G06T 7/593 345/419 |
| 2015/0178885 A1* | 6/2015 | Kwon .................... | A61B 6/461 345/646 |
| 2015/0235364 A1* | 8/2015 | Aguirre-Valencia ........................ | G06T 7/0014 382/131 |
| 2015/0348229 A1* | 12/2015 | Aguirre-Valencia ..... | G06T 3/60 345/419 |
| 2016/0078615 A1* | 3/2016 | Zhan ........................ | G06T 7/11 382/128 |
| 2016/0157751 A1* | 6/2016 | Mahfouz .................. | A61B 6/12 600/409 |
| 2016/0171724 A1* | 6/2016 | Nett ....................... | G06T 11/006 382/131 |
| 2016/0183909 A1* | 6/2016 | Mehendale ........... | A61B 6/4405 378/205 |
| 2016/0210740 A1* | 7/2016 | Ma ............................ | G06T 7/10 |
| 2016/0220212 A1* | 8/2016 | Duewer .................... | G06T 5/50 |
| 2016/0249984 A1* | 9/2016 | Janssen .................. | A61B 6/5247 600/427 |
| 2016/0278678 A1* | 9/2016 | Valdes .................. | G01J 3/0229 |
| 2016/0278722 A1* | 9/2016 | Tagawa ................ | A61B 6/5241 |
| 2017/0020630 A1* | 1/2017 | Johnson .................. | A61B 5/064 |
| 2018/0078318 A1* | 3/2018 | Barbagli ............... | G06T 7/0012 |
| 2018/0092699 A1* | 4/2018 | Finley .................... | A61B 34/20 |

OTHER PUBLICATIONS

Binder, N. et al., The Surgeon's Third Hand an Interactive Robotic C-Arm Fluoroscope, Mobile Robots: towards New Applications, Aleksandar Lazinica (Ed.), ISBN: 978-3-86611-314-5, InTech, Available from: http://www.intechopen.com/books/mobile_robots_towards_new_applications/the_surgeon_s_third_hand_an_interactive_robotic_c-arm_fluoroscope (2006).

Amini, M., "A Fluoroscopy-based Intraoperative Tool for Measuring Alignments in Spinal Deformity Correction Surgery", Thesis, The University of British Columbia (Jul. 2016).

Wang, L. et al., "Parallax-free intra-operative X-ray image stitching", Medical Image Analysis 14 (2010) 674-686.

Bassi, S. et al., "First test on three stitching methods with digital detectors used in radiography", Radiol Phys Technol (2013) 6:187-196.

Wang, L. et al., "Long Bone X-Ray Image Stitching Using Camera Augmented Mobile C-Arm", D. Metaxas et al. (Eds.): MICCAI 2008, Part II, LNCS 5242, pp. 578-586, 2008.

Ellanti, P. et al., "Digital stitching errors and the scoliosis clinic", Eur Orthop Traumatol (2014) 5:161-163.

Chen, C. et al., "Ruler Based Automatic C-Arm Imaging Stitching Without Overlapping Constraint", J Digit Imaging (2015) 28:474-480.

Dewaele, P. et al., "Full-leg/full-spine image stitching, a new and accurate CR-based imaging technique", SPIE vol. 3661, Feb. 1999.

Binder, N. et al., "Image Guided Positioning for an Interactive C-arm Fluoroscope", International Journal of Computer Assisted Radiology and Surgery, Jun. 2006.

Livyatan, H. et al., "Robust Automatic C-Arm Calibration for Fluoroscopy-based Navigation: a Practical Approach," Medical Image Computing and Computer-Assisted Intervention (MICCAI 2002), 2002, vol. 2489, pp. 60-68.

Grzeda, V. et al., "C-arm rotation encoding with accelerometers", Int. J. Comput. Assist. Radiol. Surg., vol. 5, No. 4, pp. 385-391, 2010.

Amiri, S. et al., "A novel multi-planar radiography method for three dimensional pose reconstruction of the patellofemoral and tibiofemoral joints after arthroplasty", J. Biomech., vol. 44, No. 9, pp. 1757-1764, 2011.

Vidal, C. et al., "Role of Intraoperative Radiographs in the Surgical Treatment of Adolescent Idiopathic Scoliosis", J. Pediatr. Orthop. 2016; 36:178-186.

Kainz, B. et al., "Fast Marker Based C-Arm Pose Estimation", Med. Image Comput. Assist. Interv., vol. 11, No. Pt 2, pp. 652-659, 2008.

Reaungamornrat, S. et al., "Tracker-on-C for Cone-Beam CT-Guided Surgery: Evaluation of Geometric Accuracy and Clinical Applications", Proc. SPIE, vol. 8316. pp. 831609-831611, 2012.

Navab, N. et al., "Camera Augmented Mobile C-Arm (CAMC): Calibration, Accuracy Study, and Clinical Applications", IEEE Trans Med Imaging, vol. 29, No. 7, pp. 1412-1423, 2010.

Yaniv, Z. et al., "Long Bone Panoramas from Fluoroscopic X-ray Images," IEEE Trans. Med. Imaging, vol. 23, No. 1, pp. 26-35, 2004.

Messmer, P. et al., "Image Fusion for Intraoperative Control of Axis in Long Bone Fracture Treatment", Eur J Trauma, vol. 32, No. 6, pp. 555-561, 2006.

Apivatthakakul, T. et al., "Intraoperative panoramic image using alignment grid, is it accurate?", Arch. Orthop. Trauma Surg., vol. 133, No. 7, pp. 953-959, 2013.

Supakul, N. et al., "Diagnostic errors from digital stitching of scoliosis images—the importance of evaluating the source images prior to making a final diagnosis", Pediatr. Radiol., vol. 42, No. 5, pp. 584-598, 2012.

Amiri, S. et al., "A low-cost tracked C-arm (TC-arm) upgrade system for versatile quantitative intraoperative imaging", Int. J. Comput. Assist. Radiol. Surg., vol. 9, No. 4, pp. 695-711, 2014.

* cited by examiner

Sacrum in the Middle of the Image

Sagittal Reference Image

Sacrum in the Middle of the Image

Coronal Reference Image

Markings of the Desired
portion of the anatomy
on the Coronal and

Template fit to the Pre-operative X-ray for the purpose of Co-registration during a Spinal Surgery Template fit to the Pre-operative X-ray for the purpose of Co-registration during a Spinal Surgery

SYSTEMS AND METHODS FOR PRODUCING REAL-TIME CALIBRATED STEREO LONG RADIOGRAPHIC VIEWS OF A PATIENT ON A SURGICAL TABLE

CROSS-REFERENCE TO RELATED APPLICATIONS

This application is a continuation of PCT application No. PCT/CA2017/051270 filed 24 Oct. 2017, which claims priority from U.S. application No. 62/412,111 filed 24 Oct. 2016 and U.S. application No. 62/523,103 filed 21 Jun. 2017. For purposes of the United States, this application claims the benefit under 35 U.S.C. § 119 of U.S. application No. 62/412,111 filed 24 Oct. 2016 and U.S. application No. 62/523,103 filed 21 Jun. 2017 entitled SYSTEMS AND METHODS FOR PRODUCING REAL-TIME CALIBRATED STEREO LONG RADIOGRAPHIC VIEWS OF A PATIENT ON A SURGICAL TABLE, both of which are hereby incorporated herein by reference for all purposes.

FIELD OF THE INVENTION

This invention relates to X-ray imaging. The invention has particular application to X-ray imaging during surgery. The invention provides systems and methods for generating long radiographic views of a patient's anatomy, systems and methods for assessing the geometry of patients' anatomies and systems and methods for evaluating surgical results.

BACKGROUND

It can be very valuable to obtain accurate information about the shape of a patient's long operative anatomy during a surgical operation. Having such information available during an operation can help a surgeon to make necessary adjustments to the position, orientation, or alignment between the bone and hardware during the course of the surgery. Currently-available intraoperative imaging tools such as X-ray film-based systems and C-arm fluoroscopy cannot effectively provide required information about long operative anatomies due to limited field of view and/or poor quality. In addition, making the comparison between the images acquired during the surgery and the surgical plan can be subjective, prone to errors, and can take avoidable extra time from the operation.

X-Ray Film-Based Methods

X-ray film-based methods use elongated cassettes and films to image long operative anatomies [1]. Such cassettes may be too short for some applications, such as imaging the spine. Even a long (e.g. 36") cassette may not be large enough to depict all of the anatomical landmarks that are necessary for complete radiographic assessment of alignment (e.g., cervical spine, shoulders, and femoral heads) [2]. This limitation can make it necessary to use two images with sufficient overlapping areas in order to perform a complete radiographic assessment. However, obtaining two images involves increased radiation exposure and can take a significant amount of time. In addition to the complications associated with stitching of X-ray films, acquiring intraoperative sagittal images with plain films is challenging, due to the poor quality of such images in areas with a large tissue thickness (e.g., pelvis and shoulder areas) [2]. For sagittal views, X-ray films should be draped to avoid infection.

Fluoroscopy-Based Methods

Panoramic views may be created from images obtained intraoperatively by a C-arm fluoroscopy machine. In the normal use of fluoroscopy equipment, X-rays with a small field of view are used by surgeons to assess spinal alignment. Various methods for generating long radiographs from small fluoroscopy images have been proposed. These methods can be categorized into two main groups: 1) tracking-based methods and 2) fiducial-based methods.

Tracking-based methods generate panoramic views by tracking the pose (position and orientation) of the C-arm's source-detector set (full three-dimensional spatial coordinates of the detector and the corresponding position of the X-ray source). These methods utilize an external tracking system to estimate the pose of the C-arm with respect to a global coordinate system. A tracking system may be calibrated using: 1) on-line methods or 2) off-line methods [3]. Calibration provides parameters of a transformation ("transformation parameters") that relate inputs (such as a position determined by an external tracking system and/or joint positions of the C-arm) to the position and orientation of the X-ray source and detector. On-line methods determine transformation parameters using the presence of markers in images. Off-line methods determine transformation parameters based on a number of projection views of a calibration phantom acquired in a previous step. The real-time (or intraoperative) pose for each X-ray image can then be determined based on the previously-established off-line calibration. The transformation parameters can subsequently be used to determine the C-arm pose for each X-ray shot (x, y, and z coordinates of the source and detector, pixel scale, and image orientation for each shot may be provided, for example).

Various systems have been developed for estimating the pose of C-arm machines and using this information to provide calibrated images (i.e. images combined with information that specifies the locations of the X-ray source and detector and optionally the pixel scale and orientation of the image ("calibration information"). Calibrated images, using transformation information from online or offline calibration, can be combined with one another to generate long radiographs.

An example online calibration method used a panel consisting of small markers that were used as references to estimate the pose of a C-arm [4]. The large number of markers in the panel occluded the anatomical structures in the X-ray images and reduced the visibility of the anatomy. Another example method used accelerometers to monitor the orientation of the C-arm. This method was not able to cover a large imaging volume [5]. External tracking systems (optical tracking and magnetic tracking) are often limited by the requirement of line of sight or influence of magnetic fields [6], [7]. Camera-augmented C-arm (CAMC) is an another system that may be used to recover the pose of a C-arm machine [8]. CAMC incorporates a video camera along with the C-arm machine to recover the pose of the C-arm. The main limitations of this system are the need for significant modifications to the C-arm machine as well as line-of-sight for sagittal views. Even though the ability of a CAMC system to provide long views has been demonstrated [9], [10], limitations of CAMC systems in producing sagittal views make them not useful for spine surgery.

Fiducial-based systems estimate image parameters based on the projections of fiducials in images. A radio-opaque ruler has been utilized in different studies to generate long views [11], [12]. These systems first segment graduations of the ruler in X-ray images and then determine the transformation between the images based on a feature-based alignment method. Radio-opaque custom-made panels have also been applied i to align X-ray images [13], [14]. These panels comprise patterns that can be used to generate a long view. Some limitations of fiducial-based systems are: 1) they assume the anatomy to be planar, 2) they assume that the image is parallel to the plane of anatomy, and 3) they assume a constant distance between the image and anatomy. For some surgical applications such as spine surgery, these limitations are not acceptable since rough estimates of the spinal alignment as a flat surface can introduce difficulties.

Image-Stitching

There are various approaches to making intra-operative long stitched radiographic images. These include using a rotating X-ray source [10], stitching of long plain films [15], stitching of CR-based images [1], ruler (or marker based) stitching [13], [14] or use of an externally tracked C-arm [9], [16]. Linear stitching which involves moving the image source and detector creates s artifacts [17] that make linear stitching undesirable for accurate measurements and evaluations.

Parallax-Correction

Parallax is a displacement in the apparent position of an object viewed along two different lines of sight. Parallax can cause shifts in the positions of the same features in two X-ray images acquired using different X-ray source positions. One way to correct for parallax is to rotate a C-arm and guide the surgical table to the desired position to acquire images [10], however this seems to be impractical for imaging during a surgical operation and would not be able to produce lateral or oblique long views. Another method [18] suggests first aligning two images based on fiducial markers, and then manually adjusting the plane of interest until an acceptable match between the views is produced. This method however does not account for variation of the object-to-image distance for pixels local to each image, and is not practical for lateral views. As another limitation, these images are not calibrated for direct intra-operative measurement.

There is a need for imaging apparatus and methods that can be applied to determine the geometry of a patient's anatomy during surgery and/or verify surgical results and/or create calibrated long views of a patient's anatomy.

SUMMARY

This invention has a number of aspects that may be applied individually or in combinations. These aspects include:
- methods and apparatus useful for generating long views by stitching together smaller X-ray images and/or accurately determining the spatial relationships of smaller X-ray images with respect to one or more anatomical planes;
- methods and apparatus useful for obtaining images useful for evaluating progress of an operation;
- methods and apparatus useful for measuring aspects of the geometry of a patient's anatomy;
- methods and apparatus for registering pre-operative images to images acquired during a surgical procedure; and/or
- methods and apparatus useful for comparing a configuration of a patient's anatomy to a surgical plan.

The disclosed technology provides the capability for visualizing the shape of long operative anatomies accurately and in real time using tracked X-ray imaging equipment, such as a mobile fluoroscopy C-arm X-ray machine.

The disclosed technology allows templates of various designs to be superposed on X-ray images. The templates may be used to check alignments of features of a patient's anatomy.

The disclosed technology permits accurate measurements of features of a patient's anatomy.

One example aspect of the invention provides methods for generating long calibrated radiographic views of the anatomy of a patient on a surgical table using images obtained using a position-tracked x-ray system such as a mobile C-arm fluoroscopy device. The method comprises registering an approximate reference direction and planes of the patient's body or the operative anatomy based on analysis of data from spatial tracking of the device. In an example embodiment, an operator aligns the X-ray machine to image a set of particular projections of the anatomy. The X-ray machine is aligned so that the projections are at known locations in the images (e.g. by aligning a C-arm of the X-ray machine so that a particular projection is centred on a display). By analyzing the corresponding positions of the X-ray beam the system estimates the approximate position and orientation of the C-arm machine relative to the patient.

The system may for example estimate positions of anatomical planes of patients (e.g. coronal and/or sagittal planes). After registering the location and orientation of the anatomical planes, the system may operate to transform new images taken by the system directly onto the registered anatomical planes by applying appropriate warping of the image and/or positional transformation of boundaries of the image. Such a transformation may correct for the parallax effects caused by changes in the location of the x-ray source during the imaging process.

In some embodiments correcting for parallax may be performed in two stages. A first stage may assume that the anatomy is approximated as a flat on the planes of the anatomy. This may cause some artifacts. To correct for such artefacts, the method may provide a second refinement stage in which the preliminary stereo stitched views of the anatomy are used to receive user input providing depth information. For example, an operator may mark or paint the geometric locations of areas of interest of the anatomy using a suitable user interface. This depth information may be used to reconstruct those areas as three-dimensional voxels. The depth information can then be used to reprocess the original x-ray beam cones and morphing the pixel data on the preliminary stitched views to remove the parallax. In an example embodiment any image is immediately transformed on to the virtual anatomical plane. Long pictures of the anatomical planes may be automatically populated with transformations of all the images. These pictures may be available to the user for viewing and evaluation.

The graphical user interface of the system allows displaying the current location of the imaging equipment as a viewfinder to help the equipment operator to place the C-arm machine in a desired pose for acquiring another image. The resulting single or stereo panoramic views can be used for three-dimensional localization of certain anatomies or measurements in two or three dimensions.

The method may also take input from calibrated pre-operative images along with schematics of the surgical plan and overlay these data on top of the acquired radiographic views of the patient. The system can also be used as a tool for virtual marking and labeling of various anatomical parts or certain landmarks, enabling the operator of the equipment to go back to any desired position and orientation. Some embodiments facilitate this by providing a moving viewfinder window in the graphical user interface.

Another example aspect of the invention provides a method involving registering an approximate reference direction and planes of the patient's body or the operative anatomy with a coordinate system of an X-ray machine based on analysis of data from spatial tracking of the X-ray machine and analysis of acquired X-ray images. The method identifies fiducial features in one or more X-ray images and, based on locations of the fiducial features applies a transformation to a template or tool and overlays the transformed template or tool onto X-ray images.

Another aspect provides apparatus for medical imaging. The apparatus comprises an x-ray machine (such as, for example, a C-arm x-ray fluoroscopy machine); a tracking system operative to determine pose and position of the x-ray machine (one example of such a system is described in PCT publication WO2015051468); a system comprising one or more data processors connected to receive image data for images acquired by the x-ray machine and pose and position data from the tracking system corresponding to the images; and a display. The system is configured by machine-readable instructions executable by the one or more data processors to generate long calibrated radiographic views by: prompting a user to position the x-ray machine to acquire plural scout images of a patient, the scout images including plural fiducial features that bear a known relationship to the patient's anatomical planes; based on a beam geometry of the x-ray machine, the positions and poses of the x-ray machine corresponding to the scout images and positions of the fiducial features in the scout images calculating a vector representation of one or more anatomical planes of the patient; transforming additional images of the patient onto the one or more anatomical planes based on the vector representation, the beam geometry of the x-ray machine, and the positions and poses of the x-ray machine corresponding to the additional images; and displaying on the display a long view corresponding to one or more of the one or more anatomical planes, the long view comprising a plurality of the transformed additional images. It is not required that the additional images overlap with one another. Positioning of the additional images may be done without any comparison of the additional images in regions of overlap between the additional images.

In some embodiments the system is further configured to adjust the transformed images for parallax. This may be done, for example, by steps comprising: displaying the long view for first and second ones of the anatomical planes on the display; prompting for user input identifying corresponding points on a structure of the patient's anatomy in each of the first and second long views; based on the user input determining a depth of the anatomical structure relative to the first and second anatomical planes; and recalculating coordinates of pixels in the transformed additional images using the determined depth of the anatomical structure. In an alternative embodiment the locations of the corresponding points are determined automatically by the system using feature recognition and/or model-based image recognition algorithms.

In some embodiments the system is configured to determine areas of overlap of the additional image and to adjust pixel values in the areas of overlap by one of blending or overwriting.

It is convenient for the display to comprise a touch screen such that the user input may comprise touches on the touch screen.

In some embodiments the long views comprise stereo long views and the system is further configured to use shape information defining a 3-dimensional shape of a structure of the patient's anatomy relative to the anatomical planes to determine a position of a feature on the structure of the patient's anatomy corresponding to a point marked on one of the long views in three dimensions using the shape information and a location of the point.

In some embodiments the long views comprise stereo long views and the system is further configured to adjust the transformed images for parallax by steps comprising: receiving user input marking depth information on the stereo long views and reprocessing the transforming of the additional images based on the depth information. The user input may comprise, for example, input by way of a touch screen or pointing device that permits a user to swipe across a length of the long views to mark the approximate shape of a feature of the patient's anatomy. The system may be configured to process the user inputs to create a voxel three-dimensional reconstruction of the shape of the feature of the patient's anatomy. In an example implementation the system is configured to reprocess the transforming of the additional images by generating a plurality of control points spaced apart along the additional images, estimating a depth of pixels corresponding to each of the control points based on the voxel three-dimensional reconstruction and computing corrected locations for the control points based on the estimated depths and generating a projective transformation that transforms the additional image to a parallax-corrected version of the additional image.

In some embodiments the long views comprise stereo long views and the system is further configured to adjust the transformed images for parallax by steps comprising: applying an image segmentation algorithm to identify corresponding points along a feature of the patient's anatomy in the stereo long views and reprocessing the transforming of the additional images based on three dimensional locations corresponding to pairs of the corresponding points.

In some embodiments the one or more anatomical planes comprises first and second non-parallel planes and the system is configured to determine depths of anatomical features relative to the first and second planes by identifying points corresponding to the same anatomical features represented in the transformed additional images in each of the first and second planes and computing 3D locations voxels corresponding to the identified points from the locations of the points in the first and second planes. The points may be identified by one or more of:

receiving user input identifying the locations of the points in the first and second planes.

the system being configured to automatically identify the anatomical structures in the transformed additional images and to automatically determine the locations of the points in the anatomical structures, for example by computing a 2D location of a center point or centroid of each of the anatomical structures in each of the first and second planes.

the system identifying as the points locations corresponding to centers of the additional views.

In some embodiments the system comprises one or more stored models corresponding to the anatomical structures and the system is configured to fit the stored models to the transformed additional images in the first and second planes by model-based image matching.

In some embodiments the system assumes that the additional images will be centered on an anatomical structure of interest. For example, where an operation is being performed on a user's spine the system may assume that the images of a set of images will be centered on the patient's spine. This assumption may be reinforced by configuring the system to instruct the user to center the field of view of a set of images on the patient's spine. The system may then determine a 3D geometry of the spine relative to the anatomical planes by determining the 2D locations in the long views corresponding to the centers of the images of the set of images. The set of images may be acquired while viewing an output of the x-ray machine in a live view mode which displays a cross-hair, circles or other indicia to indicate the center of the field of view. This allows a user to position the x-ray machine such that the spine or other anatomy of interest coincides with the center of the field of view and then trigger acquisition of an image.

Optionally in cases where the system is configured to automatically locate the points the system is configured to, after determining locations of the points, allow locations of the located points to be refined based on user inputs.

Optionally in cases where the system is configured to locate the points based on user input the system is configured to, prior to receiving the user input display indicia indicating likely locations of the points and/or after receiving the user input refine the locations of the points based on model-based image matching and/or image processing.

In some embodiments the system is configured to import shape information defining a 3-dimensional shape of a structure of the patient's anatomy relative to the anatomical planes and, in transforming the additional images of the patient onto the one or more anatomical planes, the system is configured to use the shape information to correct each additional image for parallax before adding the additional image to the one or more long views.

In some embodiments the system is configured to selectively display a template on the display, the template overlaid on the long view. The template may be a template that is a built in feature of the system and/or a template that is imported into the system, for example as part of a surgical plan. The template may, for example comprise:

A grid corresponding to a desired anatomical plane display. The grid optionally may include indicia indicating distance units.

A protractor indicating angles.

In some embodiments the system is configured to check for movement of the patient by processing one or more confirmatory images to locate distinct visual features and comparing locations of the distinct visual features in the confirmatory images with locations of the distinct visual features in one or more of the long views. The system may be configured to translate and/or rotate the long view to register the distinct visual features of the long view with the corresponding distinct visual features in the one or more confirmatory views. The translation and/or rotation may be made in response to user inputs and/or automatically.

In some implementations the system is configured to process the confirmatory images to locate the distinct visual features automatically using a feature recognition algorithm.

In some implementations the system is configured to recalculate the vector representation of the one or more anatomical planes of the patient based on locations of the distinct visual features in the confirmatory images. For example the system may be configured to recreate the long views by transforming the additional images of the patient onto the one or more anatomical planes based on the recalculated vector representation, the beam geometry of the x-ray machine, and the positions and poses of the x-ray machine corresponding to the additional images.

In some embodiments the system is configured to process the positions and poses of the x-ray machine to determine an image location of an image that could be taken with the x-ray machine at a current pose and position and to display on the display indicia indicating the image location relative to the patient. The indicia may, for example comprise one or more of a cross hair, a circle, a box, a highlight of a field of view of the image that could be taken and an outline of the field of view of the image that could be taken. The indicia may be superposed on at least one long view or on preoperative radiographic images of the patient.

In some embodiments the system is configured to import a surgical plan and to display graphical elements from the surgical plan on the display overlaid on one or more of the long views. The system may be configured to register the surgical plan to the patient based at least in part on the vector representation of the one or more anatomical planes. The surgical plan may include one or more guiding lines and the system may be configured to overlay the guiding lines on one or more of the long views. The surgical plan may include one or more preoperative planning images of the patient and the system may be configured to display on the display one or more of the planning images and to superpose on the displayed planning image indicia indicating an image location of an image that could be taken with the x-ray machine at a current pose and position of the x-ray machine. In some implementations the system is configured to receive user input commands that guide translation and/or rotation of the preoperative planning images to register the preoperative planning images with the scout images, the long views or other images acquired by the x-ray machine.

In cases where the surgical plan includes one or more preoperative planning images of the patient the system may optionally be configured to selectively display on the display one or more of the planning images superposed on one or more of the long views.

In cases where the surgical plan comprises one or more overlays comprising indicia that provide one or more rulers or protractors to allow direct visual measurements of differences in one or more locations and/or angles from corresponding locations and/or angles specified by the surgical plan the system may optionally be configured to selectively overlay one or more of the overlays on the one or more long views.

In some embodiments the system is configured to automatically register the surgical plan to the one or more anatomical planes. For example the surgical plan may include one or more coordinates of an origin and/or vector directions relative to anatomical planes and the system may be configured to automatically register the surgical plan to the anatomical planes determined by the system.

In some embodiments the system is configured to create a new long view in a new plane different from any of the anatomical planes and to display the new long view on the display.

In some embodiments the system is configured to identify a position corresponding to a first landmark of the patient's anatomy in plural long views and to determine a location of the first landmark in three-dimensions based on the identified positions. In such embodiments the system is optionally configured to identify a position corresponding to a second landmark of the patient's anatomy in the plural long views, determine a location of the second landmark in three-dimensions based on the identified positions and to automatically calculate a distance between the first and second landmarks.

Another example aspect of the invention provides apparatus for medical imaging comprising: an x-ray machine; a tracking system operative to determine pose and position of the x-ray machine; a system comprising one or more data processors connected to receive image data for images acquired by the x-ray machine and pose and position data from the tracking system corresponding to the images; a display; and an alignment guide. The system is configured by machine-readable instructions executable by the one or more data processors to generate long calibrated radiographic views by: prompting a user to position the x-ray machine in alignment with plural axes corresponding to anatomical planes of the patient using the alignment guide; based on poses and/or positions of the x-ray machine when aligned with each of the plural axes calculating a vector representation of one or more anatomical planes of the patient; acquiring additional images of the patient using the x-ray machine; transforming additional images of the patient onto the one or more anatomical planes based on the vector representation, the beam geometry of the x-ray machine, and the positions and poses of the x-ray machine corresponding to the additional images; displaying on the display a long view corresponding to one or more of the one or more anatomical planes, the long view comprising a plurality of the transformed additional images. In some embodiments the alignment guide comprises a laser that emits a beam having a known direction relative to the x-ray machine. In an example embodiment the system is configured to prompt the user to: align the x-ray machine over the top of the two hips in a sequence on the coronal plane and align the x-ray machine with the approximate centre of the patient's hips in a the sagittal view; to store pose and position information from the tracking system for each of these views; and to identify the mediolateral direction of the patient's anatomy by determining parameters defining a mediolateral line connecting the patient's hips, and determining parameters specifying a sagittal anatomical plane at the mid-point of the mediolateral line and normal to the mediolateral line.

Further aspects of the invention and features of example embodiments of the invention are illustrated in the appended drawings and/or described below.

BRIEF DESCRIPTION OF THE DRAWINGS

The appended drawings illustrate non-limiting example embodiments of the invention.

FIG. 17 is a photograph showing an example embodiment of the hardware setup and the GUI for creating and evaluation of long operative anatomies in the OR.

FIG. 23A is an example simulation of the corrected shape of the spine in the OR.

DETAILED DESCRIPTION

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than a restrictive sense.

Figure 1A:
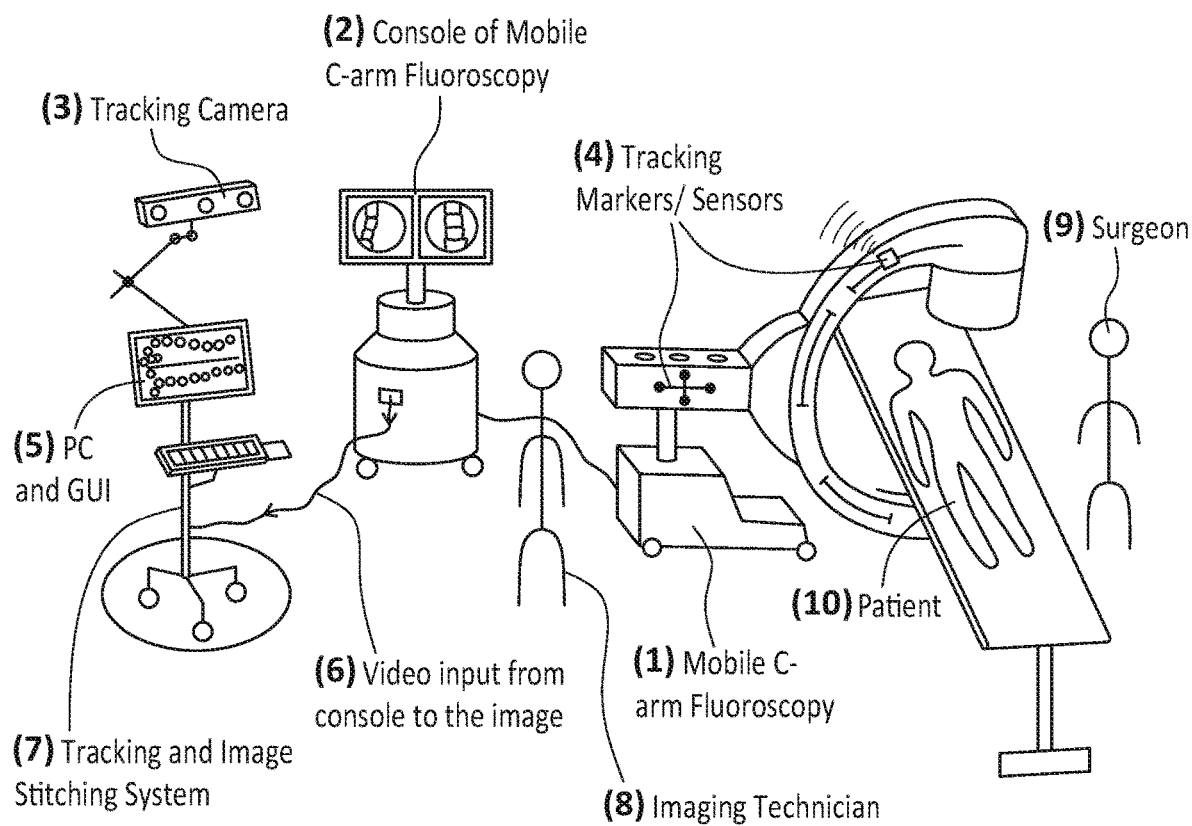
FIG. 1A is a partly schematic illustration showing an overview of an example surgical setup comprising a tracked C-arm fluoroscopy machine.

FIG. 1A schematically illustrates apparatus according to a particular example embodiment of the invention deployed in an operating room. Images are acquired using an mobile X-ray machine. Such machines may be called "fluoroscopy machines" and typically have a C shaped gantry (1 in FIG. 1A). The X-ray machine is equipped with a system to track poses of the X-ray machine (3 and 4 in FIG. 1A) when images are acquired. Tracking and stitching of images is controlled at mobile stations that can be moved to desired locations (7 in FIG. 1A), as required. Any suitable systems may be applied for monitoring the pose of the X-ray machine including systems as described in the literature. In some embodiments tracking markers and sensors on the body of the X-ray machine (e.g. markers on a C-arm) or built into the X-ray machine provide spatial tracking of the X-ray machine.

Figure 1B:
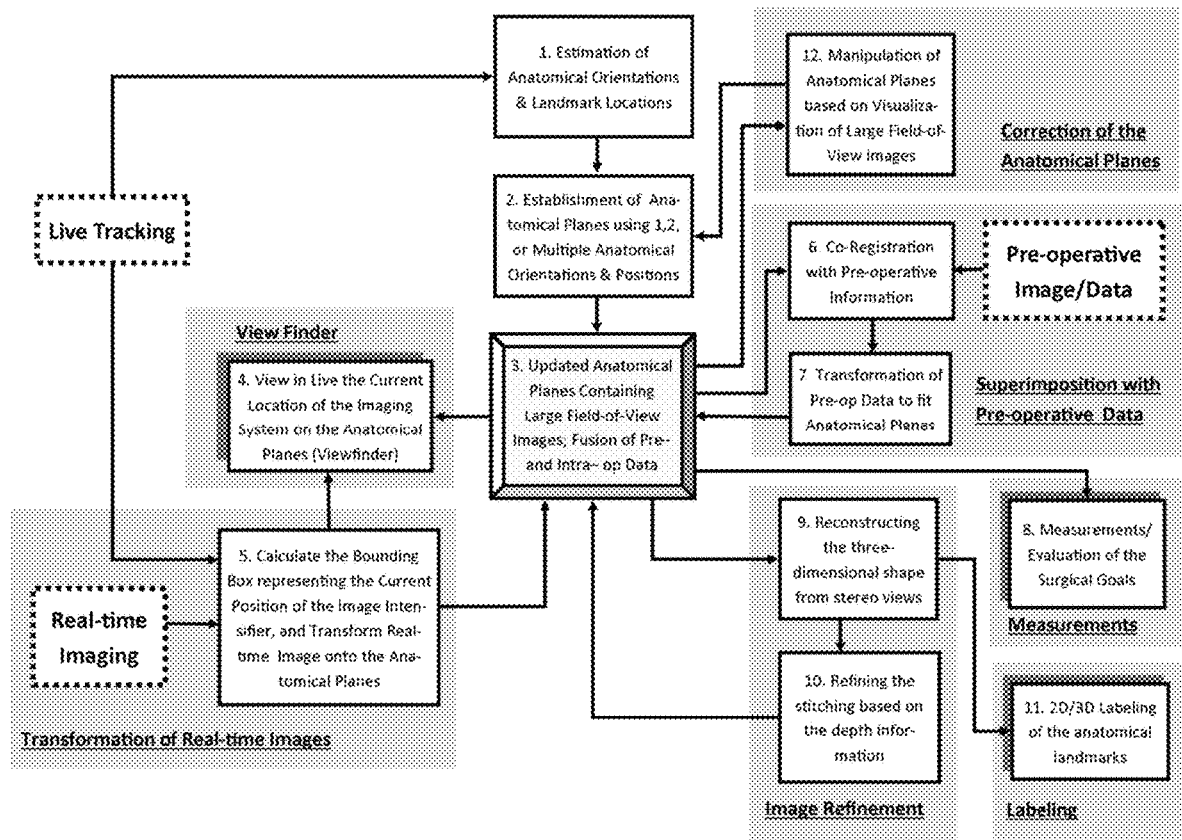
FIG. 1B is a diagram illustrating data flow among components of an example system that includes features for: one or more of live tracking, image stitching, live view finder, registration and correction of the anatomical planes, fusion with pre-operative images and planning information, and/or real-time measurement of features in intraoperative images.

FIG. 1B is a flowchart illustrating an overall process for creating and evaluating stereo views of the anatomy using apparatus as shown in FIG. 1A. With a patient in a desired position on an operating table, the process starts (Step.1 in FIG. 1B) with operating the C-arm machine to obtain radiographic images corresponding to certain views of the patient. The particular views to be obtained may depend on the selected operative anatomy. The poses of the C-arm machine for each of these views are determined by the tracking system and stored. Images corresponding to the views and the stored pose information may be applied for estimating the global or local anatomical planes of the patient (Step.2 in FIG. 1B). The user may decide to move and correct the position of the C-arm by using the X-ray projections as a feedback in an interactive way to make sure the desired views of the patient's anatomy are obtained.

A user interface (e.g. a graphical interface, 5 in FIG. 1A) may provide an operator with step by step instructions for obtaining the desired images. The desired images are selected to include recognizable anatomical features or other fiducial features that bear a known relationship to the patient's anatomical planes. For example:

anatomical planes in the area of a patient's spine may be located relative to features of the patient's hips and shoulders such as centers of the hip joints, projection of the tear-drops, and anterior superior iliac crest.

anatomical planes in the area of a patient's legs may be located relative to features of the patient's femoral neck, centres of the hip and ankle joints.

The anatomical planes may, for example, comprise one or more of the standard anatomical planes, namely:

The sagittal plane or median plane which is a plane parallel to the sagittal suture that divides the body into left and right;

The coronal plane or frontal plane which is a plane that divides the body into dorsal and ventral (back and front, or posterior and anterior) portions; and The transverse plane or axial plane which is a plane that divides the body into cranial and caudal (head and tail) portions.

Alternative embodiments may employ other planes such as planes parallel to and spaced apart from one of the anatomical planes or planes that are oblique relative to one of the anatomical planes.

Fiducial features may be selected such that they are easy to identify and image and one or more of the anatomical planes have a known relationship to the fiducial features. For example:

- the patient's mediolateral direction as a vector passing through the centres of the hip joints;
- the patient's coronal plane defined as a plane passing the mediolateral direction and approximate centroid of the S1 vertebra of the spinal column at the Sacrum level.
- the patient's proximal-distal vector on the surgical table defined perpendicular to the mediolateral direction and parallel to the horizontal reference, i.e surgical table or floor of the operating room;
- the patient's sagittal plane passes through the centroid of the S1 level and perpendicular to the coronal plane defined above;

In an example embodiment a set of radiographic images for establishing the positions of anatomical planes in the vicinity of a patient's spine may include: the projection of the anterior superior iliac spine, the flat projection of the superior plate of the S1 level, and projections of the hip centres on the coronal and sagittal planes. In another example embodiment a set of radiographic images for establishing the positions of anatomical planes in the vicinity of a patient's legs may include: the coronal or sagittal projections of the greater and smaller trochanters, the femoral heads and necks, the centres of the femoral condyles of the knee joint, the epicondylar prominent landmarks on the medial and lateral sides of the knee joint and the centre of the ankle joint.

The obtained radiographic images and the corresponding calibration information for each of the images are then used to estimate the orientation of the anatomical direction and positions of the anatomical planes (Step.2 in FIG. 1B). In some embodiments this is done by displaying to a user two or more X-ray images taken from different directions that each show one or more fiducial features such as a patient's sacrum, left and right hips, shoulders or the like. The locations of these feature(s) in each image may be marked by a user using a suitable user interface (e.g. a pointing device) or may be determined using an image recognition algorithm.

In some embodiments the X-ray machine is used as an input device for marking locations in images. For example, a user may indicate positions of landmarks by physically moving and centering the C-arm so the desired landmarks appear at the centre of the acquired image. This eliminates or reduces the need for a user to directly interact with a computer.

The locations of the fiducial features in space (in a coordinate system of the X-ray machine) may be determined from the marked locations of the fiducial features in each image using the known spatial relationships of the images (which may be determined from tracking data for the X-ray machine).

After the anatomical planes are established, the known locations of the anatomical planes in a coordinate system of the X-ray machine may be applied for various purposes including:

- A virtual template in form of a grid with calibrated dimensions in millimetres (or other units) can be superimposed onto the anatomical planes (Step 3. in FIG. 1B). When linked to live tracking, the current position of the imaging system can be shown as a view finder over the anatomical plan and the grid. This provides an intuitive graphical interface to assist the surgical staff with information about the coordinates of the imaging system with respect to the anatomical planes of the patient (Step 4. in FIG. 1B), and provides a method for estimating the lengths, angular distances, or other morphological measures of the operative anatomy.
- Any X-ray image taken by the system may be transformed into one or more of the anatomical planes based on known image parameters and position of the anatomical plane of interest relative to the pose of the X-ray machine when the X-ray image was acquired (Step 5. in FIG. 1B). The transformation may involve translation, scaling and/or warping of the X-ray image.
- Previously-acquired image data such as pre-operative 2D X-ray, stereo 2D images, 3D MRI images or CT scans or the like may be co-registered with images acquired by the X-ray machine using the known location(s) of the anatomical planes in each set of images Step 6. in FIG. 1B). This allows, for example, all or part of an X-ray image taken during an operation to be superposed on or displayed together with all or part of a detailed pre-operative image (Step 7. in FIG. 1B).
- Measurements may be made to compare geometry of different parts of a patient's anatomy using the result of image transformations to the anatomical planes (Step 8. in FIG. 1B). For example measurements may be made to:
  - Compare lengths of a patient's legs (as may be required for hip-replacement surgery for example);
  - Measure deviations of the spine from the sagittal plane (as may be required during surgery to correct scoliosis, for example);
  - Obtain measures of the global alignments of the spine in the coronal plane, such as angle between the shoulder level with respect to the mediolateral direction of the pelvis.
- For facilitating the measurements (Step 8 in FIG. 1B), templates which include indicia indicating one or more of desired positions (which may be positions relative to one or more anatomical planes), spacings and/or angles may be co-registered with an X-ray image obtained during surgery and automatically transformed into the viewpoint of the X-ray image such that quantitative measurements are preserved. In some embodiments a template may comprise a pre-operative plan indicating a desired end configuration (or range of acceptable end configurations) for a portion of the patient's anatomy. Some examples include:
  - Placement of a template in shape of a ruler or protractor, the orientation and position of which is driven according to the pre-operative information, and used to read the distance or angulation of particular parts of the anatomy with respect to each other. The visualization of these templates could be used for measuring exacts deviation of the current shape of the operative anatomy from the surgical targets. These very useful measurements are not possible using the basic fluoroscopic imaging, since these images are not calibrated and have very small field of view.
  - Placement of a custom protractor template for measuring the sagittal spinal alignment: The centre of the protractor is placed at the mid-point between the line connecting the centres of the two hips and the zero reference line passing through the centroid of T1 according to the surgical plan. The tick marks on the two sides of the zero line will help making visual measurements of how far the anatomy is from the planned position.

Placement of a custom ruler template for measuring the coronal spinal alignment: The zero mark of the ruler could be placed at the desired level (i.e. T1 level of the spine), and its orientation could be perpendicular to the vertical reference line of the pelvis. The tick marks (e.g. with millimetre measurements) can be used to make quick visual estimates of how much the spine is deviated medially or laterally in comparison to the reference line.

Information from two or more images may be used to reconstruct a portion of the patient's anatomy in three dimensions (Step 9. in FIG. 1B).

An example is reconstructing an approximate three-dimensional shape of the spinal column from long field-of-view image generated for the coronal and sagittal planes of the spine.

This 3D reconstruction can be done by manual or automatic segmentation.

The process of transformation of individual images (mentioned above and as Step 5 in FIG. 1B) assumes the desired anatomy of interest is flat and located directly on the anatomical planes. However, if the anatomy of interest has a non-planar shape or it is not perfectly positioned flat on the anatomical planes, this may produce some image ghosting artefacts, known as parallax, at the overlapping areas of the image. To remove the parallax, the three-dimensional shape of the anatomy described above (and in Step 9 in FIG. 1B) may be used to account for the local depth of the anatomy during the image stitching process (Step 10. in FIG. 1B).

In cases where it is difficult to mark or localize a particular part of the anatomy on a certain radiographic view, but the landmark is clearly discernible on a perpendicular or oblique radiograph, the three-dimensional information of the anatomy can be used to mark the anatomy (Step 11 in FIG. 1B). As an example, it can be difficult to localize a thoracic vertebral level on the sagittal view of the patient during spinal surgery. However, such landmark can be easily identified on a coronal projection. In this case if the 3D reconstruction of the anatomy is available (through Step 9 in FIG. 1B), by marking the landmarks on the coronal plane, the corresponding point on the sagittal view can be identified, highlighted or labeled.

Since the initial estimation of the anatomical planes can be prone to error, a system as described herein may provide the user with the option to further adjust and tune the orientation and position of the anatomical planes based on the visual information available on the large field-of-view images at any point during the operation (Step 12 in FIG. 1B). This can be done by simply asking the user to mark certain landmarks on the image so the planes can be realigned. This can also be done by placing a template image on top of the anatomical planes, and asking the user to move and rotate the template to the desired position and orientation based on the content of the available image. The corrected position and orientation of the anatomical planes will be used for regenerating the large field-of-view images.

For example, in spinal surgery a vector passing through the centres of the hip joints may be considered to mark the medio-lateral direction of the pelvis. In this example, if after producing a composite image of the pelvis, it was realized that the hip joints do not line up accurately with the assumed medio-lateral reference, the user may be given the option to refine the definition of the coronal and sagittal planes. By marking the line passing through the hip joints, the corrected orientation and position of the planes can be re-established.

Establishing Anatomical Planes

Figure 2A:
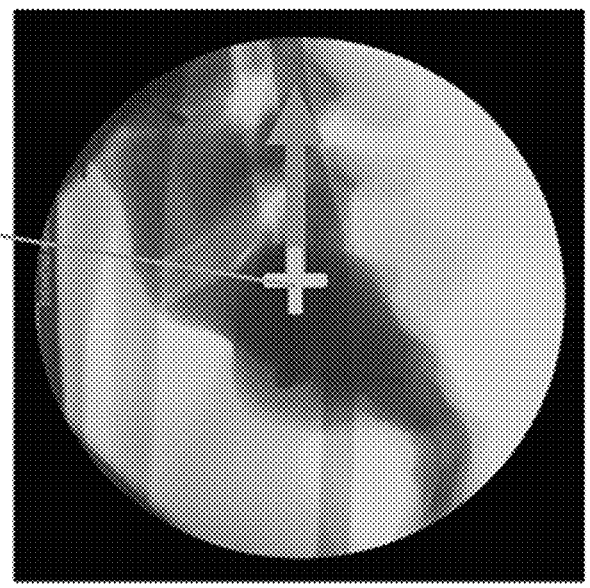
FIGS. 2A and 2B are example coronal and sagittal views of the sacrum (keeping certain landmarks centered and/or oriented in certain directions on the display of the system). Such views can be used in an analysis to estimate the approximate anatomical direction and anatomical planes positions of the operative anatomy (pelvis and spine in this example).
Figure 2A:
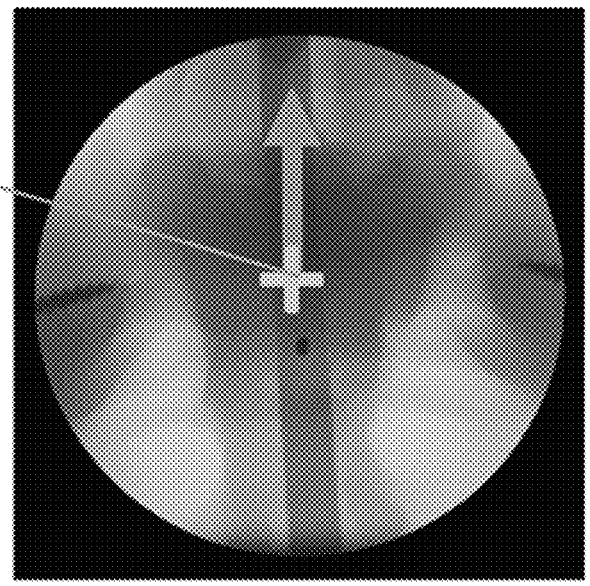
Figure 2B:
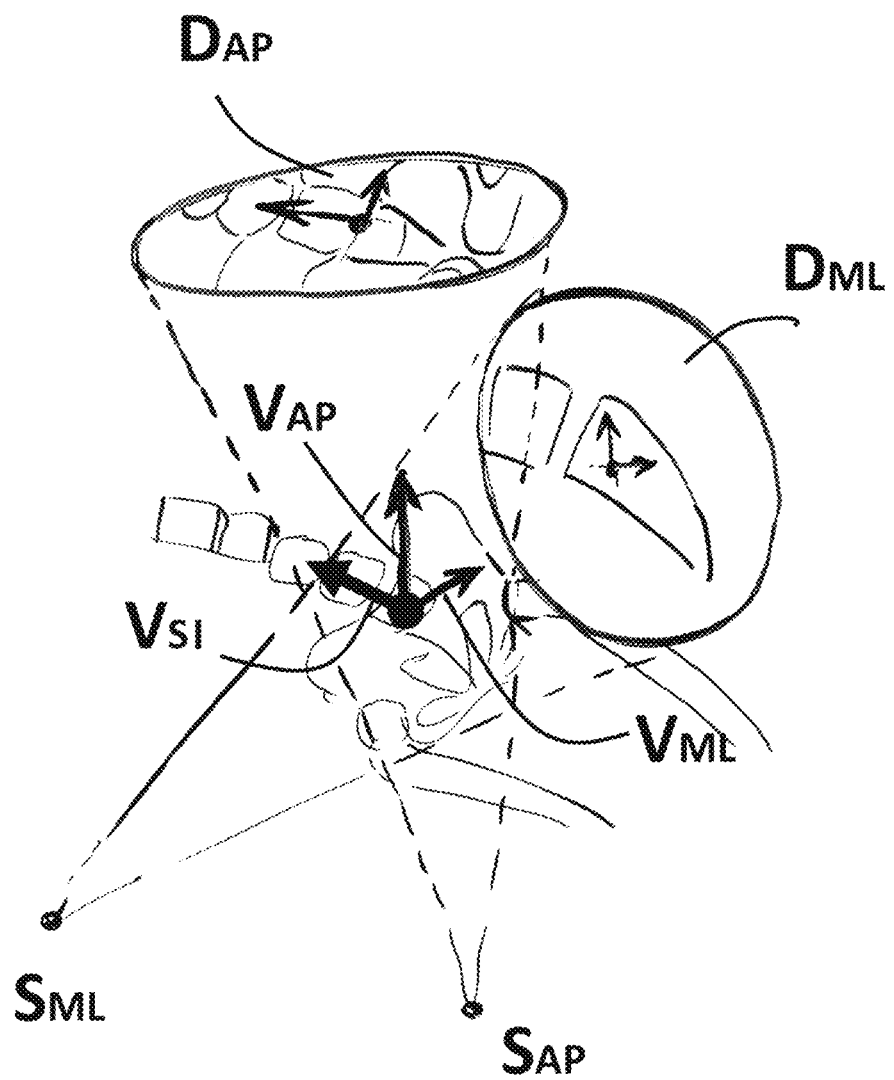

FIGS. 2A and 2B show examples of radiographic views that may be acquired and used to establish the anatomical planes of a patient. The system registers the approximate anatomical planes of the patient by asking the operator to place the C-arm in particular orientations and in predetermined alignments with (e.g. centred over) certain boney landmarks. In the illustrated example, the operator centres the fluoroscopy view with the centre point of a certain boney landmark (sacrum) on both near sagittal and coronal reference views. At least two views are needed in order for the system to be able to register the anatomical directions. In this example, the operator first creates a coronal reference view (FIG. 2A), so that the 'sacrum' is centred in the image and an imaginary vector from the centre of the image to the upper portion of the view marks the superior-inferior direction. Next, the operator rotates the gantry of the C-arm X-ray machine by 90 degrees and generates a sagittal view (FIG. 2B), using the same or other reference landmark (sacrum landmarks in this example). The operator can use the reference views to confirm or in an iterative fashion until the work is completed.

As an alternative to aligning the X-ray machine to landmarks of the patient's anatomy by observing the landmarks in x-ray fluoroscopic reference views an operator may use a guiding laser beam or other tool on the X-ray machine to achieve the desired alignments of the C-arm machine with the boney landmarks.

In an example embodiment, a user aligns an X-ray machine in a first standard position (e.g. a sagittal view centered on a patient's sacrum). This may be done while the system superposes a cross hair or other target on a live view. The user may line this target up with the patient's sacrum. When this alignment has been achieved the technician signals this by e.g. operating a button or other control. The system records the pose of the X-ray machine. The technician then aligns the X-ray machine in a second standard position (e.g. a view at 0 degrees centered on a line joining the patient's hips) and indicates to the system when this position has been achieved. The system records the pose of the X-ray machine. From the poses for the first and second standard views a processor may determine the locations of anatomical planes of the patient and locations of origins of those planes in a coordinate system used by the system.

FIG. 2B illustrates how, based on at least two beam locations, in this example $S_{ML}$-$D_{ML}$ ($S_{ML}$: Source, $D_{ML}$: Detector for the Sagittal or mediolateral (ML) view) for the sagittal view and $S_{AP}$-$D_{AP}$ ($S_{AP}$: Source, $D_{AP}$: Detector for the Coronal or anteroposterior (AP) view) for the coronal view, the system can calculate approximate orientations of the anatomical directions with respect to a frame of reference of the tracking system. In this example, from the cone axis of the sagittal beam $S_{ML}$-$D_{ML}$, the approximate mediolateral direction $V_{ML}$ is calculated. From the cone axis of the coronal beam $S_{AP}$-$D_{AP}$, the approximate anteroposterior view is calculated. The supero-inferior direction $V_{si}$ may be found by taking a cross-product of the $V_{AP}$ and $V_{ML}$ vectors.

Figure 2C:
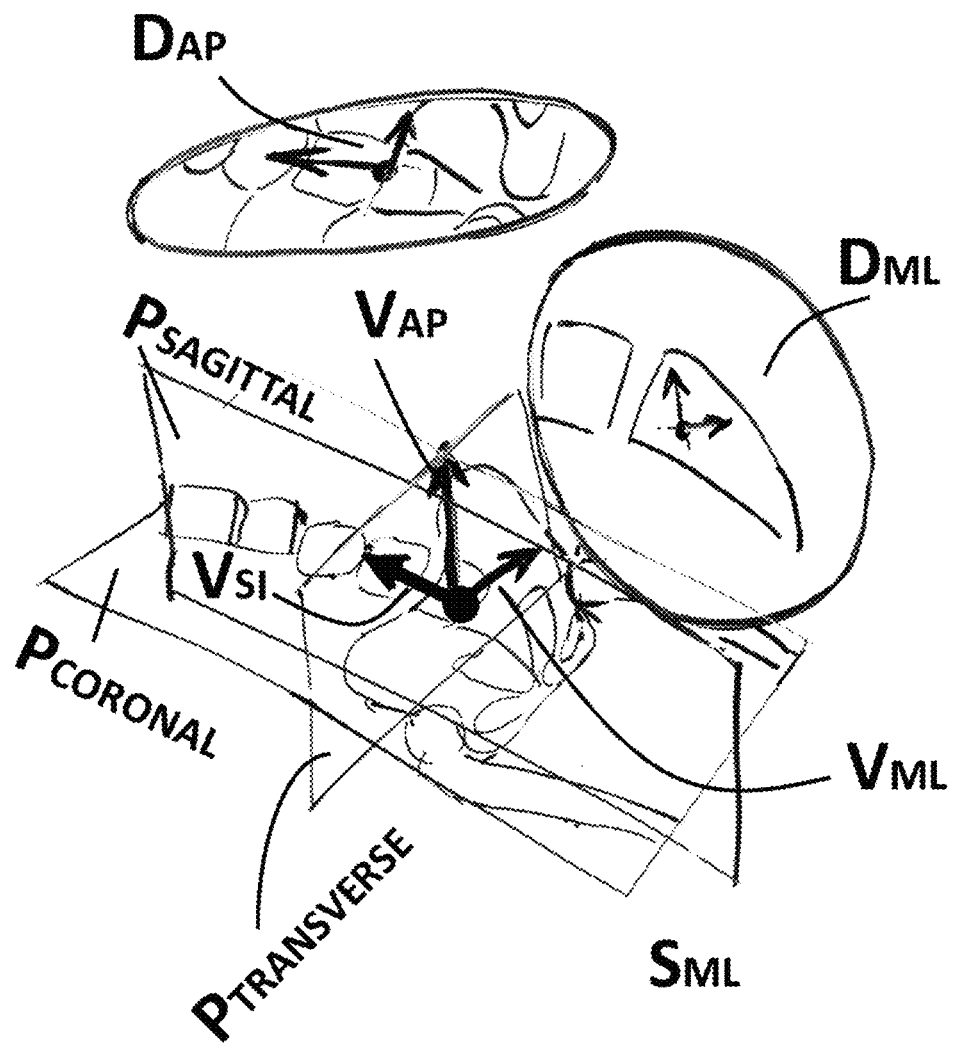
FIG. 2C is a schematic view showing the x-ray beam cones and the reference anatomical direction produced based on three-dimensional spatial coordinates of the X-ray source and the corresponding detector locations (here: $V_{AP}$, $V_{ML}$, $V_{SI}$ for Anteroposterior, Mediolateral, and Superoinferior direction vectors).

Following FIG. 2C, the approximate intersection, or closest point, between the sagittal and coronal cone axes is found as the approximate origin of the anatomical reference frame. The three anatomical planes $P_{SAGITTAL}$, $P_{CORONAL}$, $P_{TRANSVERSE}$ can then be defined for the patient on the surgical table based on $V_{AP}$, $V_{ML}$, and $V_{SI}$ (see FIG. 2D). These planes may serve as virtual base planes for creating long stitched views and/or may be used to create any offset or oblique views with respect to these main anatomical reference planes and/or may be used to assess alignment of portions of a patient's anatomy.

Figure 14:
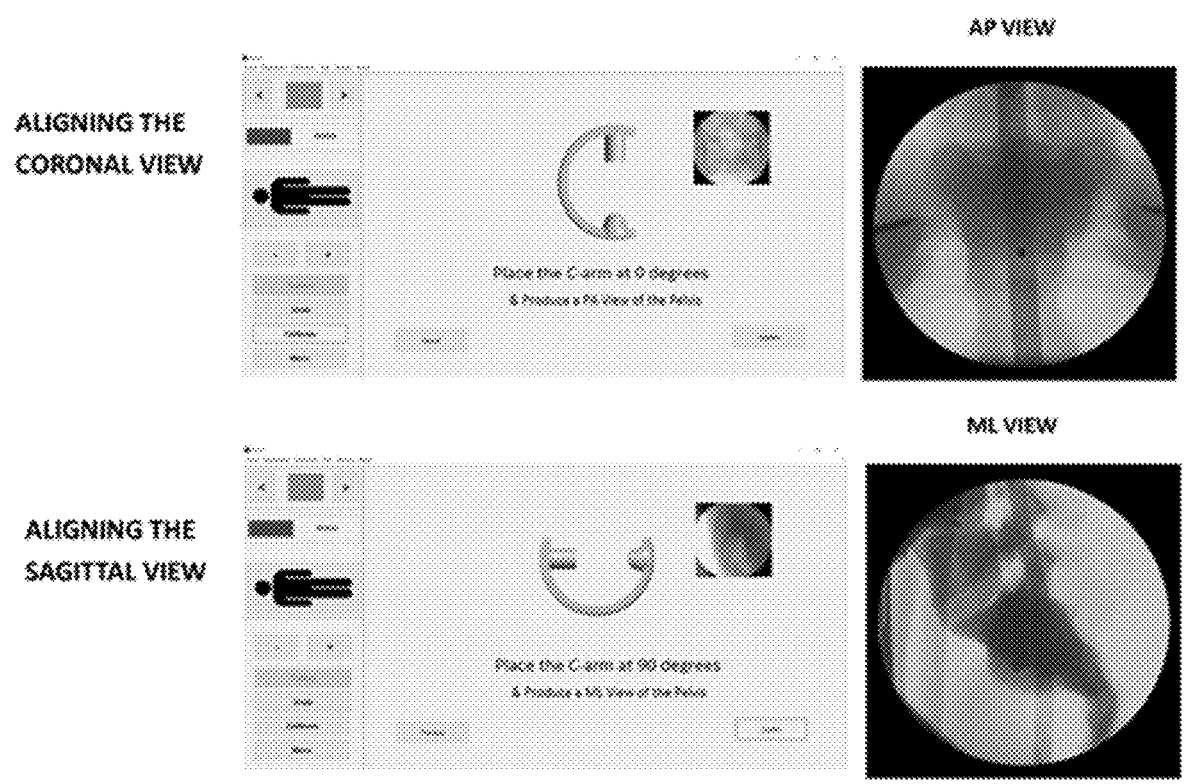
FIG. 14 shows an example graphical user interface that may be provided to guide the user in generating certain anatomical views, and recording the tracked position of the equipment for estimating the anatomical directions.

FIG. 14 shows an example graphical user interface being used to guide the operator to produce a coronal (AP) view and a sagittal (ML) view of the pelvis. Such views may be used for registering the anatomical directions and planes as described above in relation to FIGS. 2A, 2B and 2C.

Transforming Radiographic Images into Anatomical Planes

Once the anatomical planes have been established, radiographic images of the patient may be transformed into one or more anatomical planes (even if the images were acquired with the X-ray machine in a pose not corresponding to the anatomical plane). Each transformed image has essentially the same appearance as an image of the same area taken with the axis of the cone beam perpendicular to the anatomical plane with the X-ray source at a reference distance from the anatomical plane. A mosaic of such transformed images may be stitched together to provide a complete or incomplete long view of the patient's anatomy in the anatomical plane. Labeling of features (e.g. the patient's vertebrae) and measurements of the patient's anatomy can be conducted in real-time on the calibrated long views of the anatomy.

Figure 3:
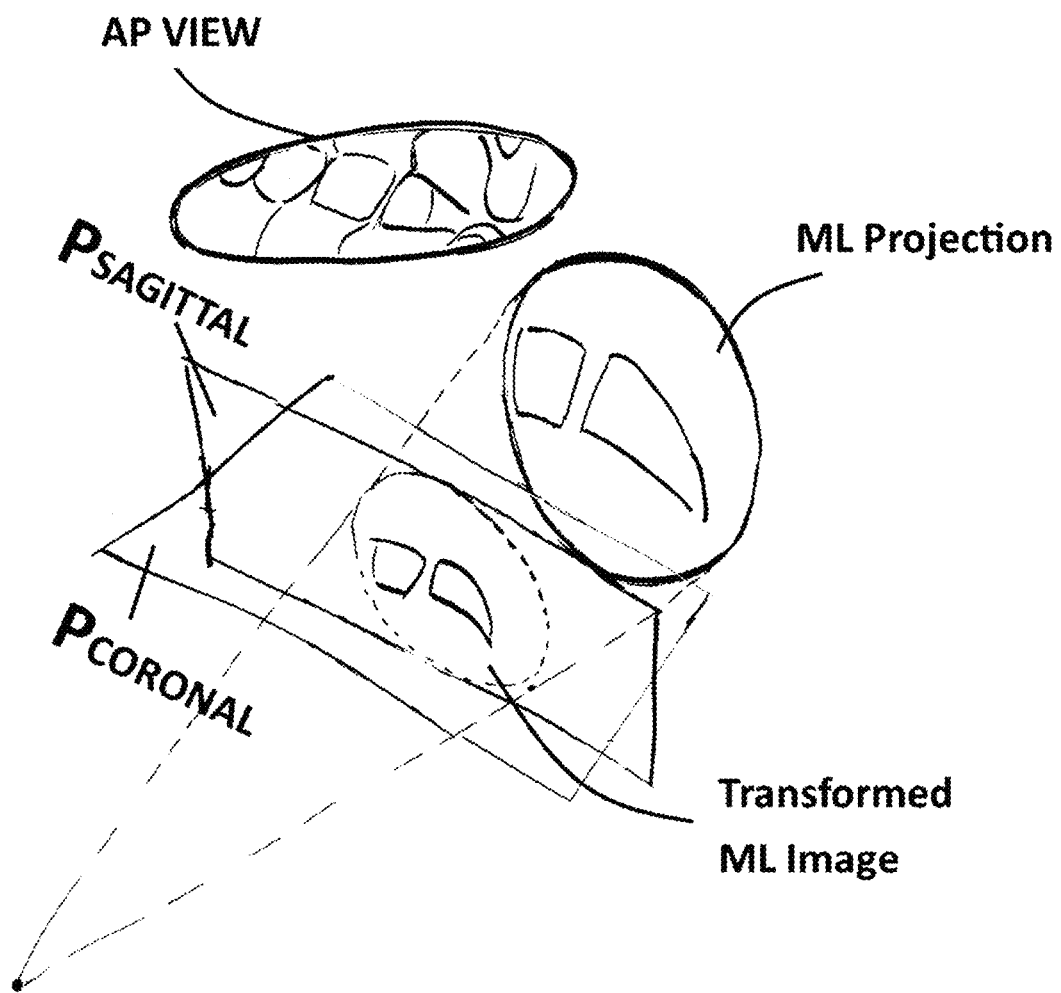
FIG. 3 illustrates obtaining additional views after registration of the anatomical planes in three-dimensions. For any radiographic views taken by the system (e.g. the sample Mediolateral (ML) image), the corresponding projection is transformed onto the desired anatomical plane to facilitate creation of a long radiographic view as more images are added.

FIG. 3 shows that an image may be transformed into a corresponding transformed images by determining an intersection of the cone beam of the image with the desired anatomical plane of interest, (for example a mediolateral (ML) projection on the sagittal reference plane $-P_{SAGITTAL}$). The boundary edges of the image on the anatomical plane define how the image has to be warped to create the transformed image that fits the boundary on the long view. If, for a particular image, the axis of the cone beam is perpendicular to the anatomical plane, the transformation is similar to a 2D scaling of the image while the position is determined by finding the intersection between the axis of the cone beam and the anatomical plane. In other cases, the image needs to be remapped (warped) based on the calculated locations of the corners or the transformed image before scaling and placement onto the corresponding anatomical plane.

Figure 5:
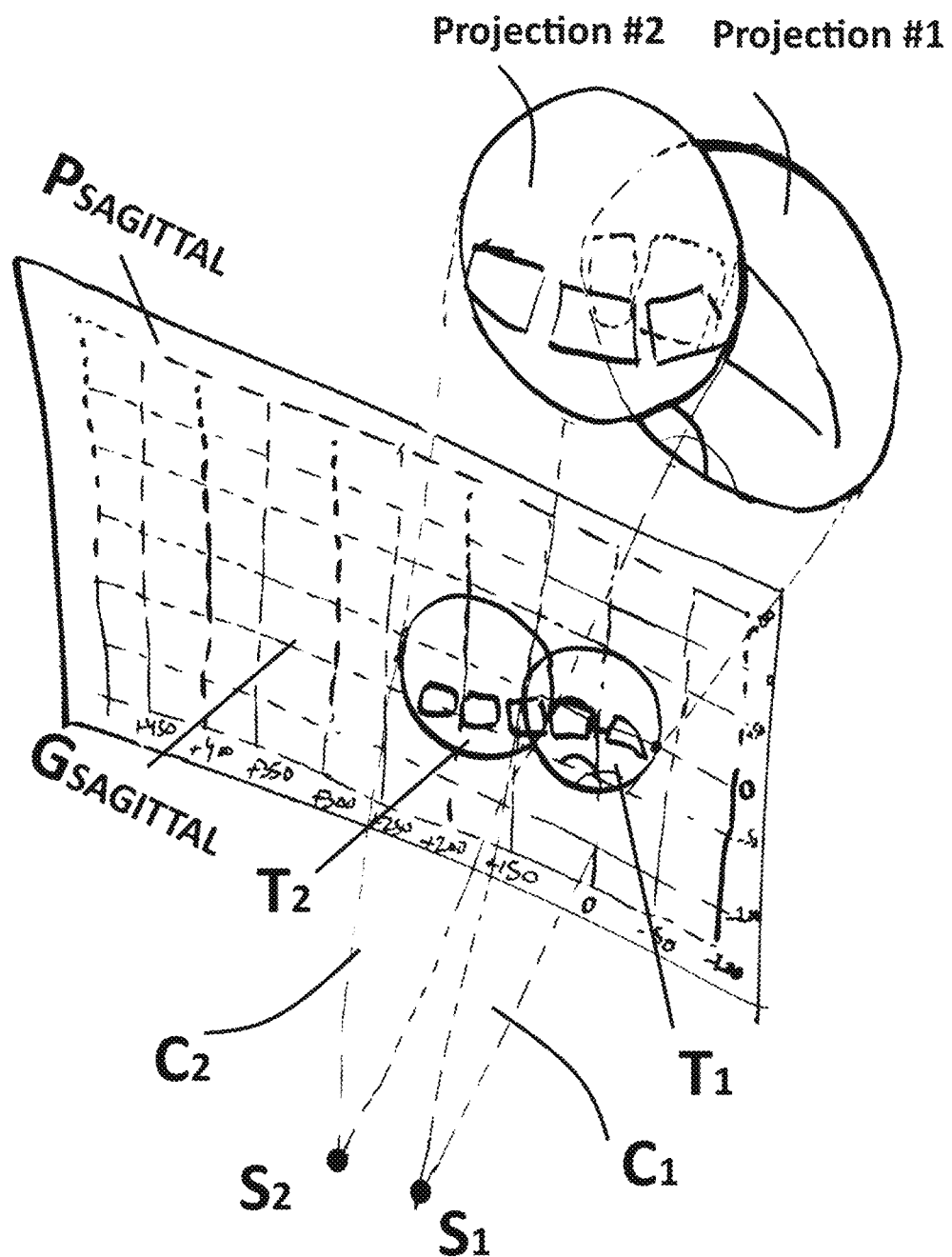
FIG. 5 shows how a grid with marked distances can be overlaid on top of a long view image as it is produced. Such a grid may be used for instantaneous evaluation of the distances and angles between different projections as they are added.

FIG. 5 shows that the same processes that are illustrated by FIG. 3 can be used to add any number of additional transformed images to a composite view in the desired anatomical plane. For each additional image the transform is found by intersecting the x-ray cone with the reference plane. In this example, for two sagittal projections #1 and #2, the transforms T1, and T2 are found by intersecting cones C1, and C2 with the sagittal plane $P_{SAGITTAL}$ as illustrated in FIG. 3 for each projection. Any parallax arising from differences in the original spatial position of images #1 and #2 and the associated ghosting effect illustrated in FIG. 5 will be at least largely removed in the transformed images T1 and T2 when they are added in the correct locations to the anatomical plane.

Additional images may, for example, be acquired at different stages of an operation. The additional images may, for example, depict parts of the patient's anatomy that have changed as a result of the operation. This allows quick iterative assessments of progress during the course of surgery.

The system may be configured to display a location at which an additional image would be added to a displayed view for a current pose and position of the x-ray machine. The system may process the positions and poses of the x-ray machine in real time to determine an image location of an image that could be taken with the x-ray machine at a current pose and position based on the beam geometry of the x-ray machine. The system may display on a live view indicia indicating the image location relative to the long view. The indicia may comprise, for example, one or more of a cross hair, a circle, a box, a highlight of a field of view of the image that could be taken and an outline of the field of view of the image that could be taken. This allows a user to use the system to position the x-ray machine to obtain a required additional image while minimizing exposure of the patient to x-rays.

It is not necessary to re-acquire images for parts of the long radiographic view in which the patient's anatomy has not changed and not moved since the images used to create those parts of the long radiographic view were acquired. The ability to continue to use previously-acquired images is advantageous because it can reduce x-ray exposure to the patient and save time. However, such images can be reused only if the relationship between the images and the patient remains known. This relationship may be lost if the patient is moved significantly or if the frame of reference of the tracking system is changed. Often users of the system will know if the patient has moved or if registration between the coordinate system of the tracking system and the patient has been lost. However, there are situations where unnoticed movements of the patient or movements of affecting the tracking system could make use of the previously acquired images unreliable.

Some embodiments of the system provide a means to check for movements of the patient relative to the reference frame of the tracking system and/or to correct the relationship of the reference frame of the tracking system and the patient. Such a capability can be useful, for example, where it is desired to repeat assessments during two phases of a surgery but between those stages it is desired to remove the x-ray system from the operating room where the surgery is being conducted.

One or more confirmatory images may be taken to verify that the rest of the anatomy depicted in the long radiographic view has not moved. These confirmatory images may include anatomical areas that have distinct visual features. In some embodiments the confirmatory images may have a reduced field of view and/or be acquired using a lower exposure than the images stitched to make the long radiographic view. In some embodiments the system is configured to guide a user to position the X-ray machine in a pose where the distinct visual features will be in the field of view of the X-ray machine.

The confirmatory images may be transformed as above and superposed on the long radiographic view. A user can then see immediately whether images of the distinct visual features in the confirmatory images exactly overlie images of the distinct visual features in the long radiographic view—indicating that the rest of the anatomy depicted in the long radiographic view has remained stationary (no movement) with respect to the surgical table and the tracking system which tracks the position and pose of the X-ray machine remains calibrated.

If the confirmatory images detect movement (i.e. the distinct visual features are not aligned in the confirmatory and long view images) the system may allow the user to shift and rotate the previously acquired long views (in relation to the established locations of the anatomical planes as described above) to compensate for detected movement of the patient in the frame of reference of the system. The system may provide a graphical user interface that allows a user to use gestures and/or or a pointing device to shift and rotate the long view images so that the images of the distinct visual features in the confirmatory images exactly overlie images of the distinct visual features in the long radiographic view.

In some embodiments the system may be configured to allow the user to identify points corresponding to the distinct visual features in the confirmatory and long views (e.g. by touching the points on a touch screen on clicking on the points with a pointing device). The system may then automatically determine and apply the shift and/or rotation of the long view required to align the corresponding points.

In some embodiments the system is configured to process the confirmatory image(s) and corresponding image(s) of the long view using feature recognition algorithms (e.g. image segmentation) to automatically recognize and determine locations of the distinct visual features in the images. The system may then automatically determine and apply the shift and/or rotation of the long view required to align the corresponding points.

In some embodiments two or more confirmatory view are acquired of the distinct visual features. This allows the system to determine 3D positions of the distinct visual features and described herein. The system may be configured to determine and apply transformation(s) to correct for any three dimensional movements of the anatomical planes that has occurred (e.g. tilt of the patient's pelvis relative to the OR table).

If the anatomy has changed too much or the patient has been moved significantly then it may be necessary to obtain new images for some or all parts of the long view.

The confirmatory images may optionally include one or more of images of:
- the same anatomical features used to determine the anatomical planes.
- artificial fiducial markers such as one or more radioopaque balls.
- an array of fiducial markers fixed to the patient (which may have a known precise three-dimensional arrangement.
- features of the patient's bones.
- other features of the patient such as screws or other implanted hardware.
- removable fiducial markers attached at known locations on the patient's anatomy during surgery.
- portions of surgical instruments placed during the surgery.
- etc.

Figure 6:
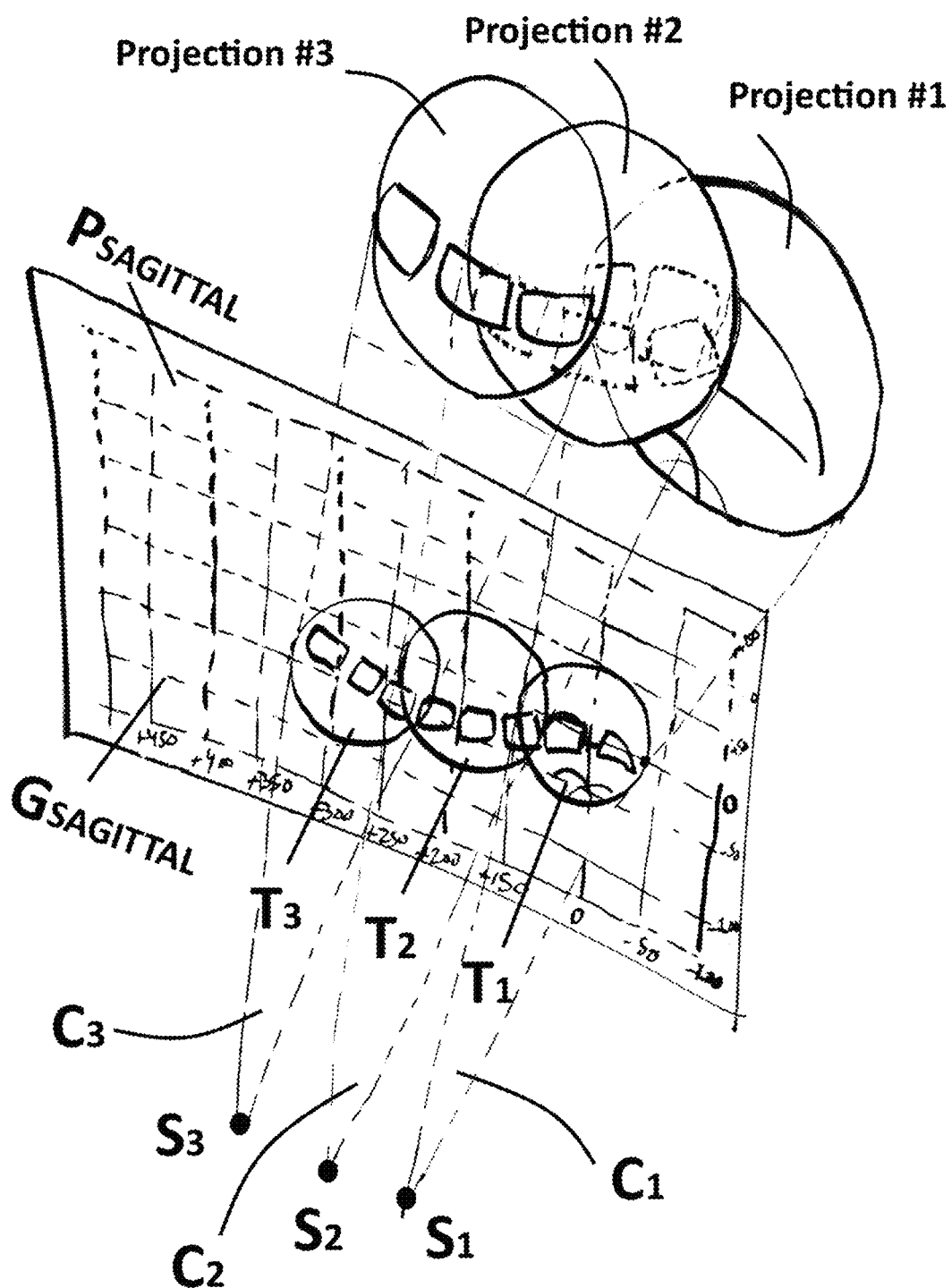
FIG. 6 illustrates how the system can transform any number of images onto the anatomical planes, allowing extension of a radiographic view to any desired area. Assuming the anatomy is close enough to the registered anatomical plane, this provides an accurate and quick evaluation during an intervention.

FIG. 6 illustrates an example in which projection #3 is transformed (T3) to the long view, at the intersection between the cone beam S3-C3, similar to the process described in relation to FIG. 5. Since projections #1, #2, and #3 are produced with the X-ray source located at different coordinates, assuming that the desired anatomy is spatially close the location of the constructed anatomical plane, this process will generate an accurate parallax-free image that can be used as a calibrated long view for quick intraoperative measurements/evaluations.

Within areas where two or more transformed images overlap (e.g. T1 and T2, or T2 and T3) the intensity values of pixels in the stitched image may be chosen to be an average or weighted combination or median of the pixel values from the original transformed images, or could be the exact intensity value of one image (e.g. the last image added—possibly overwriting the previous pixel value).

Figure 7:
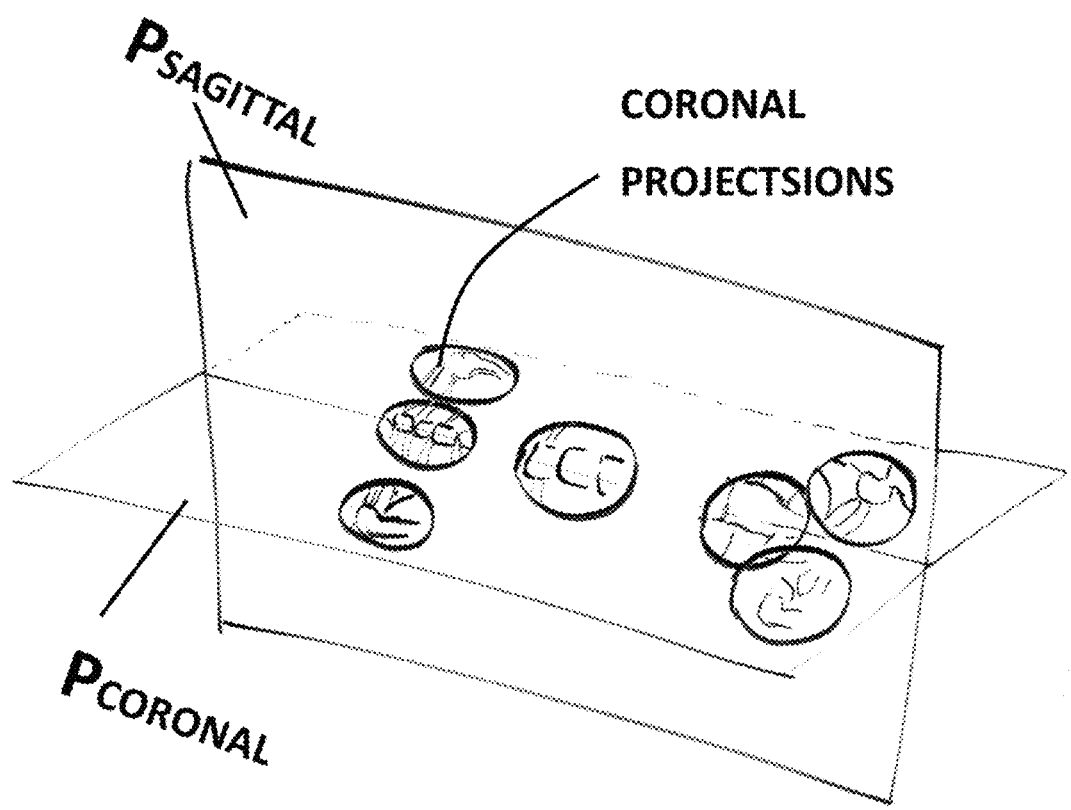
FIG. 7 illustrates transforming projections onto any of the selected anatomical planes depending on the orientation of the imaging equipment. There is no need to create overlapping views during the imaging. This feature allows for quick assessment of large anatomies by only imaging the areas that need to be visualized.

FIG. 7 shows an example wherein the system produces a long calibrated view of the patient anatomy on the coronal plane. This may be done by physically moving the imaging equipment and aligning the beam to the required orientations and collecting coronal images as described in relation to FIGS. 1 to 6. Notably, the transformed images do not need to overlap with one another to generate long views, since the spatial position and orientation corresponding to each image is provided by the tracked imaging equipment.

Figure 8A:
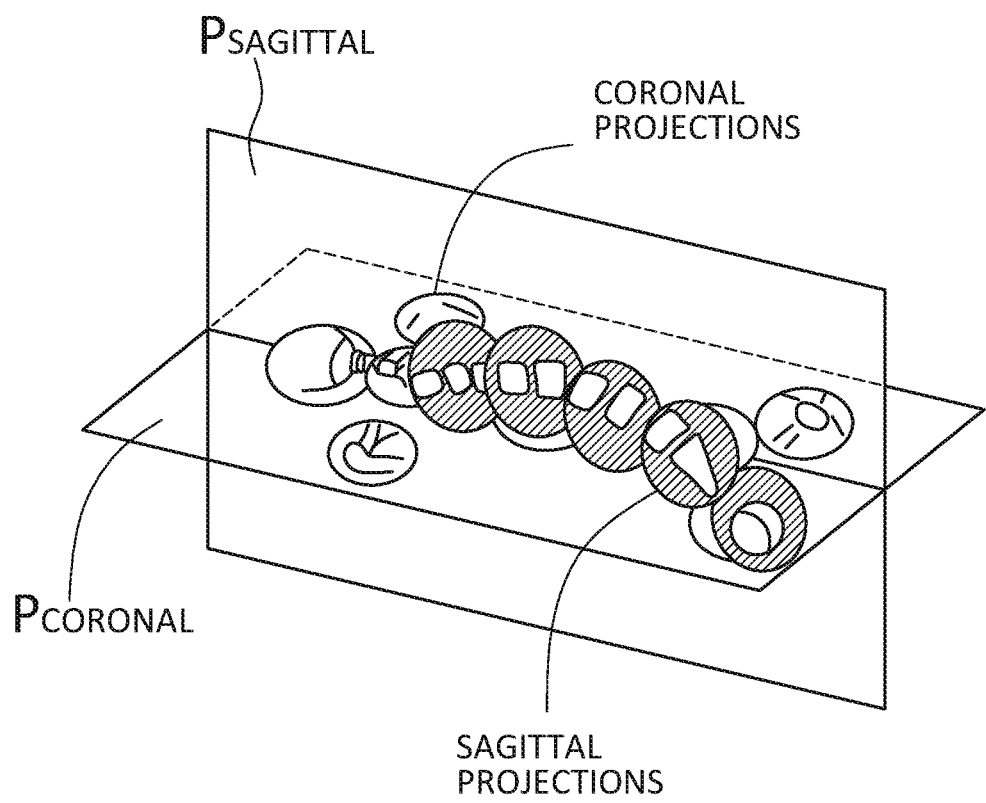
FIG. 8A illustrates how stereo radiographic views that are fully registered in three-dimensions can be positioned with respect to each other in three-dimensions to facilitate localizing particular landmarks based on two views or making three-dimensional measurements.

FIG. 8A illustrates how the resulting long projections of the anatomy on the coronal and sagittal views can be placed according to a common reference frame. Such images can be interpreted/analyzed in combination for localizing landmarks or conducting three dimensional measurements.

Templates

One example of a template is a virtual measurement grid with a desired division pattern. Such a template may be placed onto one or more of the anatomical planes to facilitate making real-time measurements and assessments. In some embodiments a user can cause the template to be displayed superposed on X-ray images taken by the X-ray machine. In cases where the images are displayed from the point of view of the X-ray machine the virtual measurement grid may be transformed so that quantitative measurements relative to the anatomical plane (e.g. distances of certain features from an origin of an anatomical plane) can be read out from the X-ray image. In cases where the X-ray image is transformed into the anatomical plane corresponding to the virtual measurement grid the virtual measurement grid may not need to be transformed.

Figure 4:
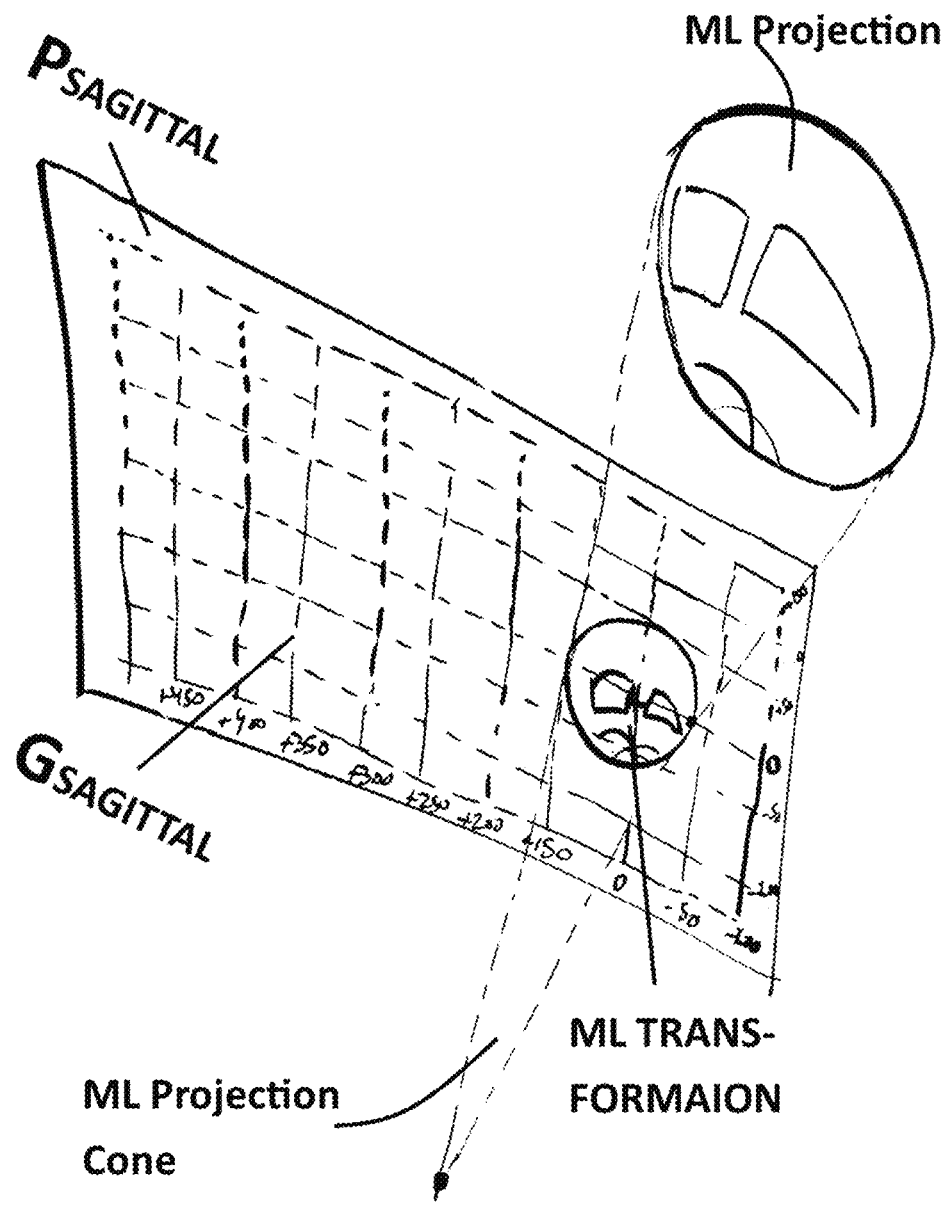
FIG. 4 shows how a calibrated virtual grid may be placed onto each of the anatomical planes, so the transformed images will be readily calibrated for measurements. The transformed image may be calculated based on intersection of the corresponding position of the x-ray beam and the anatomical reference plane.

FIG. 4 shows that a virtual 2D measurement grid, here $G_{SAGITTAL}$, with desired divisions and grid lines can be placed onto any one or more of the constructed anatomical planes, here $P_{SAGITTAL}$. The origin of the grid can be set to match the origin of the anatomical reference. The directions of the grid lines can be set to match the estimated anatomical directions ($V_{AP}$, $V_{ML}$, $V_{SI}$). The grid may be overlaid as a layer on a transformed image, making the transformed image calibrated and ready for measurements.

Figure 8B:
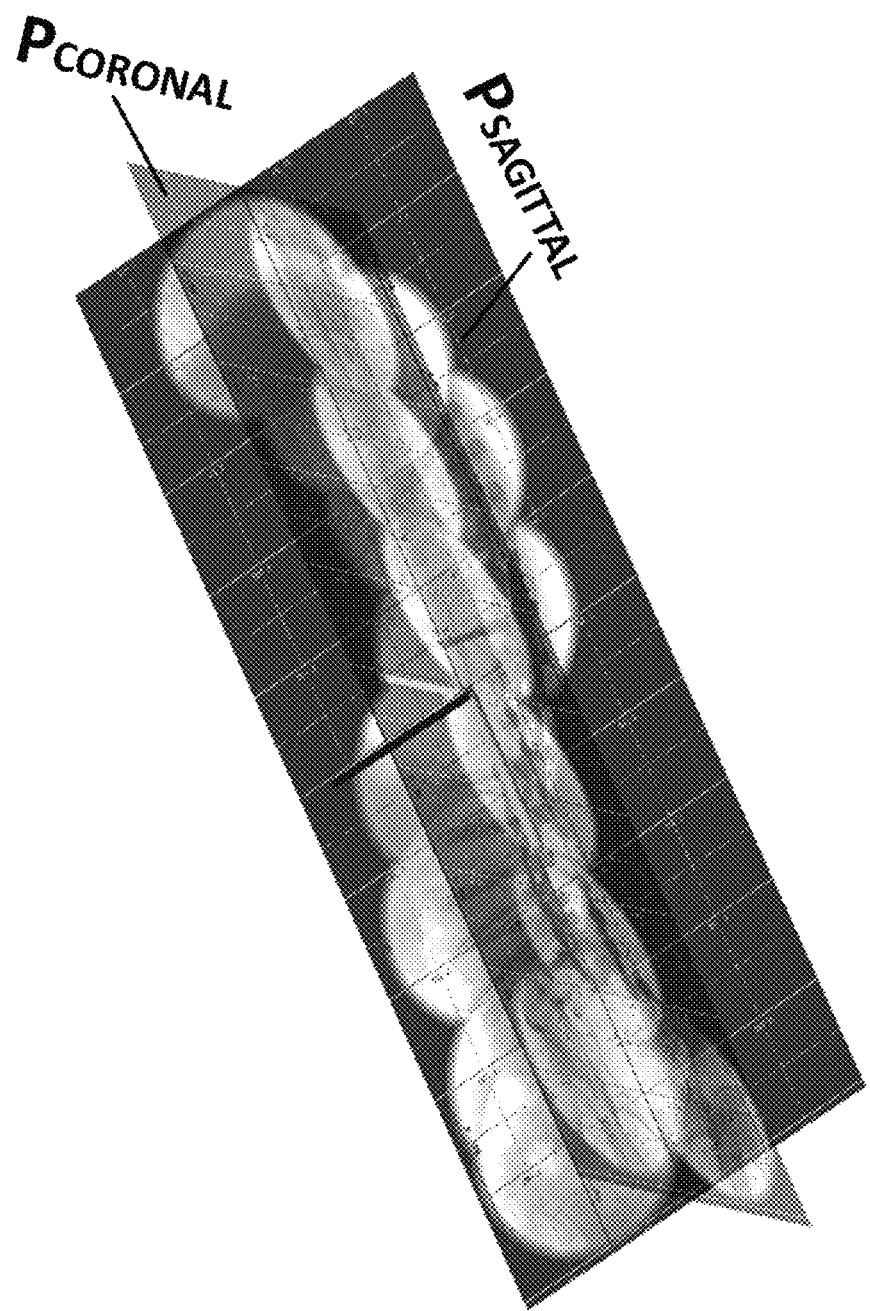
FIG. 8B illustrates sample images from the system displaying the long stereo sagittal and coronal views of the spinal anatomy overlaid with corresponding grid information in three dimensions.

FIG. 8B is a real-life example of long Coronal and Sagittal view of the pelvis and spinal anatomy. Note the matching origin and directional vectors that spatially place these views with respect to each other in three-dimensions. Each view is overlaid with the corresponding measurement grid with millimeter units. A surgeon can make direct 2D or 3D evaluation of the anatomy while the patient remains stationary on the surgical table.

Figure 18A:
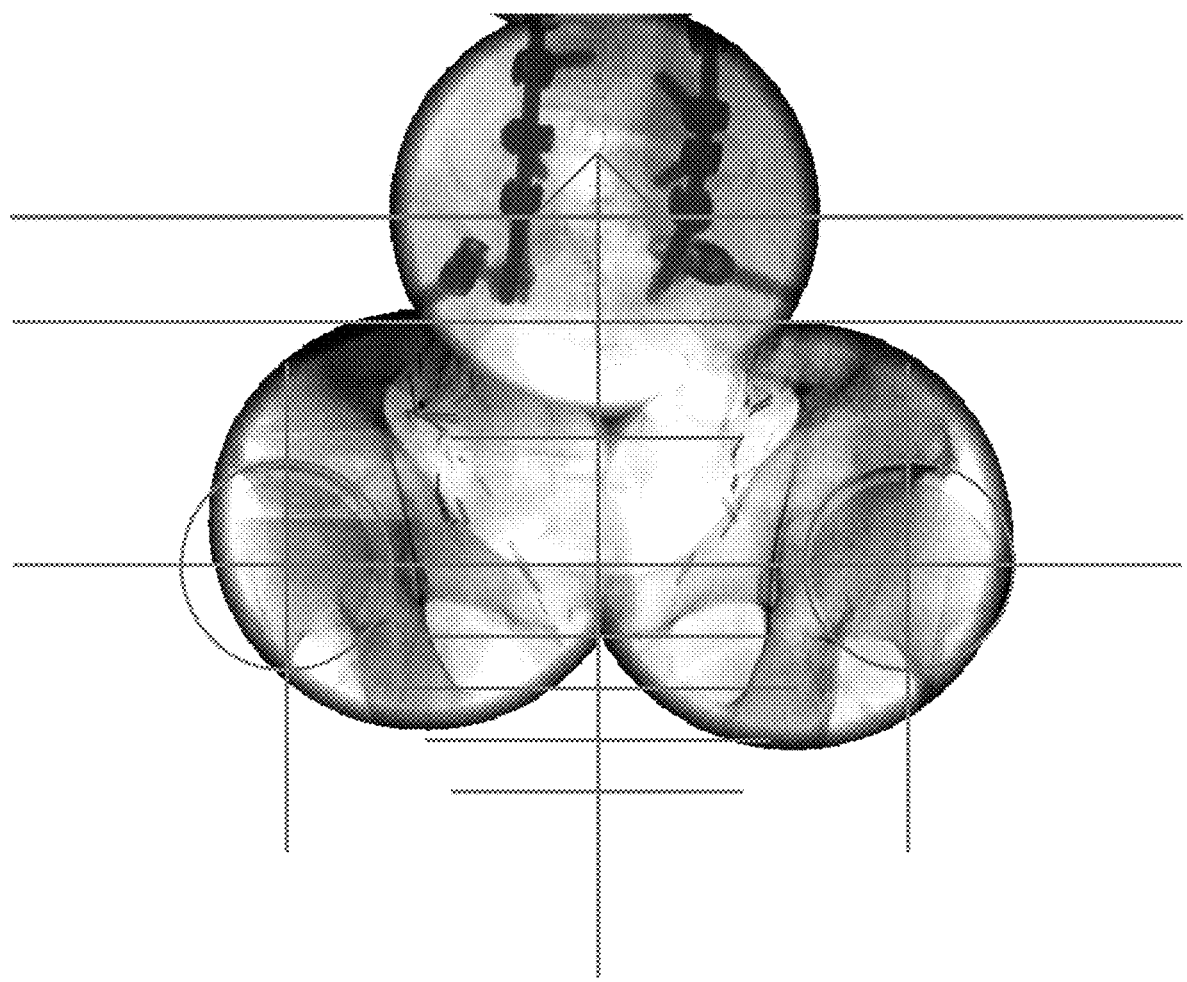
FIG. 18A is a view showing an example template superposed on a stitched image of the coronal view of a patient's pelvis. The template may be applied, for example, to correct the medio-lateral and superior-inferior direction of the pelvis. Templates may be moved, rotated and/or scaled in X and/or Y directions to match the radiographic view. The orientation of the template may be applied to correct the estimated positions and orientations of the anatomical planes.

FIG. 18A shows another example template. The template includes targets to be aligned with a patient's hip bones and a first line extending perpendicular to the mid-point of a second line joining the targets. The template lies in the coronal plane and the intersection of the first and second lines is at an origin of the template. The views of the patients anatomy and the stitched view may be created during surgery. The template allows registered orientations of the medio-lateral and superior-inferior directions of the pelvis to be corrected. This template can be moved, rotated and scaled in X and Y directions to match the radiographic views at any point during the surgery. The orientation of the template will then be processed to correct the estimated positions and orientations of the anatomical planes of the patient.

To allow use of the template of FIG. 18A the system may perform the following steps: The template can be placed over the composite of images on the coronal plane based on the tracking information available from initialization of the anatomical planes. The user can further move and manipulate the template size, position, and orientation through the graphical user interface to refine its initial placement.

Figure 18B:
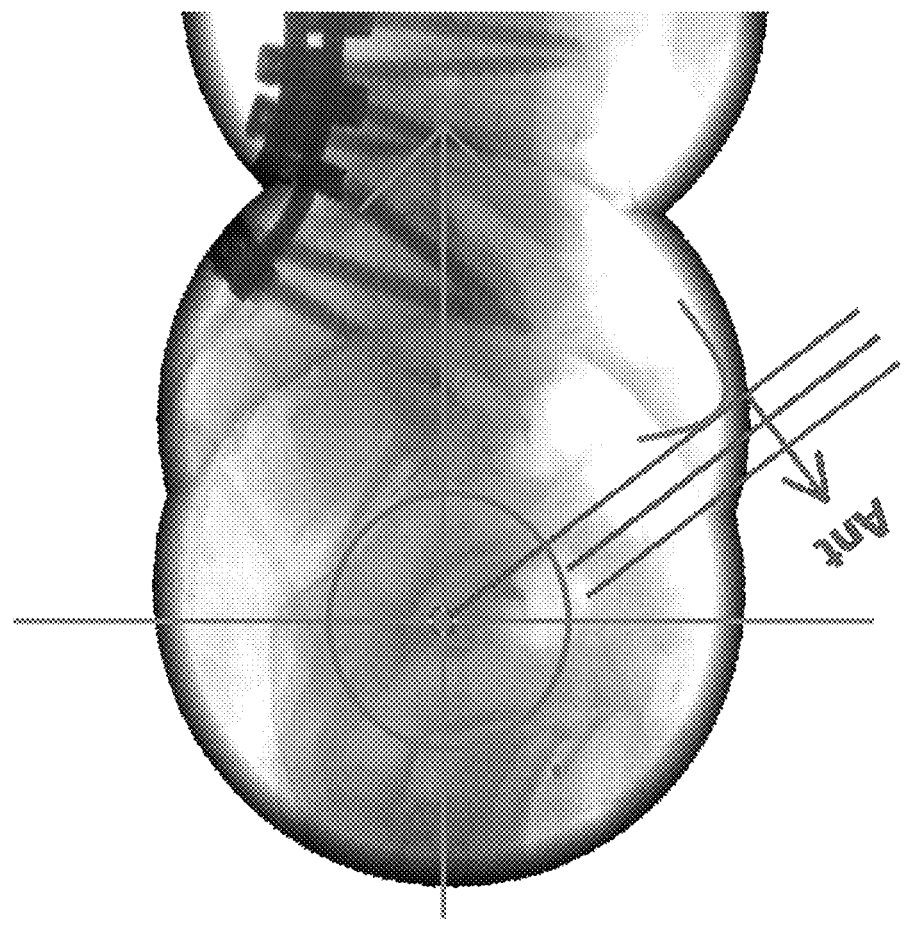
FIG. 18B is a view showing an example template superposed on a stitched image of the sagittal view of a patient's pelvis

FIG. 18B shows a similar example of a template superposed on an image in the sagittal plane. The origin of the template matches the origin of the sagittal anatomical plane, and the proximo-distal direction passes through the midpoint of the superior plate of the S1 level of the vertebral column. The views of the patients anatomy and the stitched view may be created during surgery. The template allows correcting the medio-lateral and superior-inferior direction of the pelvis. This template can be moved, rotated and scaled in X and Y directions to match the radiographic view. An auxiliary marker points to the superior iliac spine landmark. This auxiliary marker may be useful, for example, in cases where the main landmark is not visible with clarity of is occluded by surgical hardware. The orientation of the template may be processed to correct the estimated positions and orientations of the anatomical planes of the patient.

Additional lines on the template in FIG. 18B point to another auxiliary boney land mark, the anterior superior iliac spine. These additional lines can assist with defining the orientation of the template in cases where the S1 level is not fully discernible. The template can be used for measuring the vertical alignment of the spinal column at superior levels with reference of the pelvic coordinate system established by the template. Similar to the Coronal plane (FIG. 18A), the user can manipulate the position and orientation of the template to fine tune its position and correct for any apparent error in the initial estimation of its position and orientation.

In some embodiments, alignment of a template may be used to make corrections to the calculated positions of the anatomical planes. For example, the alignment of the template of FIG. 18A and FIG. 18B involves the user precisely locating the template relative to an image of the patient's hips. If a vector between the identified locations of the patient's hips deviates from the previously-calculated location of the coronal plane then the locations of the anatomical planes may be corrected by applying a suitable transformation (rotation and/or displacement).

In some embodiments, the templates placed on the coronal and sagittal anatomical planes can be positioned and moved in coordination. For instance, both templates shown in the example of FIG. 18A and FIG. 18B can share the same coordinate in the superior-inferior direction of the anatomy. Since in a typical coronal view of the pelvis on the operating table the X-ray projections of the hips are far clearer than those on the sagittal view, using both of the views in conjunction can help more accurate placement of the template on the sagittal plane. Furthermore, for this example the rotation of the template on the sagittal view can determine how the coronal template needs to be scaled in the superior-inferior direction to account for the pelvic tilt of the patient on the surgical table.

In the example of FIG. 18B, the template can be used to correct certain component of position or orientation of the anatomical references that span beyond the field of view of conventional fluoroscopy, and therefore can be prone to inaccuracy in the initial step of estimation of anatomical planes. In this example, the centre of the hip joints, the centre of the S1 superior plate, as well as the superior iliac crest can be all visualized in one large composite image, and therefore can be used for accounting for the amount of pelvic tilt in estimating the correct position of the anatomical planes.

Figure 19:
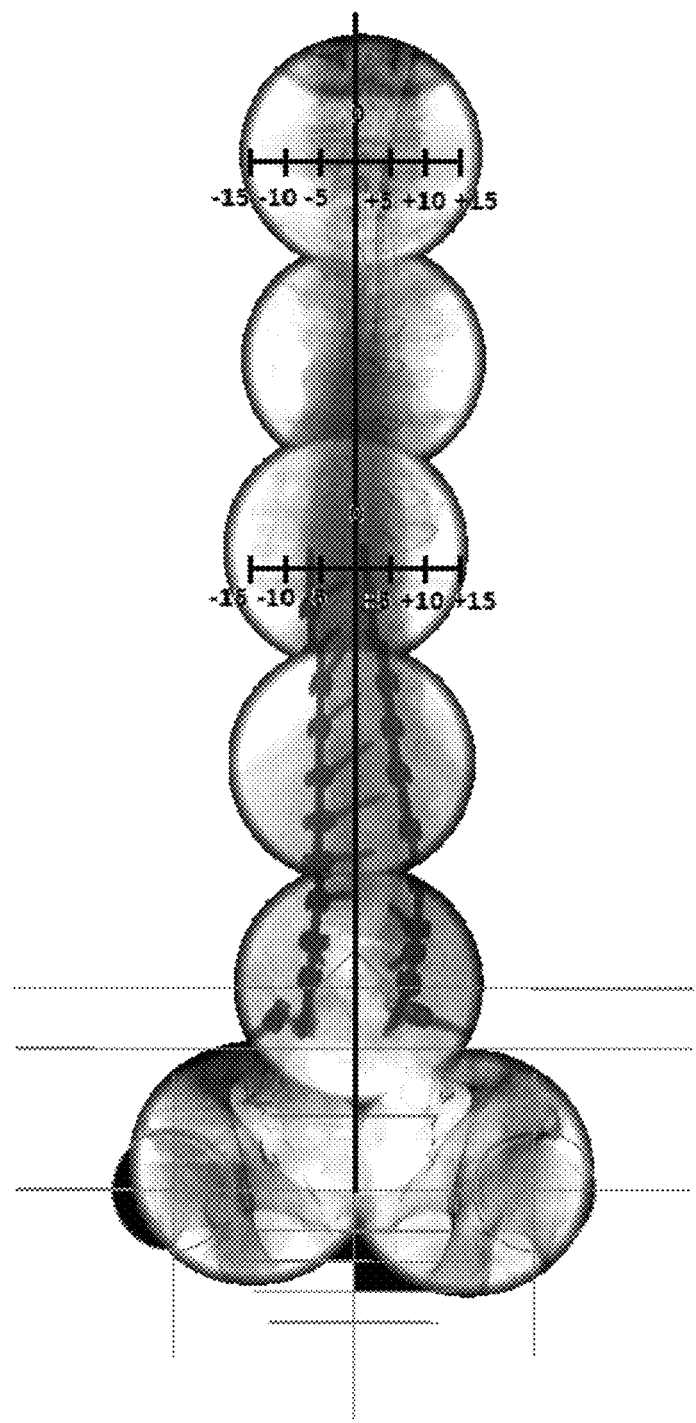
FIG. 19 is a view showing an example template superposed on a stitched view of a patient's spine.

FIG. 19 shows another example where an elongated template is placed on the coronal plane for quick assessment of distance deviations of the spinal column from the vertical reference line of the pelvis. The template placed on the coronal view allows marking the vertical reference line of the pelvis. The template may include one or more local rulers which enable reading the local deviation of the anatomy from the planned position (coronal alignment).

Figure 20:
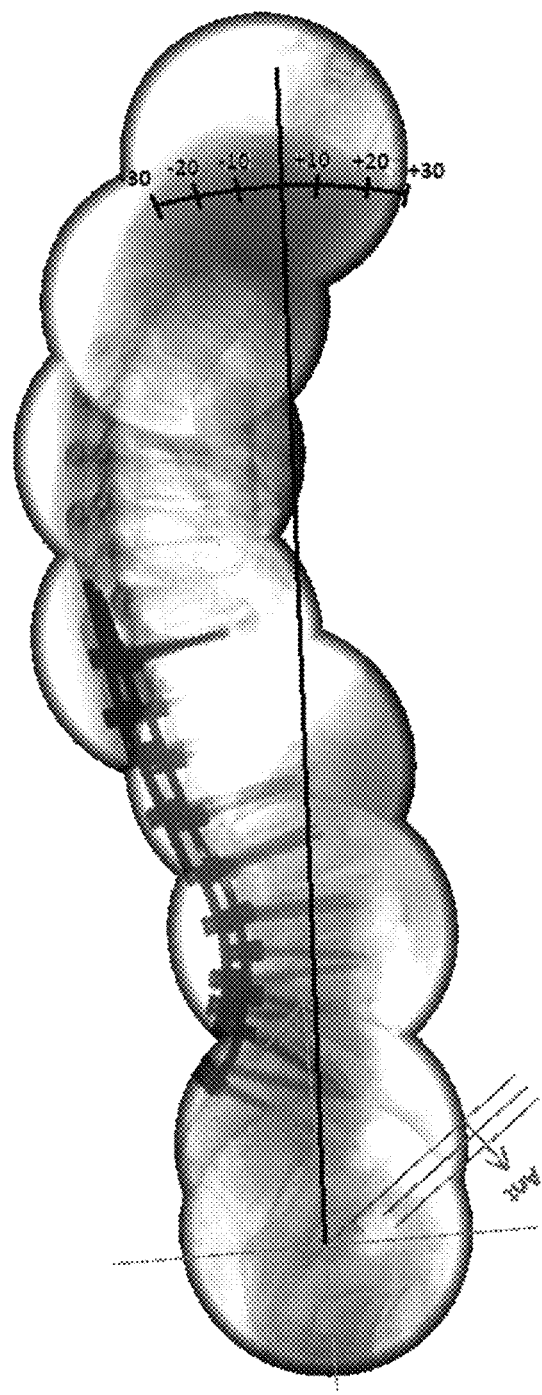
FIG. 20 is a view showing an example template superposed on a stitched view of the spine.

FIG. 20 shows another example where a large template is superposed on an image or the patient's anatomy in sagittal plane. The template facilitates quick assessment of the T1-pelvic angle of the spine during spinal fusion surgery. The template placed on the sagittal view allows marking the vertical reference line of the pelvis. The template may include one or more local protractors which enable reading the deviation of the supper spine from the pelvic reference in real time (sagittal alignment).

In some embodiments a set of two or more templates are provided. Each of the templates may correspond to different views. Depending on the current view (as determined by the tracking system) a different one of the templates may be superposed on a live image according to the predicted type of measurement that would be necessary for that position of the anatomy. These set of templates can be customized according to the type of procedure and displayed at the right place and time so the surgeon can more accurately and conveniently read and interpret the intraoperative image. Depending on the type of the surgical procedure, the placement, orientation and scaling of these templates can vary depending on the position of the imaging system with regards to the anatomical planes of the patient. One example is for checking the alignments of various parts of the trunk during spinal deformity correction. In this example, if the image intensifier of the X-ray imaging equipment is located over the shoulder blade of the patient, the system can automatically display a protractor with its zero reference aligned with the horizontal medio-lateral direction to allow quick evaluation of the obliquity of the shoulder lines. When the image intensifier is centred on the spine, the template can be automatically switched to a ruler with its origin centred vertically with the vertical reference of the body on the coronal plane to allow for distance deviation measurements from the central reference line. Another example is for the same spinal deformity correction but on the sagittal plane: when the image intensifier is pointed to the lumbar region of the spine, the template can be automatically switched to a protractor with its zero reference marking an orientation parallel to the superior plate of the S1 level of the spinal column; this would allow making quick measurements of lumbar lordosis; when the image intensifier is moved toward the thoracic spine, the protractor can be switched to the type proper for measuring the T1-pelvic angle with its zero reference line pointed to the corresponding references on the pelvic anatomy.

Figure 21A:
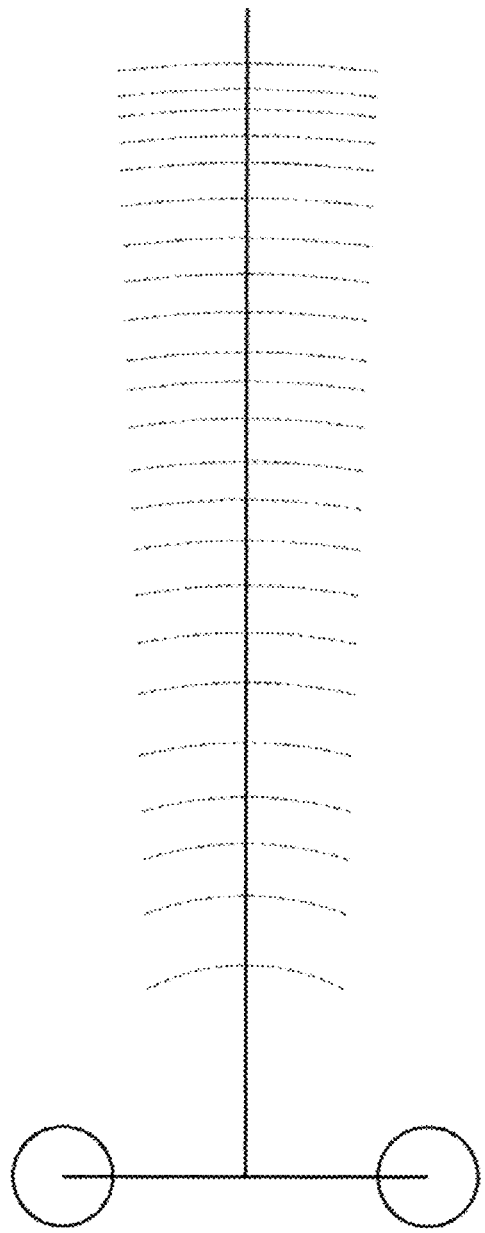
FIG. 21A shows an example coronal template customized according to the preoperative image information of the patient.
Figure 21B:
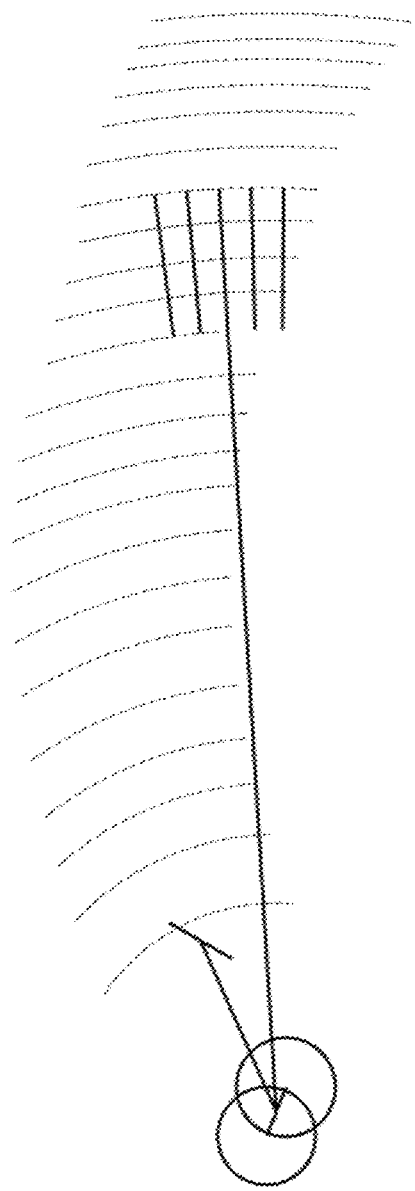
FIG. 21B shows an example sagittal template customized according to the preoperative image information of the patient.

FIGS. 21A and 21B show other example templates which apart from the features described previously define a plurality of nested spheres that are concentric about an origin point. Once a desired position for the origin has been indicated (e.g. through the initial estimation of the anatomical planes, or by a user selecting a point on a long view using a suitable interface device) the template may be displayed as a set of circles or arcs where the spheres of the template intersect with the plane of the current image. This template may be useful for functions such as counting vertebrae.

In FIGS. 21A and 21B the dashed arcs are computed automatically according to the position and orientation of the anatomical plane and displayed as a part of the template. These arcs can be annotated with the true Euclidean distances from an origin point. In the examples of FIGS. 21A and 21B, the origin of the spherical marks is located at the mi-point between the two femoral heads. In some embodiments a radial spacing between the spheres is adjustable based on user input.

In the templates of FIGS. 21A and 21B, the circular features mark the centres of the hip joints, and the horizontal arcs mark the position of various vertebrae. When matched to the intraoperative information the template can be used to localize desired levels of the spine. In the template of FIG. 21B additional protractor marks help with reading the global sagittal alignment of the spine during spinal deformity correction surgery.

Using templates such as those described above a surgeon and the surgical staff can obtain fast real-time guidance during surgery regarding the current position of the image intensifier with respect to the patient's anatomical references, as well as how well the configuration of a patient's anatomy matches a desired configuration specified by a surgical plan. Templates may be provided, for example, to assess:
- Whether a patient's spine is aligned perpendicularly to the patient's pelvis;
- Whether the acetabular cup for a hip replacement is oriented in a planned direction relative to a patient's pelvis;
- Whether parts of a broken bone (e.g. a broken tibia) are properly aligned in various anatomical planes to one another;
- Whether the shape of the fractured anatomy, restores the same morphological shapes and dimensions of the matching non-operative side;
- Whether the hip, knee, and ankle are in the desire morphological angular and distance relationship according to the plan in lower limb reconstruction surgeries;
- Whether the orientation of the reconstruction acetabulum is in correct place and orientation after periacetabular osteotomy surgery;
- Whether the lengths of a patient's legs are matched during a hip surgery or placement of artificial joints;
- Whether the joint line is restored correctly in knee replacement surgery;
- Whether the Glenoid component is placed according to the plan in total shoulder arthroplasty;
- Whether tunnel placement has been done according to the surgical plan in anterior-cruciate ligament reconstruction surgery;

Co-Registered Pre-Operative Images

As described above, pre-operative image data such as data from a pre-operative X-ray, CT scan or MRI may be co-registered in a coordinate system of the tracking system once the accurate anatomical planes of the patient have been determined as described herein. Once this has been done the X-ray machine may be navigated into a position to obtain a desired radiographic view using the pre-operative image data. A screen may display pre-operative image data corresponding to a current pose of the X-ray machine in real time. The X-ray machine does not need to be emitting any X-rays during navigation. Once the X-ray machine has been positioned to obtain the desired radiographic view (as can be verified by the displayed pre-operative image data the X-ray machine may be switched to emit X-rays and to display on the screen a live view of the patient. Prior to or during live viewing the system may be controlled to display a selected template and/or annotations superposed on the live view image.

In some embodiments, pre-operative image data is processed to obtain long images corresponding to one or more of the anatomical planes and/or one or more user-defined planes and the pre-operative long images are superposed on stitched long images obtained by the X-ray machine. A system may optionally allow a user to move the pre-operative image data to obtain better co-registration between the pre-operative image data and the reference frame of the X-ray machine.

Co-registration can be done by reference to common radiographic points between the images available prior to the surgery and images acquired from the patient on the surgical table. The pre-operative image and the corresponding information can be prepared before surgery and uploaded to the system before starting the surgery. Similar to placement of templates described above, the common reference points from the operation, can be implicitly described during the process of defining the anatomical planes, or they can be determined as shown by examples of FIG. 22A and FIG. 22B by fitting a template image to the composite of images generated during the surgery. Information determined by fitting templates to pre-operative images (e.g. images as shown in FIGS. 22A and 22B may be uploaded to system a system as described herein and used to co-register the preoperative images with intraoperative information.

Figure 22A:
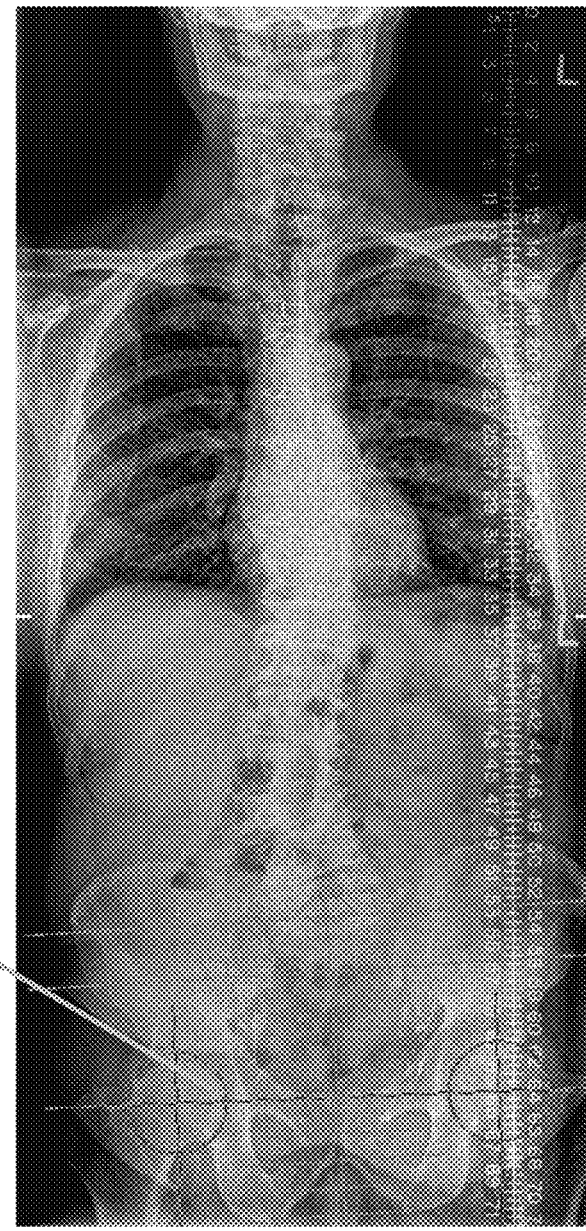
FIG. 22A shows an example template fit to the standard standing coronal scoliosis X-ray of a patient from before a surgery.
Figure 22B:
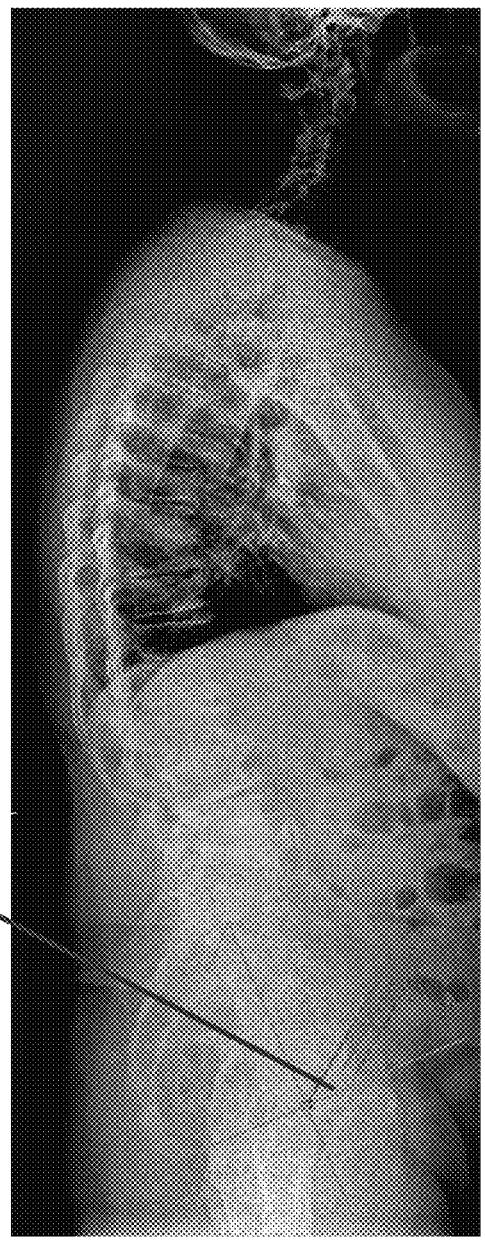
FIG. 22B shows an example template fit to the standard standing sagittal scoliosis X-ray of the patient from before the surgery.

FIGS. 22A and 22B illustrate examples of templates fitted to the X-ray images available prior to the surgery. FIGS. 18A and 18B show the same templates registered to the intraoperative information. The placement coordinates of these templates in combination may be used to determine the required transformation to be applied to the pre-operative image and data before super-imposition to the anatomical planes. In case of the examples 22A, during the process of co-registering the pre-operative images, the coronal pre-operative X-ray will be scaled differently in the superior-inferior direction by a ratio that accounts for the pelvic tilt angle.

Co-registration can be done with pre-operative images modified to simulate the desired morphological shapes of the operative anatomy. Similar to the use of templates as described above, by superimposing the pre-operative images onto the anatomical planes, quick visual comparison can be made between the anatomy of the patient on the surgical table and the simulated projection prepared as a part of the surgical plan. This image information can be accompanied with templates tools, described previously, to allow for quick evaluation of the surgical plan.

Figure 23A:
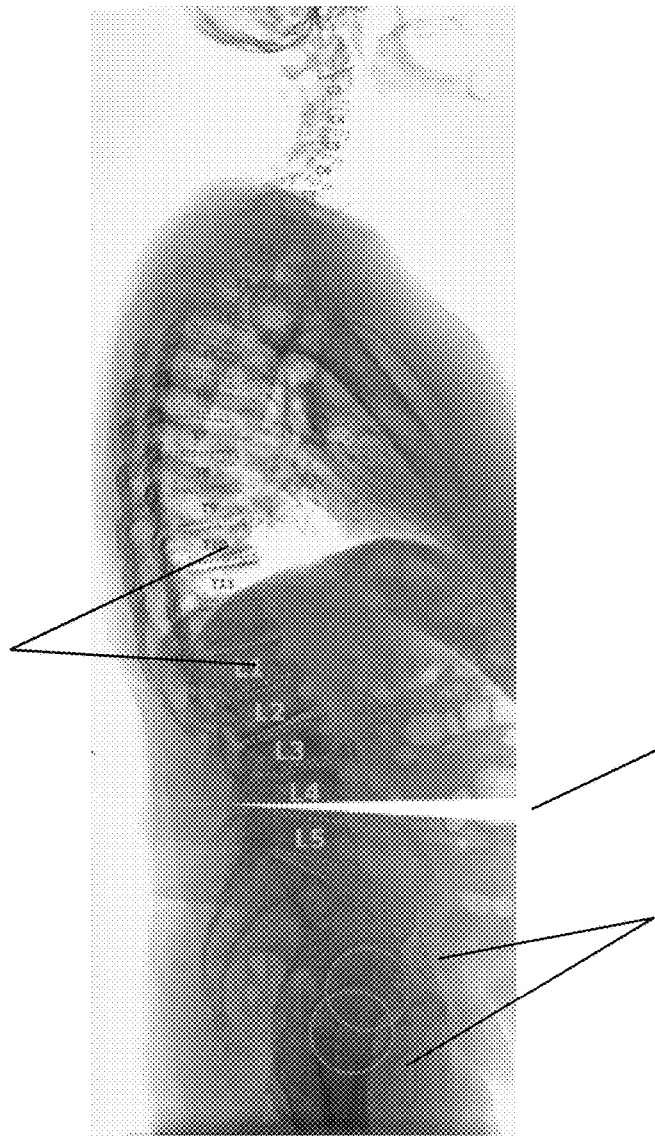
Figure 23B:
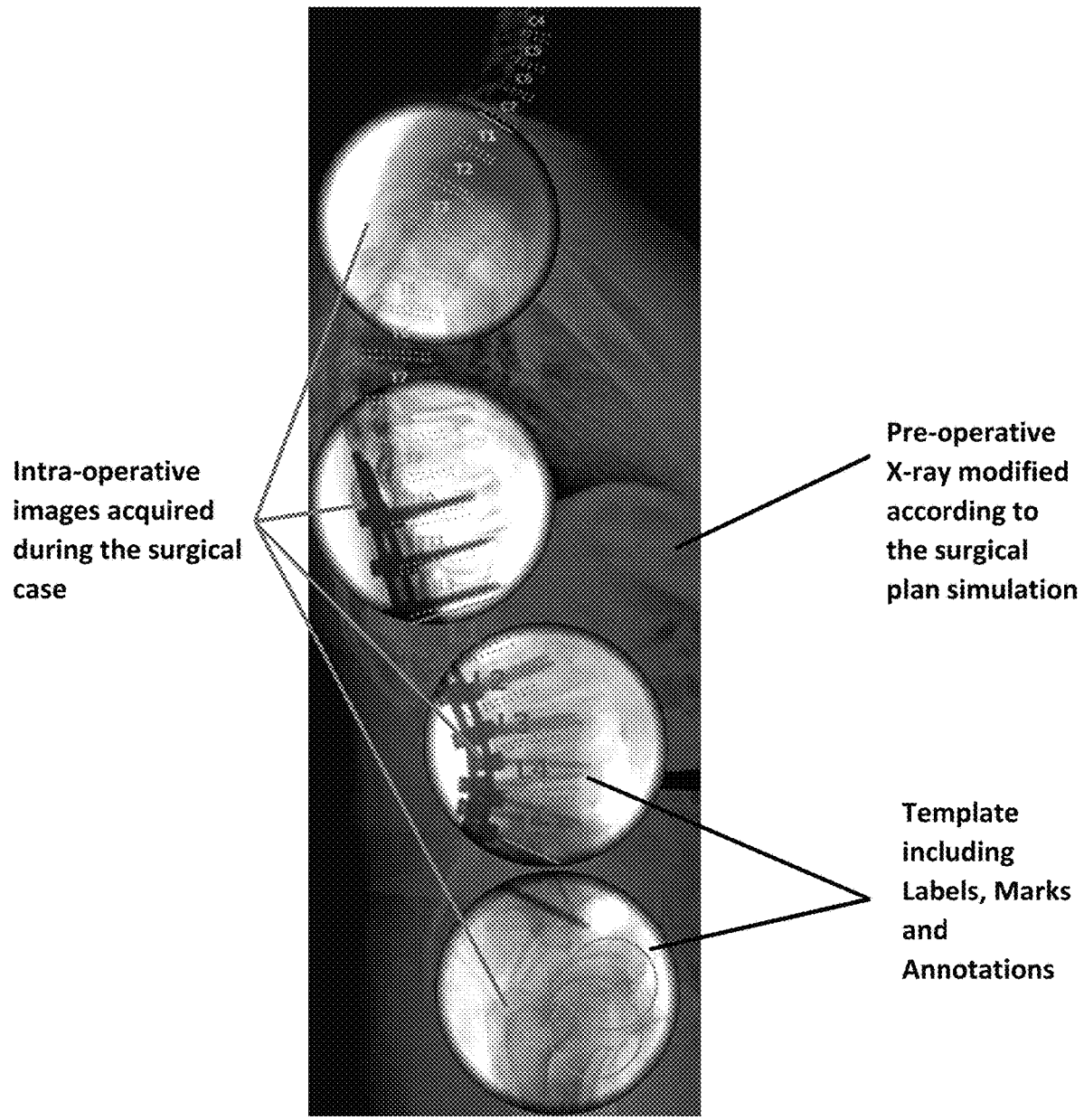
FIG. 23B is an example of preoperative image information fused with images acquired during surgery. Direct visual comparison between the intra-operative image information and the preoperative image or surgical planning can be used for real-time evaluation of the anatomical alignments in surgery.

An example is shown in FIGS. 23A and 23B. FIG. 23A shows an exported image from surgical planning software that simulates the amount of correction of the spinal anatomy and marks the vertebral levels and their plates based on full size standing X-rays of the patient. Markings indicating references and annotations as well as angular corrections may be added to the image using the surgical planning software. This information can also be exported as an image which may be uploaded to a system as described herein. The uploaded image may be co-registered with real-time imaging, based on positions of the anatomical planes of the pelvis as described herein. Now at any point during the surgery when a fluoroscopy shot is produced, as illustrated in FIG. 23B, the fluoroscopy shot can be compared directly with the underlying simulated surgical plan in the background and the surgical reference lines and the planned positions of the vertebrae as an overlay.

Templates placed over intra-operative images may be applied to facilitate correcting/refining a surgical plan. for example, in cases where the shape of the anatomy changes as the surgery progresses the templates can have adjustable shapes, and be moved, rotated, scaled, and/or warped manually, semi-automatically, or fully automatically according to the image information.

Some embodiments permit a 2D or 3D surgical plan to be automatically registered into alignment with anatomical directions determined by the system. For example, the surgical plan may include one or more reference points (e.g. an origin) and one or more directions. The system may prompt the user to indicate locations of the reference point(s) after the surgical plan is imported or the reference point(s) and/or direction(s) may be included in the surgical plan in a machine-readable format that can be read by the system and/or the reference point(s) and/or direction(s) may be indicated by symbols in the surgical plan and the system may be configured to apply image processing to locate and recognize those symbols. Once the surgical plan has been registered with the anatomical directions determined by the system the surgical plan may be overlaid on the intraoperative image layer. The system may provide a user interface control that allows a user to cause the surgical plan to be selectively displayed or not displayed.

In some embodiments a surgical plan may include different plans for plural stages of an operation. The system may import the plural surgical plans, register each of those plans as above and selectively display the plans (e.g. as overlays) in response to user commands.

The surgeon or the surgical staff may interact with template information using any suitable user interface means. The user interface means may include one or more of: a keyboard, touch pad, track pad, mouse, trackball, joystick, directional cursor navigation controls, touch screen, non-contact position-sensitive screen, gesture sensors, voice recognition, remote control buttons, cameras, or the like. Advantageously, control over at least some functions such as positioning templates is provided in some embodiments by non-contact sensors that operating room staff can use to interact with the system without need for un-scrubbing and therefore allowing iterative use of the system for real time feedback. Custom templates and the interface may be designed to facilitate this part of the process.

Co-registration may need to be re-established during a surgery if the patient or anatomy moves. Before each evaluation episode, confirmatory images may be taken of reference landmarks. The confirmatory images may be used to verify accurate co-registration, detect movements and, if necessary to re-establish proper co-registration.

In some embodiments, radio-opaque fiduciary reference markers or optical references are fixed to a patient's bones at selected sites. By reading the positions of the references with respect to the tracking space at any desired time, the locations and orientations of the anatomical planes may be adjusted. Subsequent transformations of pre-operative images and surgical plan data may then be performed by the system automatically.

Three-Dimensional Reconstructions:

A region of interest of the anatomy may be reconstructed in three dimensions by comparing locations of the same features in two known planes (for example, two different anatomical planes). It is convenient for the planes to be orthogonal or near orthogonal to one another. Determining locations of features may be done in various ways or combinations of these ways. In some embodiments locations of features such as the centers of vertebrae or other bones are determined by receiving user input. In some embodiments the locations of the features are determined by image processing algorithms. In some embodiments a combination of user inputs and image processing algorithms is used to determine locations of the features in each of plural views.

In an example embodiment, apparatus is configured to ask the user to mark areas corresponding to features depicted in each of two preliminary long views through the graphical user interface. For example, the user may be instructed to trace along the center of the patient's spine as depicted in each of a sagittal and a coronal long view. This may be done, for example using a finger on a touch screen or using a pointing device such as an electronic stylus or mouse or trackball.

In another example embodiment the features of the anatomy are approximated by processing each of the images to identify structures (e.g. images of vertebrae, other bones or fiducial markers) and computing the 2D location of a center point or centroid of each of the structures or computing the trajectory of a line passing centrally along an elongated structure such as the spine. Identification of structures may be performed by image segmentation such as edge detection and may be guided by the fact that the general appearance of such structures is known. For example, the system may include a model representing the expected appearance of a vertebra. The model may be a general model or a model specific to the patient may be created from preoperative image data.

Other example embodiments apply user input to guide machine identification of structures and/or apply machine vision technology to refine user input identifying structures. For example, the system may receive user input identifying one or more structures and then perform image analysis to do one or more of: refining the position of the identified structures and locating other structures based on locations of the identified structures. Refining position of a structure may be determined, for example, by determining a center of the structure based at least in part on locations of edges of the structure and/or by fitting a model of the structure to the structure. An example of locating other structures is that the system may request that the user mark centers of selected vertebrae and the system may then automatically identify other vertebrae based on the locations of the vertebrae identified by the user.

As another example, the system may process images to locate one or more structures and then allow locations of the located structures to be refined based on user inputs.

As another example, the system may assume that the additional images will be centered on an anatomical structure of interest or that a cross hair or other target in a live view (where the target could be but is not necessarily centered in the live view image) be aligned with the anatomy of interest. For example, where an operation is being performed on a user's spine the system may assume that the images of a set of images will be centered on the patient's spine. This assumption may be reinforced by configuring the system to instruct the user to center the field of view of a set of images on the anatomical structure of interest, here the patient's spine. The system may then determine a 3D geometry of the spine relative to the anatomical planes by determining the 2D locations in the long views corresponding to the centers of the images of the set of images. The set of images may be acquired while viewing an output of the x-ray machine in a live view mode which displays a crosshair, circles or other indicia to indicate the center of the field of view. This allows a user to position the x-ray machine such that the spine or other anatomy of interest coincides with the center of the field of view and then trigger acquisition of an image. Locations of the centers of the images taken at different poses of the x-ray machine may be processed to determine depth of the anatomy of interest relative to different anatomical planes and/or to determine a form of the anatomy of interest in three dimensions. This implementation is advantageous since it does not require image processing to determine points corresponding to the anatomy of interest.

2D locations of points or lines in plural views may be processed as described herein to determine positions of the corresponding structures in the patient in three dimensions.

The three-dimensional configuration so-determined is used by the system in some embodiments to refine the stitched long views and correct any remaining parallax by accounting for the local depth of anatomy for any pixel on the original projection.

Figure 12A:
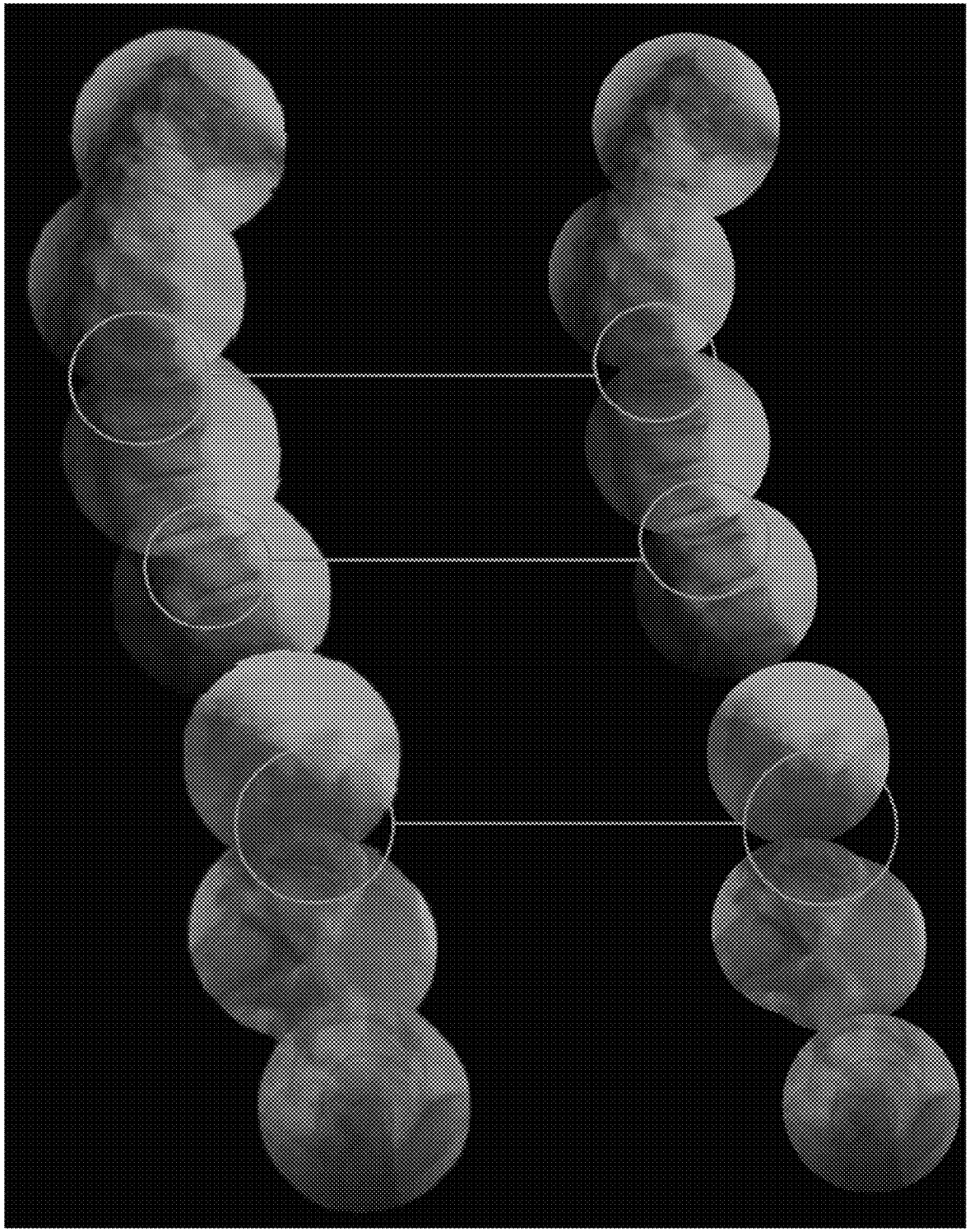
FIG. 12A is a sample image showing the sagittal view of the spinal anatomy before (Right), and after (Left) refinement based of local depth information.
Figure 12B:
FIG. 12B is a sample image showing the coronal view of the spinal anatomy before (Right), and after (Left) refinement based of local depth information.

FIGS. 12A and 12B illustrate how long images built by transforming images onto the anatomical planes may have some remaining undesirable parallax. Such parallax can arise because the geometry of the anatomy of interest in reality has a three-dimensional shape that does not fit on a flat plane. In order to remove the parallax and further refine the images, once the preliminary long views are available, the approximate longitudinal shape (or depth) or the anatomical structure relative to the reference planes may to be determined. This may be done, for example by asking the operator to identify corresponding locations in different ones of the long views.

Figure 9:
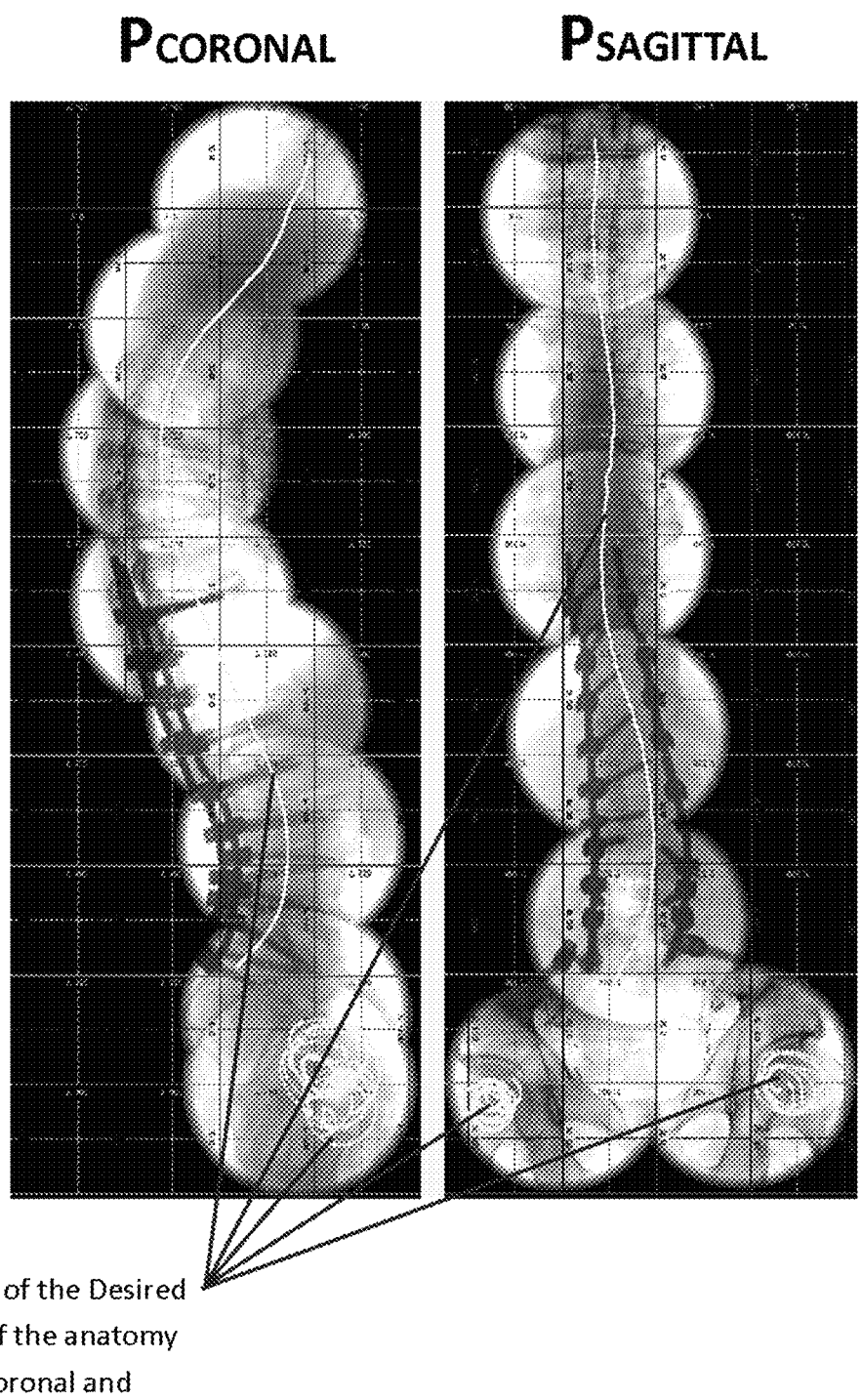
FIG. 9 illustrates an example touch-based graphical user interface which is one way that the position of desired anatomies can be marked on a stereo view. This functionality may be used to intersect projections and create the approximate shape of the anatomy along the table.

For example, the operator may use a control provided by a GUI to paint the areas of interest on stereo views. This can be done by swiping finger over a touch screen or by using a computer mouse input, for example. FIG. 9 shows the central line of the spine and the location of the two hip heads painted (segmented) by the operator (shown in dotted lines). Since the accurate spatial information of the image is available, the two-dimensional information can be used to reconstruct the shape of these selected points in three-dimensions and using these for refining the parallax as described below.

Figure 10A:
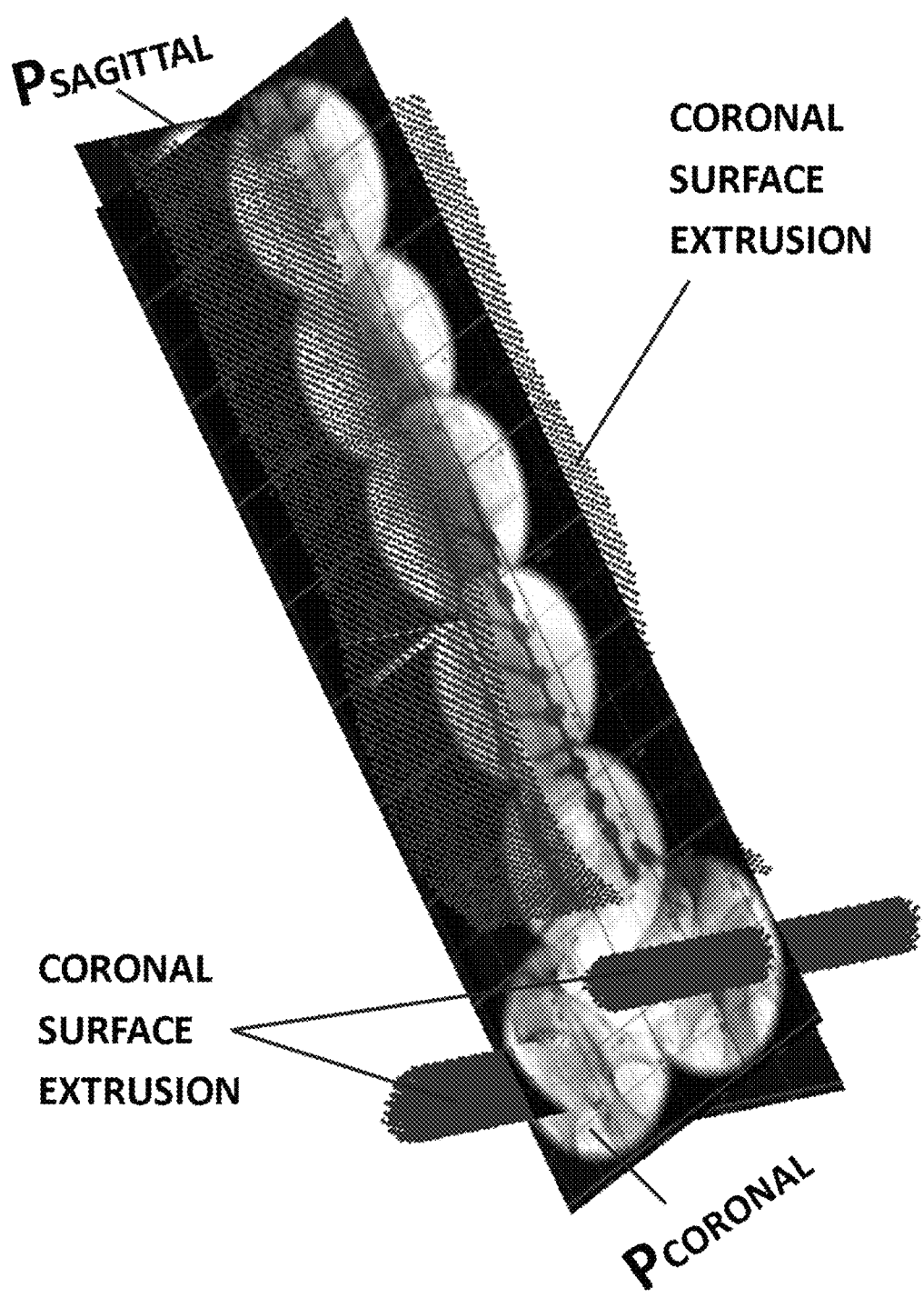
FIG. 10A is a voxel representation of the extruded surface based on one view. This example is for spinopelvic anatomy.

FIG. 10A illustrates a way to reconstruct a three-dimensional voxel representation of the digitized or painted marks (identified by dotted lines in FIG. 9). First the pixels' coordinates are extruded in a direction normal to the corresponding anatomical plane. Note that the hips in the example are disconnected from the spine, but the result is discrete volumes (shown in dash-dotted lines). Note that for the sake of illustration there are gaps between the points in the normal direction to the planes. However, the computed voxel representation in the computer code is continuous in that direction.

Figure 10B:
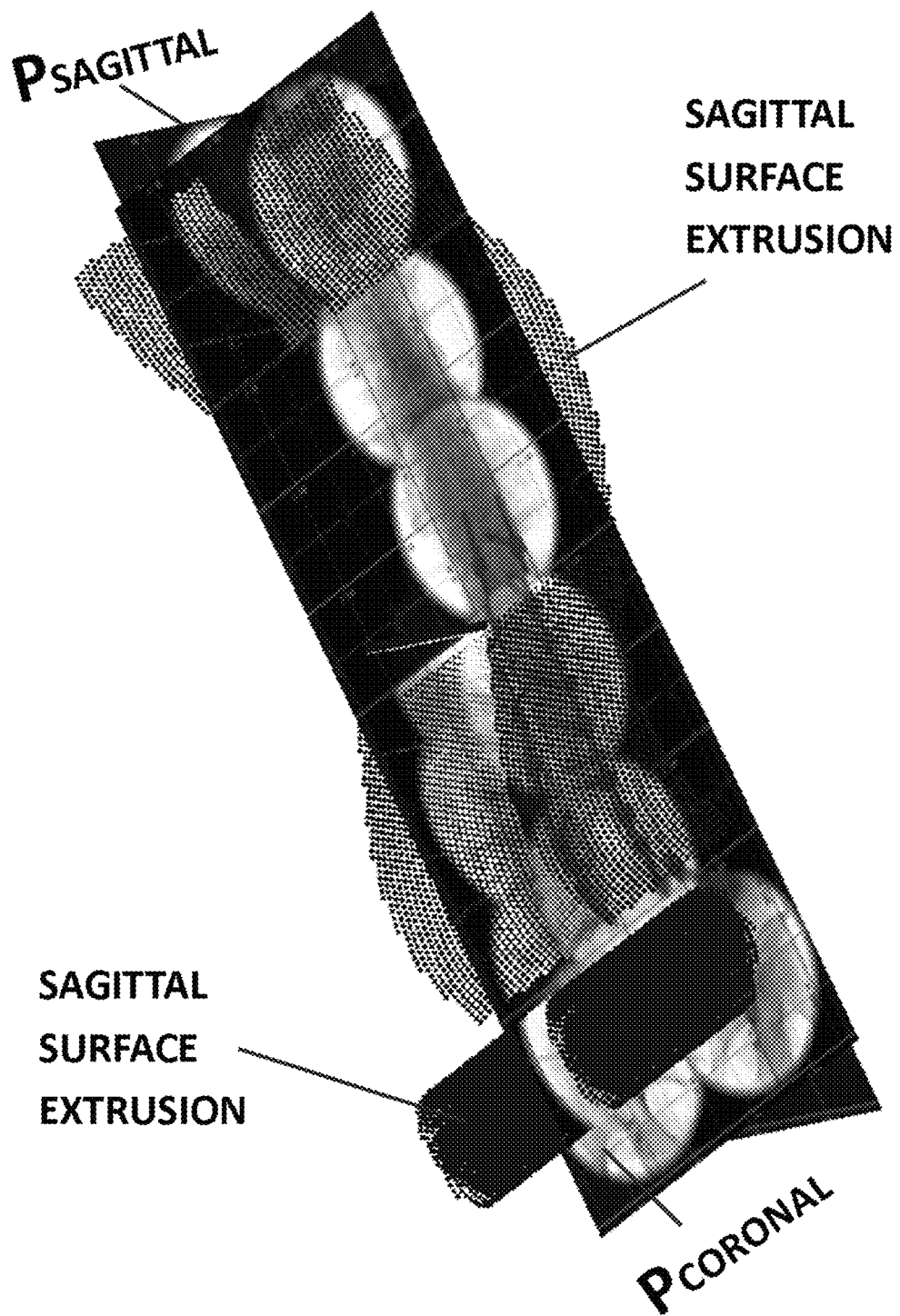
FIG. 10B is a voxel visualization of extrusion of the selected pixels on the matching radiographic view, comparable with FIG. 10A.

FIG. 10B illustrates how a similar voxel volume is created by extruding the pixel coordinates in another direction, in the illustrated case perpendicular to the normal direction to the long sagittal plane. Note that the extension is a separate voxel, but is one entity because of the hips had overlapping projections on the sagittal long view (FIG. 9—Left Image).

Figure 10C:
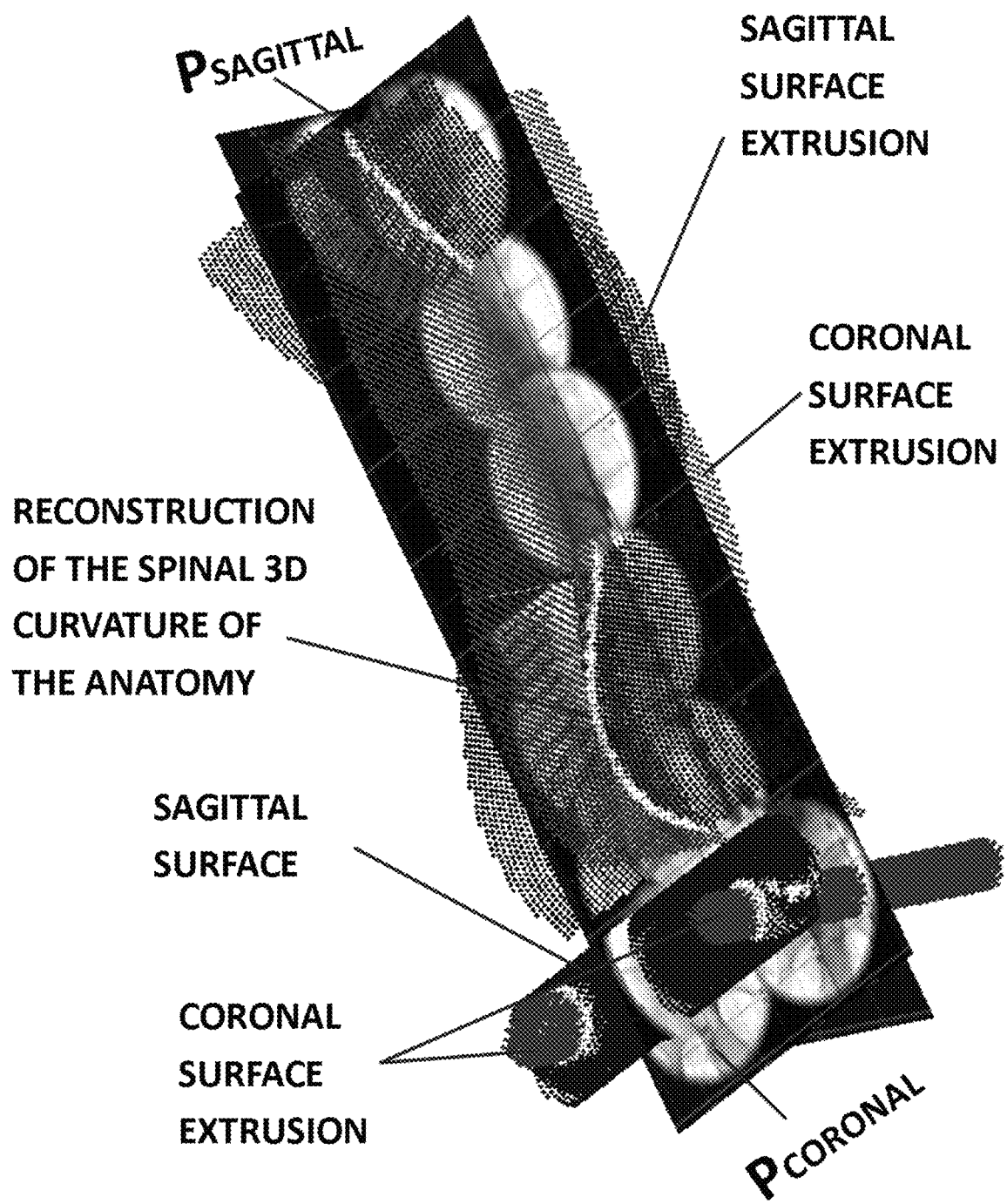
FIG. 10C shows the three-dimensional shape of the reconstructed geometries (yellow marks) from marked pixels (FIG. 9) and volume intersection between the voxel representation of the pixel extrusions in the space (FIGS. 10A and 10B).

FIG. 10C shows how the volume intersection built based on the stereo views may be computed (highlighted curves), this provides three-dimensional information of the desired portion of the anatomy. The three-dimensional information may be used by the system to automatically refine the long views.

Figure 10D:
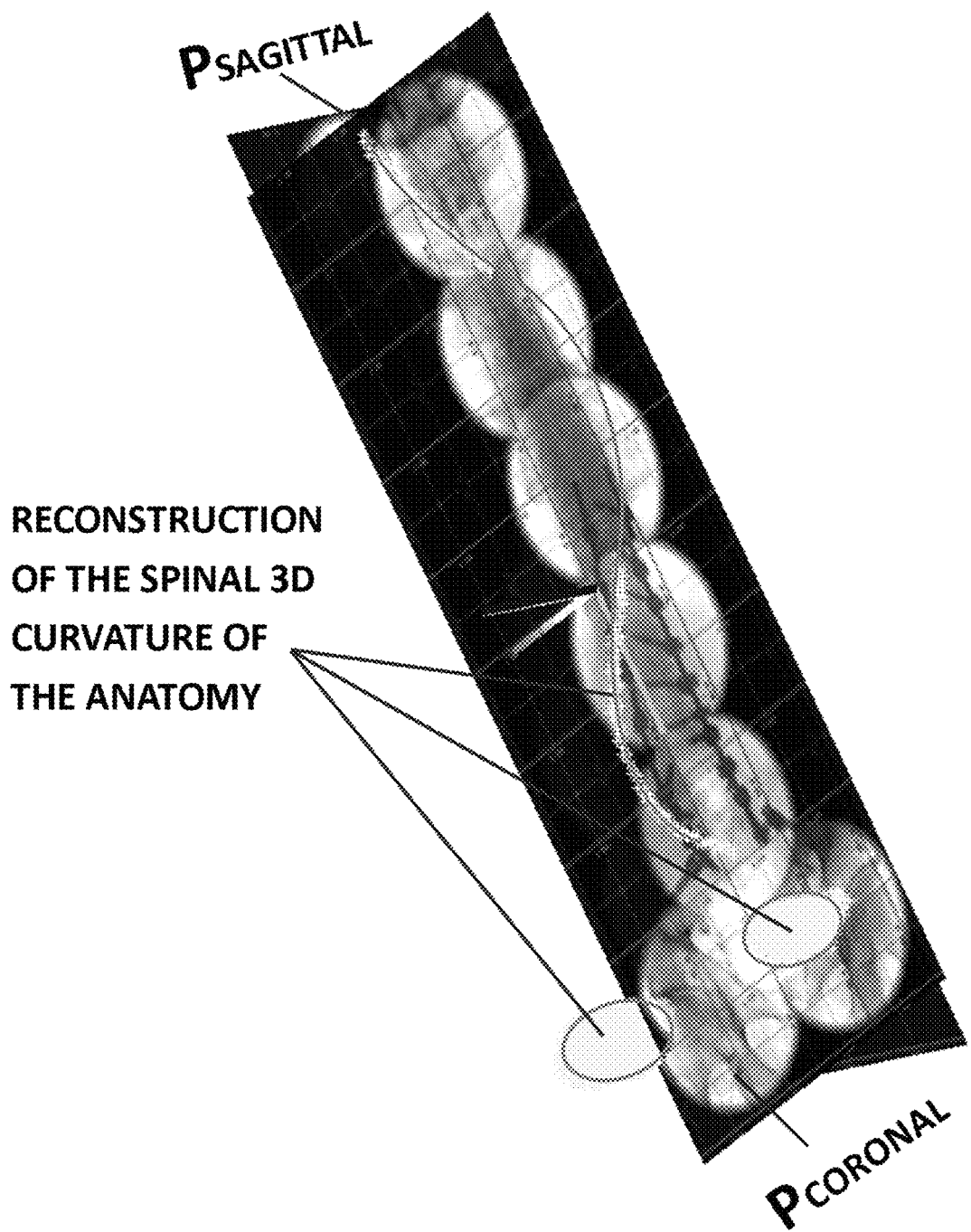
FIG. 10D is a visualization of the mark positions of the anatomy in the example spinopelvic geometry. In some areas the anatomy of interest can be at significant distance from the reference anatomical plan, and hence leave parallax artifacts on the resulted long stitch views.
Figure 11A:
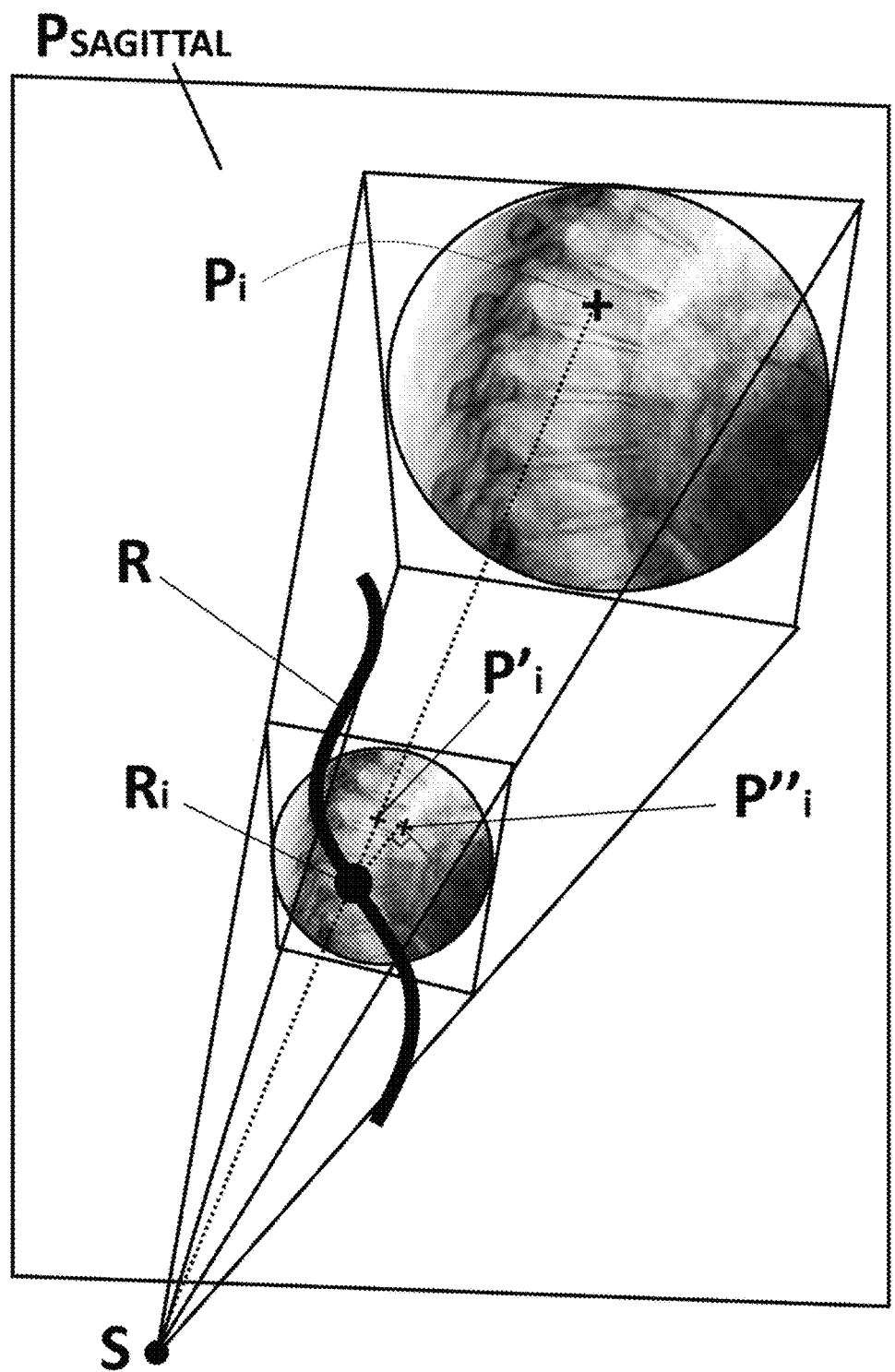
FIG. 11A illustrates how the reconstructed shape of the anatomy can be used to refine the transformed projection to reduce or eliminate parallax artifacts. The local depth information can be used to warp the transformed projections for this purpose.
Figure 11B:
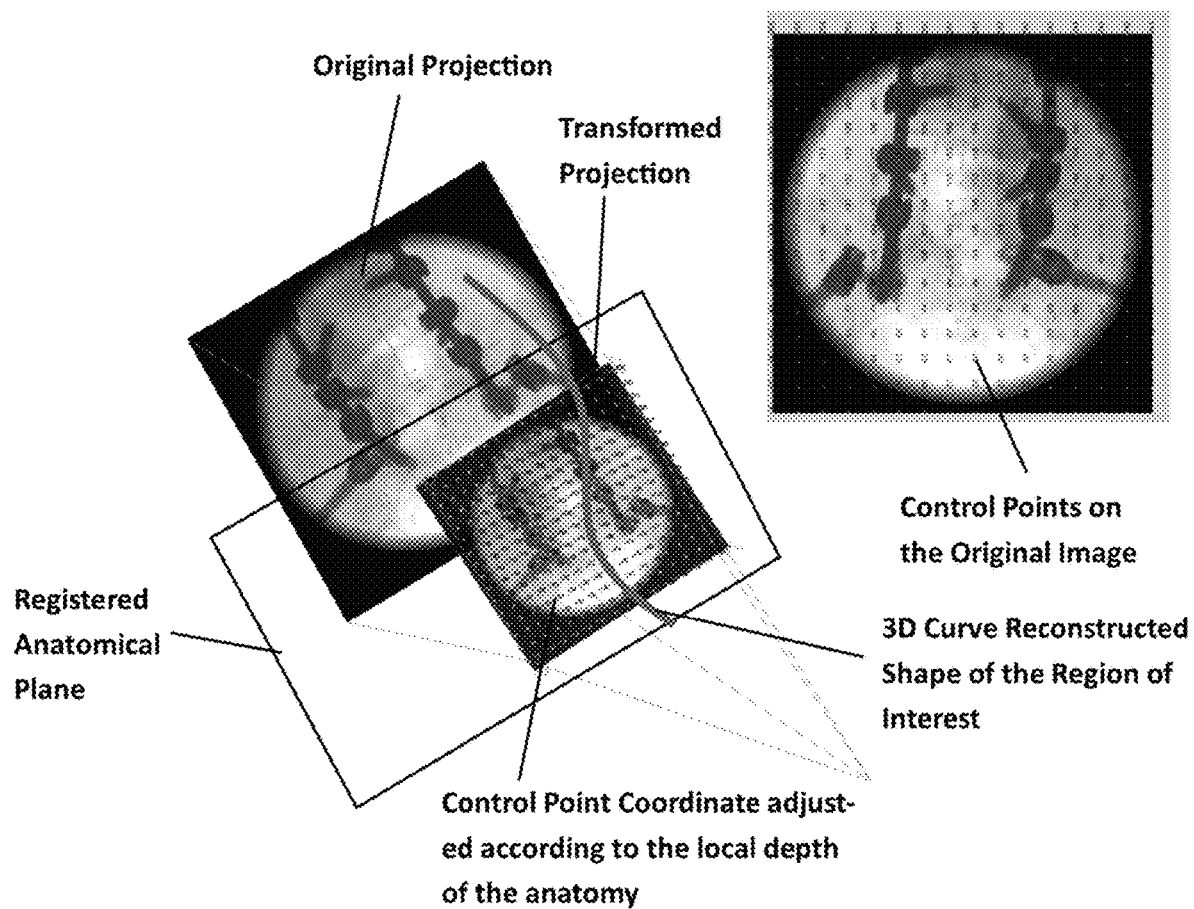
FIG. 11B illustrates a method for refining the transformed projection of each image using an array of control points that are assigned to various pixels on the original image. Their corresponding corrected coordinates on the desired anatomical plane are calculated based on the approximate depth of the local anatomy from the three-dimensional reconstruction of the region of interest.

FIG. 10D is a real-life example showing the three-dimensional shape of a patient's spine and the approximate spatial positions of the patient's the hips indicated with highlighted curves overlaid on long radiographic views of the patient's anatomy (Note the missing segment of the spine is hidden behind the radiographic plane at the shown angle). It can be seen from FIG. 10D that, the voxel representation of the anatomy is available from this process, and the system has depth information for any point along the length of the anatomy. As illustrated in FIGS. 11A and 11B, this information may be used to refine the stitched views for reformatting the long views, as well as for quick labeling of various landmarks on the image.

FIG. 11A illustrates how the depth information for the reconstructed anatomy may be used to refine a projection transformation into an anatomical plane. This is done by recalculating the coordinates of image pixels using the depth information from the reconstructed shape of the anatomy. A matrix of control points is assumed on the surface of the image. A sample of these points are shown as $P_i$ in the image, based on the initial calculation of the projection, the corresponding coordinate of the projection was first calculated as $P'_i$ found as the intersection between the line S-$P_i$ connecting the corresponding location of the X-ray source S and the projection $P_i$. The three-dimensional reconstructed shape of the anatomy R can be used to correct the pixel coordinates in the plane into which the image is being transformed based on the local depth of the anatomy. Analyzing the geometric proximity of R and the line S-$P_i$ passing through the projection $P'_i$, the corresponding point on the reconstructed anatomy R, or the closest point to R, can be found. This point is denoted by $R_i$ in FIG. 11A.

In this example, the corresponding point on R is at $R_i$-$P'_i$ distance from the corresponding depth and therefore the corresponding projection can be corrected. The coordinate of the corrected projection $P'''_i$ is found as the intersection between the projection plane (here $P_{SAGITTAL}$) and the line passing through $R_i$ and perpendicular to the corresponding anatomical plane. The pair $P'_i$ and $P'''_i$ provides matching control points that can be used to calculate the required transformation for creating parallax-free long radiographic views. The complete transformation function can be calculated by considering a matrix of control points, similar to $P_i$ equally distributed over the original projection, and finding their corresponding coordinates on the anatomical plane based on the local depth of the anatomy for each control point as described for $P'_i$.

Note that, one can also create a surface representation of the depth of the anatomy by geometrically extruding the reconstructed curvature (R) in a direction perpendicular to the length of the patient, or in another desired orientation. The resulting surface can be used to estimate the depth of the pixels in the above described process for removing parallax.

FIG. 11B illustrates application of the method illustrated by FIG. 11A to an array of points across the original projection. Corrected coordinates corresponding to each of the points are calculated by analyzing the relationships among the three-dimensional positions of the original projection, the X-ray source, the registered anatomical plane, and the distances from the control points on the transformed projection to the corresponding or closest points on the reconstructed region of the anatomy (as illustrated by FIG. 11A). The original and target points are then used to calculate the transformation that warps the original image to the projection on the long radiographic view in a way that it removed parallax.

FIG. 12A shows a real-life example long sagittal view created from a spinal anatomy using the system before refinement of parallax based on local depth anatomy (Right), and the corresponding corrected image (Left). The circles indicate areas where parallax affects the original image and the corresponding areas of the corrected view.

FIG. 12B is a real-life example long coronal view from a pelvic and spinal anatomy. Similar to FIG. 12A, the image displays the before (Right) and after (Left) correction based on depth information. What is seen as separate images in the original image overlap with one another in the corrected projection.

Figure 13:
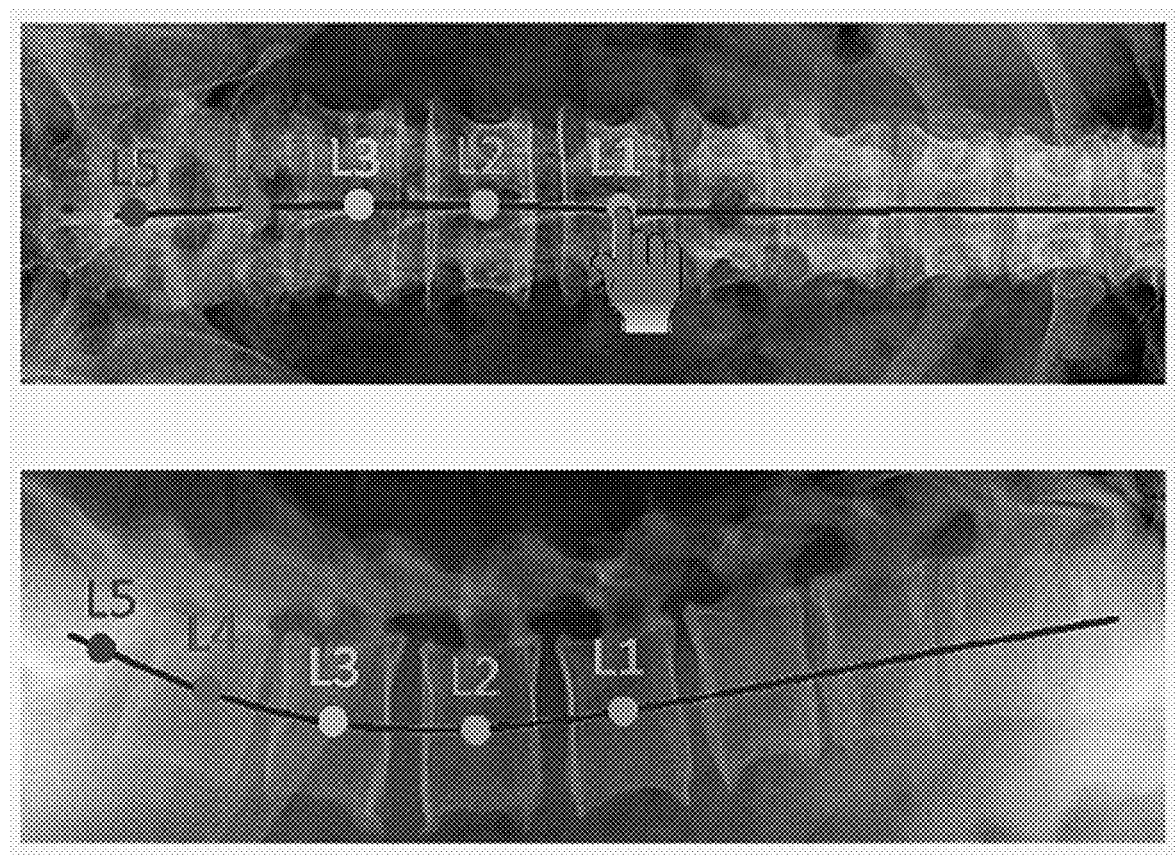
FIG. 13 illustrates a user interface feature that provides additional utility. After refinement the available information of the three-dimensional shape of the desired anatomy (e.g. shown FIG. 10D) can be used for quick localization and labeling of certain landmarks, here the lumbar vertebral levels.

FIG. 13 illustrates how the reconstructed shape of the anatomy, as illustrated for example in FIG. 10D, can also be used for quick labeling of anatomical landmarks. An operator can label the spinal levels, in this example starting from the lowest lumbar level (L5) upwards. The operator may digitize the locations of the vertebrae by clicking or tapping on one image only. The system can determine the closest matching point along the reconstructed anatomy (projection of which is shown by dark carves in the image), mark that landmark in three-dimensions and display the corresponding location on any relevant projection. In this example, for instance, as soon as the L1 level is identified on the top view being the coronal radiograph of the spine (e.g. by tapping on a touch screen of a user interface) the corresponding coordinate of the landmark is localized in three-dimensions and displaced on the corresponding sagittal projection (lower image). This provides a convenient means for quick counting of the levels while cross checking the location on the landmarks on more than one view.

In some cases an anatomical feature may not be clearly seen in one plane but may be more clearly visible in another plane. In such cases the location of the anatomical feature in another view, combined with information that describes the 3D configuration of the patient's anatomy may be used to mark the location of the feature in the first view. This may be done by configuring the system to use shape information defining a 3-dimensional shape of a structure of the patient's anatomy relative to the anatomical planes to determine a position of a feature on the structure of the patient's anatomy corresponding to a point marked on one of the long views in three dimensions using the shape information and a location of the point. The three dimensional location of the point may then be projected into the plane of the other one of the long views. For example, a particular vertebral level may need to be identified in an AP view in which the vertebral level cannot be easily identified. As a solution a lateral view can be used together with the 3D configuration of the anatomy to mark the location of this particular anatomy on the AP view.

Figure 15:
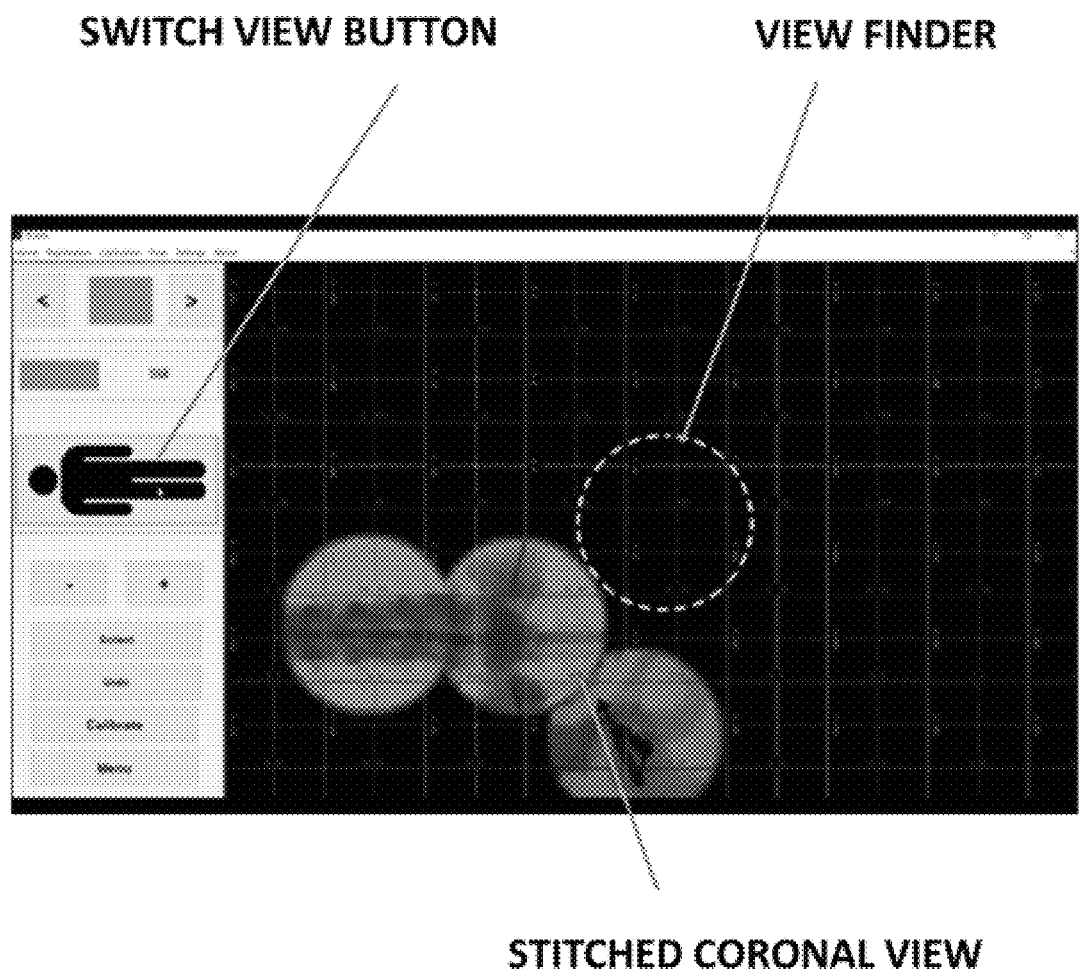
FIG. 15 shows an example graphical user interface that may be used to generate long calibrated views for real-time assessment.

FIG. 15 shows an example graphical user interface displaying a stitched view, optionally with overlaid measurement grid in real time. FIG. 15 shows the current position of the imaging equipment and position that is going to be filled with the transformed projection. This view provides useful information about the current coordinates of the anatomy along with the previously acquired projections. In this embodiment, the user can switch the desired anatomical plane (switch view button in the example interface). The system can also load calibrated radiographic images, with or without the lines and marks of a surgical plan, and overlay them on top of the existing plane for comparison or for use as a guiding map to locate desired anatomies or to check whether certain anatomical features have a desired configuration or a desired relationship to other anatomical features and/or to an anatomical plane.

Figure 16:
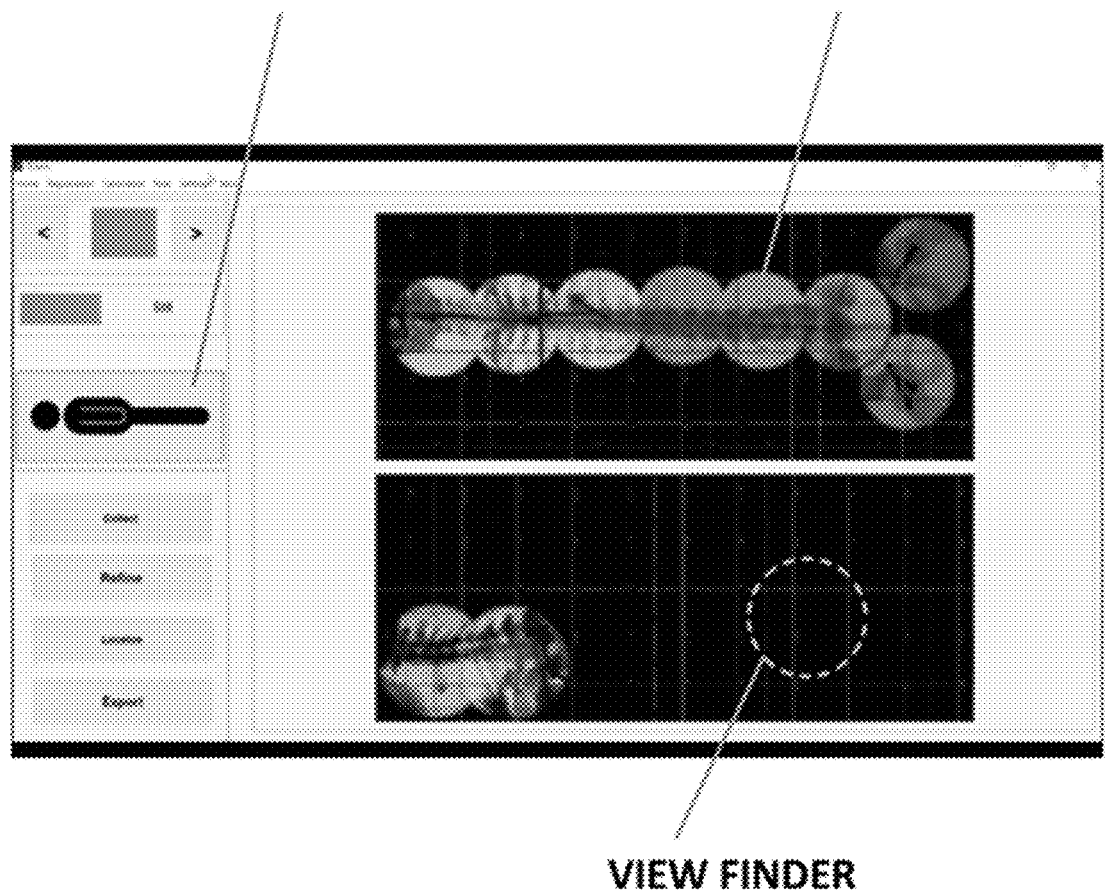
FIG. 16 shows an example graphical user interface that may be used to generate multiple calibrated views simultaneously and to conduct real-time assessments in two or three dimensions.

FIG. 16 shows an example graphical user interface that includes a display of a stereo view of the anatomy, optionally with one or more overlaid grids. The location of the viewfinder indicates (in this example with a dashed circle) the current location of the imaging equipment, to help the technical or the imaging technician have a better orientation and guidance for acquiring images. Where a surgical plan is available as bi-planar or three-dimensional drawings or models the surgical plan could optionally be overlaid on top (or below) or fused with the intraoperative images.

Figure 17:
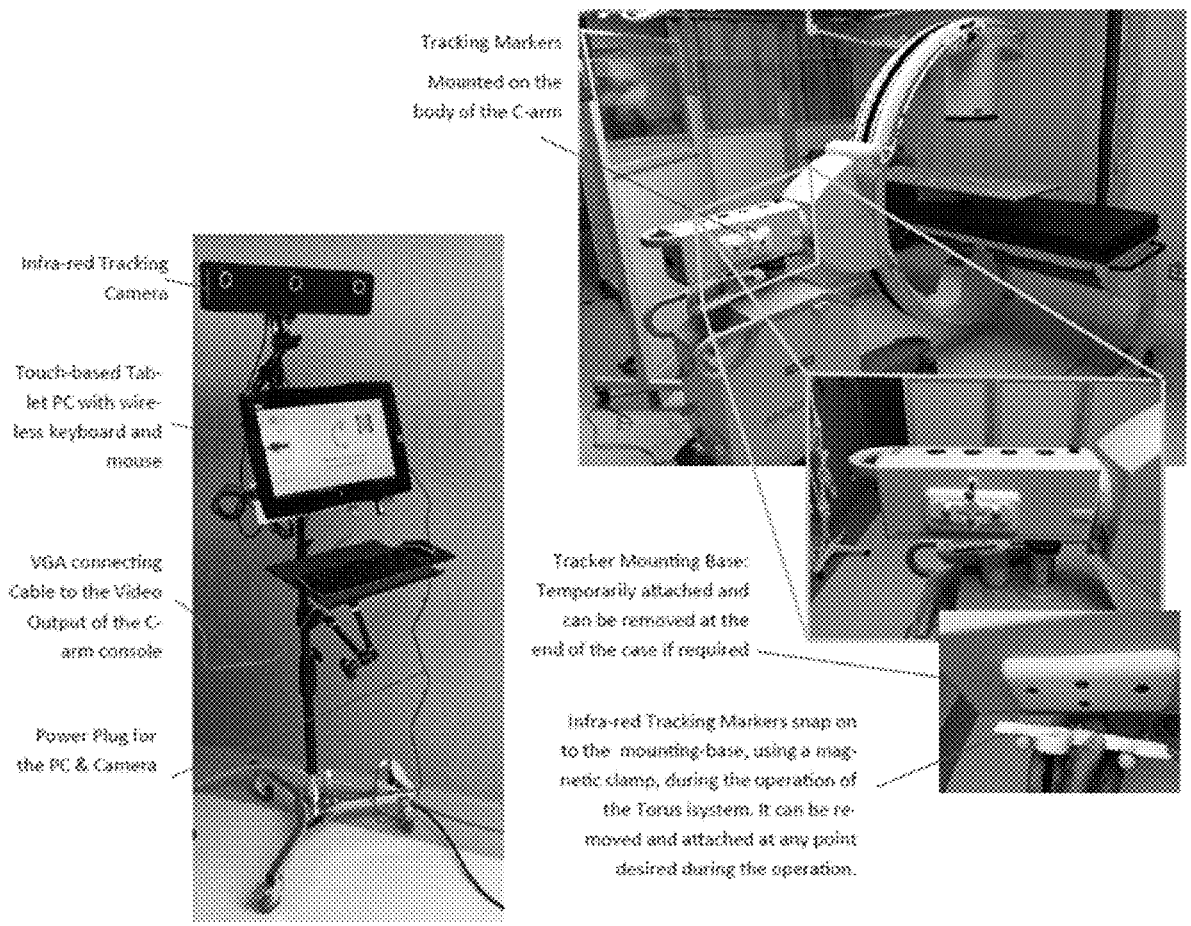

FIG. 17 shows an example embodiment of the hardware and GUI for creating and evaluation of long operative anatomies in the operating room. The hardware in this example includes a mobile computing station that has a processing unit, a tracking camera, a computer with a touch-based interface, and tracking markers mounted on the side of a C-arm X-ray machine. The tracking system may be calibrated as described, for example, in Amiri, WO 2015/051468 which is hereby incorporated herein by reference. WO 2015/051468 also describes a system that may be used to provide complete spatial information that fully describes the position and orientation of the x-ray source and detector for each acquired image.

Example Embodiments of Processing Elements

Systems as described herein include apparatus that performs computations such as one or more of determining transformations, transforming and displaying images, receiving user input, reconstructing areas of a patient's anatomy in three dimensions, transforming and/or displaying templates etc. The apparatus that performs such functions may take any of a wide variety of forms as would be understood by those skilled in the art of image processing and computation.

Embodiments of the invention may be implemented using specifically designed hardware, configurable hardware, programmable data processors configured by the provision of software (which may optionally comprise "firmware") capable of executing on the data processors, special purpose computers or data processors that are specifically programmed, configured, or constructed to perform one or more steps in a method as explained in detail herein and/or combinations of two or more of these. For example, any of these technologies may be applied to perform methods for generating long images of the anatomy according to any of the methods described herein. Examples of specifically designed hardware are: logic circuits, application-specific integrated circuits ("ASICs"), large scale integrated circuits ("LSIs"), very large scale integrated circuits ("VLSIs"), and the like. Examples of configurable hardware are: one or more programmable logic devices such as programmable array logic ("PALs"), programmable logic arrays ("PLAs"), and field programmable gate arrays ("FPGAs")). Examples of programmable data processors are: microprocessors, digital signal processors ("DSPs"), embedded processors, graphics processors, math co-processors, general purpose computers, server computers, cloud computers, mainframe computers, computer workstations, and the like. For example, one or more data processors in a control circuit for an image splicing module or device may implement methods as described herein by executing software instructions in a program memory accessible to the processors.

Processing may be centralized or distributed. Where processing is distributed, information including software and/or data may be kept centrally or distributed. Such information may be exchanged between different functional units by way of a communications network, such as a Local Area Network (LAN), Wide Area Network (WAN), or the Internet, wired or wireless data links, electromagnetic signals, or other data communication channel.

While processes or blocks are presented in a given order, alternative examples may perform routines having steps, or employ systems having blocks, in a different order, and some processes or blocks may be deleted, moved, added, subdivided, combined, and/or modified to provide alternative or subcombinations. Each of these processes or blocks may be implemented in a variety of different ways. Also, while processes or blocks are at times shown as being performed in series, those of skill in the art will recognize that in some instances such processes or blocks may instead be performed in parallel, or may be performed at different times.

The invention may also be provided in the form of a program product. The program product may comprise any non-transitory medium which carries a set of computer-readable instructions which, when executed by a data processor, cause the data processor to execute a method of the invention. For example a program product may comprise a set of instructions that control one or more data processors to assemble and/or display a long image as described herein. Program products according to the invention may be in any of a wide variety of forms. The program product may comprise, for example, non-transitory media such as magnetic data storage media including floppy diskettes, hard disk drives, optical data storage media including CD ROMs, DVDs, electronic data storage media including ROMs, flash RAM, EPROMs, hardwired or preprogrammed chips (e.g., EEPROM semiconductor chips), nanotechnology memory, or the like. The computer-readable signals on the program product may optionally be compressed or encrypted.

In some embodiments, the invention may be implemented in software. For greater clarity, "software" includes any instructions executed on a processor, and may include (but is not limited to) firmware, resident software, microcode, and the like. Both processing hardware and software may be centralized or distributed (or a combination thereof), in whole or in part, as known to those skilled in the art. For example, software and other modules may be accessible via local memory, via a network, via a browser or other application in a distributed computing context, or via other means suitable for the purposes described above.

Where a component (e.g. a software module, processor, assembly, device, circuit, etc.) is referred to herein, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

Specific examples of systems, methods and apparatus have been described herein for purposes of illustration. These are only examples. The technology provided herein can be applied to systems other than the example systems described above. Many alterations, modifications, additions, omissions, and permutations are possible within the practice of this invention. This invention includes variations on described embodiments that would be apparent to the skilled addressee, including variations obtained by: replacing features, elements and/or acts with equivalent features, elements and/or acts; mixing and matching of features, elements and/or acts from different embodiments; combining features, elements and/or acts from embodiments as described herein with features, elements and/or acts of other technology; and/or omitting combining features, elements and/or acts from described embodiments.

Interpretation of Terms

Unless the context clearly requires otherwise, throughout the description and the claims:

"comprise", "comprising", and the like are to be construed in an inclusive sense, as opposed to an exclusive or exhaustive sense; that is to say, in the sense of "including, but not limited to";

"connected", "coupled", or any variant thereof, means any connection or coupling, either direct or indirect, between two or more elements; the coupling or connection between the elements can be physical, logical, or a combination thereof;

"herein", "above", "below", and words of similar import, when used to describe this specification, shall refer to this specification as a whole, and not to any particular portions of this specification;

"or", in reference to a list of two or more items, covers all of the following interpretations of the word: any of the items in the list, all of the items in the list, and any combination of the items in the list;

the singular forms "a", "an", and "the" also include the meaning of any appropriate plural forms.

Words that indicate directions such as "vertical", "transverse", "horizontal", "upward", "downward", "forward", "backward", "inward", "outward", "vertical", "transverse", "left", "right", "front", "back", "top", "bottom", "below", "above", "under", and the like, used in this description and any accompanying claims (where present), depend on the specific orientation of the apparatus described and illustrated. The subject matter described herein may assume various alternative orientations. Accordingly, these directional terms are not strictly defined and should not be interpreted narrowly.

The following references describe related technologies forming part of the current state of the art.

[1] P. Dewaele, P. Vuylsteke, S. Van De Velde, and E. Schoeters, "Full-leg/full-spine image stitching, a new and accurate CR-based imaging technique," vol. 3661, no. February, pp. 131-138, 1999.

[2] C. Vidal, B. Ilharreborde, S. Queinnec, and K. Mazda, "Role of intraoperative radiographs in the surgical treatment of adolescent idiopathic scoliosis," *J. Pediatr. Orthop.*, vol. 00, no. 00, 2015.

[3] H. Livyatan, Z. Yaniv, and L. Joskowicz, "Robust automatic C-Arm calibration for fluoroscopy-based navigation: a practical approach," in *Medical Image Computing and Computer-Assisted Intervention (MICCAI 2002)*, 2002, vol. 2489, pp. 60-68.

[4] B. Kainz, M. Grabner, and M. Rüther, "Fast marker based C-Arm pose estimation," *Med. Image Comput. Comput. Assist. Interv.*, vol. 11, no. Pt 2, pp. 652-9, 2008.

[5] V. Grzeda and G. Fichtinger, "C-arm rotation encoding with accelerometers," *Int. J. Comput. Assist. Radiol. Surg.*, vol. 5, no. 4, pp. 385-91, 2010.

[6] S. Amiri, D. R. Wilson, B. A. Masri, G. Sharma, and C. Anglin, "A novel multi-planar radiography method for three dimensional pose reconstruction of the patellofemoral and tibiofemoral joints after arthroplasty," *J. Biomech.*, vol. 44, no. 9, pp. 1757-1764, 2011.

[7] S. Reaungamornrat, Y. Otake, A. Uneri, S. Schafer, D. J. Mirota, S. Nithiananthan, J. W. Stayman, A. J. Khanna, D. D. Reh, G. L. Gallia, R. H. Taylor, and J. H. Siewerdsen, "Tracker-on-C for cone-beam CT-guided surgery: evaluation of geometric accuracy and clinical applications," *Proc. SPIE*, vol. 8316. pp. 831609-831611, 2012.

[8] N. Navab, S. M. Heining, and J. Traub, "Camera augmented mobile C-arm (CAMC): calibration, accuracy study, and clinical applications," *IEEE Trans Med Imaging*, vol. 29, no. 7, pp. 1412-1423, 2010.

[9] L. Wang, J. Traub, S. M. Heining, S. Benhimane, E. Euler, R. Graumann, and N. Navab, "Long bone X-ray image stitching using camera augmented mobile C-arm," *Med. Image Comput. Comput. Assist. Interv.*, vol. 11, no. Pt 2, pp. 578-86, 2008.

[10] L. Wang, J. Traub, S. Weidert, S. M. Heining, E. Euler, and N. Navab, "Parallax-free intra-operative X-ray image stitching," *Med. Image Anal.*, vol. 14, no. 5, pp. 674-686, 2010.

[11] Z. Yaniv and L. Joskowicz, "Long bone panoramas from fluoroscopic X-ray images," *IEEE Trans. Med. Imaging*, vol. 23, no. 1, pp. 26-35, 2004.

[12] C. Chen, R. Kojcev, D. Haschtmann, T. Fekete, L. Nolte, and G. Zheng, "Ruler Based Automatic C-Arm Image Stitching Without Overlapping Constraint," *J. Digit. Imaging*, 2015.

[13] P. Messmer, F. Matthews, C. Pietro Regazzoni, and A. L. Jacob, "Image fusion for intraoperative control of axis in long bone fracture treatment," *Eur J Trauma*, vol. 32, no. 6, pp. 555-561, 2006.

[14] T. Apivatthakakul, M. Duanghakrung, S. Luevitoonvechkit, and S. Patumasutra, "Intraoperative panoramic image using alignment grid, is it accurate?," *Arch. Orthop. Trauma Surg.*, vol. 133, no. 7, pp. 953-959, 2013.

[15] N. Supakul, K. Newbrough, M. D. Cohen, and S. G. Jennings, "Diagnostic errors from digital stitching of scoliosis images—the importance of evaluating the source images prior to making a final diagnosis," *Pediatr. Radiol.*, vol. 42, no. 5, pp. 584-98, 2012.

[16] S. Amiri, D. R. Wilson, B. A. Masri, and C. Anglin, "A low-cost tracked C-arm (TC-arm) upgrade system for versatile quantitative intraoperative imaging," *Int. J. Comput. Assist. Radiol. Surg.*, vol. 9, no. 4, pp. 695-711, 2014.

[17] S. Bassi, S. Baldini, C. Rebuffat, R. Sarti, and F. Ferretti, "First test on three stitching methods with digital detectors used in radiography," *Radiol. Phys. Technol.*, vol. 6, no. 1, pp. 187-196, 2013.

[18] R. Nathaniel, "METHOD AND SYSTEM FOR STITCHING MULTIPLE IMAGES INTO A PANORAMIC IMAGE," US 2011/0188726 A1.

It is therefore intended that the claims below and any other claims hereafter introduced may claim any and all such modifications, permutations, additions, omissions, and subcombinations as may reasonably be inferred. The available scope of such claims should not be limited by the preferred embodiments set forth in the examples, but should be given the broadest interpretation consistent with the description as a whole.

What is claimed is:

1. Apparatus for medical imaging comprising:
an x-ray machine;
a tracking system operative to determine pose and position of the x-ray machine;
a system comprising one or more data processors connected to receive image data for images acquired by the x-ray machine and pose and position data from the tracking system corresponding to the images; and
a display;
wherein the system is configured by machine-readable instructions executable by the one or more data processors to generate long calibrated two-dimensional radiographic views by:
prompting a user to position the x-ray machine relative to a patient in a first orientation, such that the x-ray machine has a known relationship to anatomical planes of a body of the patient and/or an operative anatomy;
prompting the user to position the x-ray machine relative to the patient in a second orientation;
calculating a three-dimensional vector representation of one or more of the anatomical planes based at least in part on a beam geometry of the x-ray machine from the respective first and second orientations of the x-ray machine, where each plane is orthogonal to the other planes;
transforming images of the patient acquired by the x-ray machine in the first and second orientations onto the one or more anatomical planes based on the vector representation, the beam geometry of the x-ray machine, and the positions and poses of the x-ray machine corresponding to the images;
displaying on the display at least two long views each one corresponding to one or more of the one or more anatomical planes, each of the one or more long views comprising a plurality of the transformed images.

2. The apparatus according to claim 1 wherein the system is configured to check for movement of the patient relative to the reference frame of the tracking system and/or to correct the relationship of the reference frame of the tracking system and the patient by processing one or more confirmatory images to automatically locate distinct visual features and comparing locations of the distinct visual features in the confirmatory images with locations of the distinct visual features in one or more of the long views.

3. The apparatus according to claim 2 wherein the system is configured to recalculate the three-dimensional vector representation of the one or more anatomical planes of the patient based on locations of the distinct visual features in the confirmatory images.

4. The apparatus according to claim 2 wherein the system is configured to recreate the long views by transforming the images of the patient onto the one or more anatomical planes based on the recalculated vector representation, the beam geometry of the x-ray machine, and the positions and poses of the x-ray machine corresponding to the images.

5. The apparatus according to claim 2 wherein the distinct visual features comprise images of artificial fiducial markers.

6. The apparatus according to claim 5 wherein the fiducial markers comprise an array of markers having known positions relative to one another.

7. The apparatus according to claim 5 wherein the fiducial markers comprise radiopaque balls.

8. The apparatus according to claim 2 wherein the system is configured to process the confirmatory images to locate the distinct visual features automatically using a feature recognition algorithm.

9. The apparatus according to claim 1 wherein the system is configured to process the positions and poses of the x-ray machine to determine an image location of an image that could be taken with the x-ray machine at a current pose and position and to display on the display indicia indicating the image location relative to the long view of the patient.

10. The apparatus according to claim 9 wherein the indicia comprises one or more of a cross hair, a circle, a box, a highlight of a field of view of the image that could be taken and an outline of the field of view of the image that could be taken.

11. The apparatus according to claim 1 wherein the system is configured to create a new long view in a new plane different from any of the anatomical planes and to display the new long view on the display.

12. The apparatus according to claim 11 wherein the new plane is parallel to and spaced apart from one of the anatomical planes.

13. The apparatus according to claim 1 wherein the system is configured by the machine-readable instructions to position the x-ray machine to acquire one or more scout images of the patient, the one or more scout images including one or more fiducial features that bear a known relationship to the patient's anatomical planes; wherein calculating the vector representation is based on the beam geometry of the x-ray machine, the positions and poses of the x-ray machine corresponding to the one or more scout images and positions of the one or more fiducial features in the scout images.

14. The apparatus according to claim 1 comprising an alignment guide comprising a laser operable to emit a beam having a known direction relative to the x-ray machine wherein the system is configured by the machine-readable instructions to prompt the user to position the x-ray machine in alignment with one or more axes corresponding to the anatomical planes using the alignment guide.

15. The apparatus according to claim 2 wherein the system is configured to prompt the user to: align the x-ray machine over the top of the two hips in a sequence on the coronal plane and align the x-ray machine with the approximate centre of the patient's hips in a the sagittal view; to store pose and position information from the tracking system for each of these views; and to identify the mediolateral direction of the patient's anatomy by determining parameters defining a mediolateral line connecting the patient's hips, and determining parameters specifying a sagittal anatomical plane at the mid-point of the mediolateral line and normal to the mediolateral line.

16. The apparatus according to claim 1 wherein the system is configured to regenerate one or more of the long views by transforming the images of the patient onto the one or more anatomical planes based on a recalculated three-dimensional vector representation of the one or more anatomical planes, the recalculated three-dimensional vector representation corresponding to corrected positions and orientations of the anatomical planes, the beam geometry of the x-ray machine, and the positions and poses of the x-ray machine corresponding to the images.

17. The apparatus according to claim 16 wherein: the system is configured to selectively display a template on the display, the template overlaid on the long view; the template is associated with a coordinate system; the apparatus is configured to allow a user to reconfigure the template by one or more of moving, rotating and/or scaling the template; and the apparatus is configured to correct estimated positions and orientations of the anatomical planes of the patient based on a configuration of the template.

18. The apparatus according to claim 1 wherein the system is configured to selectively display a template on the display, the template overlaid on the long view.

19. The apparatus according to claim 18 wherein the template comprises a grid corresponding to a desired anatomical plane.

20. The apparatus according to claim 18 wherein the system is configured to receive user input to align the template and to apply a rotation and/or displacement to correct locations of the anatomical planes based on the alignment of the template.

21. The apparatus according to claim 18 wherein the template has an adjustable shape and the system is configured to allow the template to be moved, rotated, scaled, and/or warped.

22. The apparatus according to claim 21 wherein the template comprises indicia corresponding to anatomical features of the patient and the apparatus is configured to allow the template to be adjusted in position and/or orientation as well as one or both of shape and scale to align the indicia with the corresponding anatomical features in the long view.

23. The apparatus according to claim 22 wherein the apparatus is configured to correct positions and orientations of the anatomical planes based on a configuration of the template.

24. The apparatus according to claim 1 wherein the system is configured to provide a plurality of movable templates wherein the plurality of templates share at least one coordinate.

25. The apparatus of claim 22 wherein a first one of the plurality of templates is positioned on a first one of the anatomical planes and a second one of the templates is positioned on a second one of the anatomical planes and moving the first template on the first anatomical plane in a direction corresponding to the shared coordinate causes movement of the second template on the second anatomical plane in the direction corresponding to the shared coordinate.

26. The apparatus according to claim 1 wherein the system is configured to apply image segmentation to automatically recognize and determine locations of distinct visual features in the images of the patient and to automatically determine and apply a shift and/or rotation of the long view.

27. The apparatus according to claim 1 wherein the system is configured to apply user input to guide machine identification of structures and/or apply machine vision technology to refine user input identifying structures.

28. The apparatus according to claim 1 wherein the system is further configured to adjust the transformed images for parallax by steps comprising: displaying first and second long views respectively corresponding to first and second ones of the anatomical planes on the display; based on corresponding points on anatomical structures of the patient's anatomy in each of the first and second long views, determining a depth of the anatomical structure relative to the first and second anatomical planes; and recalculating coordinates of pixels in the transformed images using the determined depth of the anatomical structure.

29. The apparatus according to claim 28 wherein the system is configured to recalculate the coordinates of the pixels in one of the transformed images by generating a plurality of control points spaced apart along the image, estimating a depth of pixels corresponding to each of the control points, computing corrected locations for the control points based on the estimated depths and generating a projective transformation that transforms the image to a parallax-corrected version of the image.

30. The apparatus according to claim 28 wherein the system is configured to receive user inputs identifying the corresponding points.

31. The apparatus according to claim 30 wherein the user input comprises input by way of a touch screen or pointing device that permits a user to swipe across a length of the long views to mark the approximate shape of a feature of the patient's anatomy and wherein the system is configured to process the user input to create a voxel three-dimensional reconstruction of the shape of the feature of the patient's anatomy.

32. The apparatus according to claim 28 wherein the first and second long views comprise stereo long views and the system is further configured to adjust the transformed images for parallax by steps comprising: applying an image segmentation algorithm to identify corresponding points along a feature of the patient's anatomy in the stereo long views and reprocessing the transforming of the images based on three dimensional locations corresponding to pairs of the corresponding points.

33. The apparatus according to claim 28 wherein the system comprises one or more stored models corresponding to the anatomical structures and the system is configured to fit the stored models to the transformed images in the first and second planes by model-based image matching.

34. The apparatus according to claim 1 wherein the system is configured to import shape information defining a three-dimensional shape of a structure of the patient's anatomy relative to the anatomical planes and, in transforming the images of the patient onto the one or more anatomical planes, the system is configured to use the shape information to correct each of the images for parallax before adding the image to the one or more long views.

35. The apparatus according to claim 1 wherein the system is configured to determine areas of overlap of the images and to adjust pixel values in the long views in the areas of overlap by one of blending or overwriting.

36. The apparatus according to claim 1 wherein the system is configured to import a surgical plan and to display graphical elements from the surgical plan on the display overlaid on one or more of the long views.

37. The apparatus according to claim 36 wherein the system is configured to register the surgical plan to the patient based at least in part on the vector representation of the one or more anatomical planes.

38. The apparatus according to claim 36 wherein the surgical plan includes one or more guiding lines and the system is configured to overlay the guiding lines on one or more of the long views.

39. The apparatus according to claim 36 where the surgical plan includes one or more preoperative planning images of the patient and the system is configured to display on the display one or more of the planning images and to superpose on the displayed planning image indicia indicating an image location of an image that could be taken with the x-ray machine at a current pose and position of the x-ray machine.

40. The apparatus according to claim 39 wherein the system is configured to receive user input commands that guide translation and/or rotation and/or scaling of the preoperative planning images to register the preoperative planning images with the long views or other images acquired by the x-ray machine.

41. The apparatus according to claim 36 where the surgical plan includes one or more preoperative planning images of the patient and the system is configured to selectively display on the display one or more of the planning images superposed on one or more of the long views.

42. The apparatus according to claim 36 wherein the surgical plan comprises one or more overlays comprising indicia that provide one or more rulers or protractors to allow direct visual measurements of differences in one or more locations and/or angles from corresponding locations and/or angles specified by the surgical plan and the system is configured to selectively overlay one or more of the overlays on the one or more long views.

43. The apparatus according to claim 36 wherein the system is configured to automatically register the surgical plan to the one or more anatomical planes.

44. The apparatus according to claim 43 wherein the surgical plan includes one or more coordinates of an origin and/or vector directions relative to anatomical planes and the system is configured to automatically register the surgical plan to the anatomical planes determined by the system.

45. The apparatus according to claim 36 wherein the surgical plan is based on stereo-views and the system is configured to overlay the stereo views on real-time intra-operative views acquired by the x-ray machine.

46. The apparatus according to claim 36 wherein the surgical plan is a 3D surgical plan and the system is configured to register the 3D surgical plan into alignment with anatomical directions determined by the system and to overlay the surgical plan on real-time intra-operative views acquired by the x-ray machine.

47. The apparatus according to claim 1 wherein the system is configured to co-register a measurement template which includes indicia indicating one or more positions, spacings or angles with the images, and transforming the measurement template into the viewpoint of the long view such that quantitative measurements are preserved.

48. The apparatus according to claim 1 wherein the system is configured to identify a position corresponding to a first landmark of the patient's anatomy in plural long views and to localize the first landmark in three-dimensions based on the identified positions.

49. The apparatus according to claim 48 wherein the system is configured to identify a position corresponding to a second landmark of the patient's anatomy in the plural long views, determine a location of the second landmark in three-dimensions based on the identified positions and to automatically calculate a distance between the first and second landmarks in three dimensions.

50. The apparatus according to claim 1 wherein the apparatus comprises a user interface that provides a tool for making 2D linear or angular measurements on the long view.

51. The apparatus according to claim 1 wherein the long views comprise stereo long views, the stereo long views including first and second long views respectively corresponding to first and second different planes and the user interface provides measurement tools on the first and second long views that are operable to provide 3D measurements of the patient's anatomy.

52. The apparatus according to claim 1 wherein the system is configured to automatically superpose a template on a live x-ray image of the patient and to automatically set placement, orientation and scaling of the superposed template based on the pose and position of the x-ray machine determined by the tracking system.

53. The apparatus according to claim 1 wherein the system comprises a plurality of templates and is configured to select one of the plurality of templates based on the pose and position of the x-ray machine determined by the tracking system and to superpose the selected template on a live x-ray image.

* * * * *